(12) United States Patent
Govindappa et al.

(10) Patent No.: US 12,351,636 B2
(45) Date of Patent: *Jul. 8, 2025

(54) FUSION IMMUNOMODULATORY PROTEINS AND METHODS FOR MAKING SAME

(71) Applicant: BIOCON LTD., Bangalore (IN)

(72) Inventors: Nagaraj Govindappa, Karnataka (IN); Maria Melina Soares, Karnataka (IN); Kedarnath Sastry, Karnataka (IN)

(73) Assignee: Biocon Ltd., Bangalore (IN)

( * ) Notice: Subject to any disclaimer, the term of this patent is extended or adjusted under 35 U.S.C. 154(b) by 881 days.

This patent is subject to a terminal disclaimer.

(21) Appl. No.: 17/010,178

(22) Filed: Sep. 2, 2020

(65) Prior Publication Data

US 2020/0399379 A1 Dec. 24, 2020

Related U.S. Application Data

(60) Continuation of application No. 15/968,122, filed on May 1, 2018, now Pat. No. 10,766,963, which is a division of application No. 14/771,308, filed as application No. PCT/US2014/022404 on Mar. 10, 2014, now Pat. No. 9,988,456.

(60) Provisional application No. 61/777,016, filed on Mar. 12, 2013.

(51) Int. Cl.
| | |
|---|---|
| *C07K 16/28* | (2006.01) |
| *C07K 14/705* | (2006.01) |
| *C07K 14/71* | (2006.01) |
| *C12N 15/62* | (2006.01) |
| *A61K 38/00* | (2006.01) |

(52) U.S. Cl.
CPC ........ *C07K 16/2863* (2013.01); *C07K 14/705* (2013.01); *C07K 14/71* (2013.01); *C07K 16/2818* (2013.01); *C12N 15/62* (2013.01); *A61K 38/00* (2013.01); *C07K 2317/40* (2013.01); *C07K 2317/526* (2013.01); *C07K 2317/90* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 7,141,651 B2 | 11/2006 | Gillies et al. | |
| 8,815,247 B2 | 8/2014 | Govindappa et al. | |
| 9,340,617 B2 | 5/2016 | Govindappa et al. | |
| 9,452,149 B2 | 9/2016 | Nilsson et al. | |
| 9,758,582 B2 | 9/2017 | Govindappa et al. | |
| 9,809,651 B2 | 11/2017 | Govindappa et al. | |
| 9,988,456 B2 | 6/2018 | Govindappa et al. | |
| 10,144,934 B2 | 12/2018 | Govindappa et al. | |
| 10,385,348 B2 | 8/2019 | Govindappa et al. | |
| 10,766,963 B2 | 9/2020 | Govindappa et al. | |
| 11,028,399 B2 | 6/2021 | Govindappa et al. | |
| 12,049,632 B2 | 7/2024 | Govindappa et al. | |
| 2010/0273202 A1 | 10/2010 | Inouye et al. | |
| 2010/0284971 A1 | 11/2010 | Samulski | |
| 2010/0297697 A1 | 11/2010 | Ambrosius et al. | |
| 2011/0104734 A1 | 5/2011 | Croughan et al. | |
| 2013/0039911 A1* | 2/2013 | Bedi ................. C07K 16/2866 |
| | | | 530/391.1 |
| 2020/0399379 A1* | 12/2020 | Govindappa ...... C07K 16/2863 |
| 2021/0301296 A1 | 9/2021 | Govindappa et al. | |

FOREIGN PATENT DOCUMENTS

| | | |
|---|---|---|
| CN | 101511373 A | 8/2009 |
| EP | 0361902 | 9/1989 |
| JP | H02-163096 | 6/1990 |
| RU | 2120475 C1 | 10/1998 |
| WO | WO 199833914 | 8/1998 |
| WO | WO-0155163 A1 | 8/2001 |
| WO | WO-0158957 A2 | 8/2001 |
| WO | WO2002083854 | 10/2002 |
| WO | WO2008077889 | 7/2008 |
| WO | WO2009027471 | 3/2009 |
| WO | WO 2009039409 | 3/2009 |
| WO | WO 2009114110 | 9/2009 |
| WO | WO2011102845 | 8/2011 |
| WO | WO 2011109789 | 9/2011 |
| WO | WO-2012033953 A1 | 3/2012 |
| WO | WO-2012147048 A2 | 11/2012 |
| WO | WO 2012147053 | 11/2012 |
| WO | WO 2013004841 | 1/2013 |
| WO | WO201316469 | 11/2013 |
| WO | WO-2014164427 A1 | 10/2014 |

OTHER PUBLICATIONS

Altschul, Stephen et al. "Basic Local Alignment Search Tool." 1990, *J. Mol. Biol.* 15:403-10.

Birch, J. R. et al. "Antibody production." Advanced Drug Delivery Reviews, vol. 58, No. 5-6, Aug. 7, 2006.

Bitter, Grant et al. "Expression and Secretion Vectors for Yeast." 1987, *Methods in Enzymology*. 153:516-544.

Carton et al. "Codon engineering for improved antibody expression in mammalian cells." Protein Expression and Purification, Academic Press, vol. 55, No. 2, Sep. 8, 2007.

Casi, Giulio et al. "Antibody drug conjugates: Basic concepts, examples and future perspectives." Journal of Controlled Release, vol. 161, No. 2, Jan. 10, 2012.

Dick, Lawrence W. et al. "C-Terminal Lysine Variants in Fully Human Monoclonal Antibodies: Investigation of Test Methods and Possible Causes." Biotechnology and Bioengineering, vol. 100, No. 6, Aug. 15, 2008.

(Continued)

*Primary Examiner* — Daniel C Gamett
(74) *Attorney, Agent, or Firm* — COOLEY LLP

(57) ABSTRACT

The present invention relates generally to the field of generating recombinant chimeric fusion proteins to be used in the cancer therapy, and more specifically, to fusion molecules of Anti-EGFR1-TGFβRII, Anti-EGFR1-PD1 and Anti-CTLA4-PD1 and methods of generating same, wherein the methods reduce production costs and increase homogeneity of the recombinant chimeric fusion proteins.

2 Claims, 66 Drawing Sheets

Specification includes a Sequence Listing.

(56) References Cited

OTHER PUBLICATIONS

Dong, Mei et al. "Role of transforming growth factor-ß in hematologic malignancies." 2006, *Blood.* 107:4589-4596.

Fath, Stephan, et al. "Multiparameter RNA and Codon Optimization: A Standardized Tool to Access and Enhance Autologous Mammalian Gene Expression." 2011, *PLOS one,* art, No. e17596, 6:1-14.

Flies, Dallas B. et al. "Blockade of the B7-H1/PD-1 Pathway for Cancer Immunotherapy." 2011, *J Biol Med.,* 84:409-421.

Kalwy, S. et al. "Toward more efficient protein expression." Molecular Biotechnology, Humana Press, Inc., vol. 34, No. 2, Sp. Iss. SI, Oct. 1, 2006.

Kotsopoulou, E. et al. "Optimised mammalian expression through the coupling of codon adaptation with gene amplification; maximum yields with minimum effort." Journal of Biotechnology, vol. 146, No. 4, Apr. 15, 2010.

Lee, Robert J. et al. "Delivery of liposomes into cultured KB cells via folate receptor-mediated endocytosis." 1994, *J Biol. Chem.,* 269:3198-3204.

Lee, Robert J. et al. "Folate-mediated tumor cell targeting of liposome-entrapped doxorubicin in vitro." 1995 *Biochem. Biophys. Actu,* 1233:134-144.

Luo, Jun et al. "Probing of C-Terminal Lysine Variation in a Recombinant Monoclonal Antibody Production Using Chinese Hamster Ovary Cells with Chemically Defined Media." Biotechnology and Bioengineering, vol. 109, No. 9, Sep. 11, 2012.

Mackett, Michael et al. "Vaccinia virus: a selectable eukaryotic cloning and expression vector." 1982, *Proc. Natl. Acad. Sci. USA,* 79:7415-7419.

Mackett, Michael et al. "General method for production and selection of infectious vaccinia virus recombinants expressing foreign genes." 1984, *J. Virol.,* 49:857-864.

Nomi, Takeo et al. "Clinical significance and therapeutic potential of the programmed death-1 ligand/programmed death-1 pathway in human pancreatic cancer." 2007, *Clin Cancer Res.,* 13:2151-2157.

Ortiz-Sanchez, Elizabeth et al. "Antibody cytokine fusion proteins: applications in cancer therapy." Expert Opinion on Biological Therapy, vol. 8, No. 5, May 1, 2008.

Okazaki, Taku et al. "PD-1 and PD-1 ligands: from discovery to clinical Application." 2007, *International Immunology,* 19:813-824.

Panicali, Dennis et al. "Construction of poxviruses as cloning vectors: insertion of the thymidine kinase gene from herpes simplex virus into the DNA of infectious vaccine virus." 1982, *Proc. Natl. Acad. Sci. USA,* 79:4927-4931.

Pardoll, Drew M. "The blockage of immune checkpoints in cancer immunotherapy." 2012, *Nat. Rev. Cancer,* 12:252-64.

Raab, David et al. "The GeneOptimizer Algorithm: using a sliding window approach to cope with the vast sequence space in multiparameter DNA sequence optimization." 2010, *Syst Synth Biol.,* 4:215-225.

Sundaram, Shanmuuga et al. "An innovative approach for the characterization of the isoforms of a monoclonal antibody product." MABS, vol. 3, No. 6, Nov. 1, 2011.

Thompson, R. Houston, et al. "Costimulatory B7-H1 in renal cell carcinoma patients: Indicator of tumor aggressiveness and potential therapeutic target." 2004, *Proc Natl Acad Sci U S A.,* 101:17174-9.

Wrzesinski, Stephen et al. "Transforming Growth Factor-ß and the Immune Response: Implications for Anticancer Therapy." 2007, *Clin Cancer Res,* 13:5262-5270.

Altschul, et al. Basic Local Alignment Search Tool. J. Mol. Biol., 1990, pp. 403-410.

Carton et al., Codon engineering for improved antibody expression in mammalian cells, Protein Expression and Purification, Sep. 2007, pp. 279-286.

Cocco, et al. hl-con1, a factor VII-IgGFc chimeric protein targeting tissue factor for immunotherapy of uterine serous papillary carcinoma. British journal of cancer, 2010, pp. 812-819.

European Extended Search Report, corresponding to European Divisional Patent Application No. 18212095, dated Mar. 8, 2019, 11 pages.

European Office Action, corresponding to European Divisional Patent Application No. 18153517.0, dated Mar. 22, 2018, 10 pages.

Fath, et al. Multiparameter RNA and Codon Optimization: A Standardized Tool to Access and Enhance Autologous Mammalian Gene Expression, 2011, PloSone, pp. 1-14.

Giulio, et al. Antibody-drug conjugates: Basic concepts, examples and future perspectives. Journal of Controlled Release, 2012, pp. 422-428.

International Preliminary Report on Patentability for Application No. PCT/US2014/022404 dated Sep. 15, 2015, 11 pages.

International Search Report and Written Opinion for Application No. PCT/US2014/022404 dated Aug. 1, 2014, 15 pages.

Japanese Office Action, corresponding to Japanese Patent Application No. 2016-500960, dated Oct. 18, 2017, 14 pages.

Liu, et al. Heterogeneity of monoclonal antibodies. Pharmaceutical Sciences, American Pharmaceutical Assoc., 2007, pp. 2426-2447.

Luo, J. et al. Comparative metabolite analysis to understand lactate metabolism shift in Chinese hamster ovary cell culture process. Biotechnology and Bioengineering, 2011, pp. 146-156.

Office Action, issued by the European Patent Office for corresponding European Divisional Patent Application No. 18153517.0, dated Mar. 22, 2018, 10 pages.

Office Action, issued by the European Patent Office for corresponding European Patent Application No. 1373158.2, dated Jun. 6, 2017, 9 pages.

Office Action, issued by the Russian Patent Office for corresponding Russian Patent Application No. 2014145158, dated Feb. 14, 2017, 6 pages.

Qian, et al. Cell Culture and Gene Transcription Effects of Copper Sulfate on Chinese Hamster Ovary Cells. Biotechnology Progress, 2011, pp. 1190-1194.

Russian Office Action, corresponding to Russian Divisional Patent Application No. 2018117558, issued by the Patent Office of the Russian Federation dated Jan. 29, 2019, 5 pages.

Author Unknown, Cathepsin L, filed with Notice of Opposition in EP2844667 (Application No. 13734158.2) on Jul. 11, 2019, 3 pages, downloaded/retrieval dated May 23, 2019 from https://www.signmaaldrich.com/life-science/biochemicals/bioche . . .

Author Unknown, Opposition against EP2844667 (Application No. 13734158.2) further efficacy data provided by patentee, filed with Notice of Opposition in EP2844667 on Jan. 27, 2020, 5 pages, downloaded/retrieval date unknown.

Author Unknown, Overview of the embodiments shown in the Figures of D1 filed with Notice of Opposition in EP2844667 (Application No. 13734158.2) on Jul. 11, 2019, 2 pages, downloaded/retrieval date unknown.

Author Unknown, Sequence alignment of i) the amino acid sequence translated from SEQ ID No. 16 and II) the fused amino acid sequence consisting of SEQ ID No. 5 and SEQ ID No. 3 (in this order), annotated copy of D18, dated Feb. 3, 2020, 2 pages, retrieved from https://www.ebi.ac.uk/Tools/services/rest/emboss needle/result/emboss_ needle-12020 . . .

Author Unknown, Sequence alignment of i) the amino acid sequence translated from SEQ ID No. 16 and ii) the fused amino acid sequence consisting of SEQ ID No. 5 and SEQ ID No. 3 (in this order), dated Feb. 3, 2020, 2 pages, retrieved from https://www.ebi.ac.uk/Tools/services/rest/emboss needle/result/emboss_ needle-12020 . . .

Author Unknown, Sequence alignment of SEQ ID No. 104 of D1 v. SEQ ID No. 3 of the patent in suit, 1 page downloaded/retrieval dated Feb. 28, 2019 from https://www.ebi.ac.uk/Tools/services/rest/emboss stretcher/result/emboss_ stretcher-I20190228-100314-0769-22518881-p2m/aln.

Author Unknown, Sequence alignment of SEQ ID No. 2 of D1 v. SEQ ID No. 3 of the patent in suit, 2 pages downloaded/retrieval dated Feb. 28, 2019 from https://www.ebi.ac.uk/Tools/services/rest/emboss stretcher/result/emboss_ stretcher-I20190228-095439-0911-14867179-p1 m/aln.

Author Unknown, Sequence alignment of SEQ ID No. 2 of D1 v. SEQ ID No. 4 of the patent in suit, 2 pages downloaded/retrieval dated Feb. 28, 2019 from https://www.ebi.ac.uk/Tools/services/rest/emboss stretcher/result/emboss_ stretcher-I20190228-094 735-0861-30697382-p2m/aln.

(56) References Cited

OTHER PUBLICATIONS

Author Unknown, Sequence alignment of SEQ ID No. 2 of D1 v. SEQ ID No. 5 of the patent in suit, 2 pages downloaded/retrieval dated Feb. 28, 2019 from https://www.ebi.ac.uk/Tools/services/resUemboss stretcher/resulUemboss stretcher-I20190228-095024-0795-3242854-p2m/aln.
Author Unknown, Sequence alignment of SEQ ID No. 4 of the patent in suit and SEQ ID No. 87 of D1, 1 page downloaded/retrieval dated Feb. 28, 2019 from https://www.ebi.ac.uk/Tools/services/rest/emboss stretcher/result/emboss_ stretcher-I20190228-100057-0250-22316156-p2m/aln.
Author Unknown, Sequence alignment of SEQ ID No. 71 of D1 v. SEQ ID No. 6 of the patent in suit, 1 page downloaded/retrieval dated Feb. 28, 2019 from https://www.ebi.ac.uk/Tools/services/rest/emboss stretcher/result/emboss_ stretcher-I20190228-095226-0857-18483768-p1 m/aln.
Author Unknown, stability data provided by patentee, filed with Notice of Opposition in EP2844667 on Jan. 27, 2020, 7 pages, downloaded/retrieval date unknown.
Author Unknown, Synopsis of the independent claims of EP2844667B1 (Application No. 13734158.2) and U.S. Pat. No. 8,815,247 B2, 1 page, downloaded/retrieval date unknown.
Author Unknown, Technical Report No. DDL/TR/BR.14.09015/19/003, Report title: To evaluate role of FmAb2 in immune cell activation, using an invitro tumour-immune cell coculture assay system, filed with Notice of Opposition in EP2844667 (Application No. 13734158.2) on Jan. 27, 2020, Biocon Research Limited, 20 pages, downloaded/retrieval date unknown.
Author Unknown, Technical Report No. IPL/TR/BR.14.09015/19/001, Report title: Evaluation of anti-tumor activity of FmAb2 in HT-29 (V600E) tumor xenograft model, filed with Notice of Opposition in EP2844667 (Application No. 13734158.2) on Jan. 27, 2020, Biocon Research Limited, 25 pages, downloaded/retrieval date unknown.
Cederholm-Williams, S.A., "Concentration of plasminogen and antiplasmin in plasma and serum," J Clin Pathol 1981; 34:979-981.
Decision Denying Inter Partes Review for Case IPR2016-00175 Patent 8,815,247 B2, filed with Notice of Opposition in EP2844667 (Application No. 13734158.2) on Jul. 11, 2019, 11 pages.
Decision of the Opposition & Instruction dated Mar. 12, 2021 for EP Application No. 13734158.2 (EP2844667), 1 page.
Decision Rejecting the Opposition dated Mar. 12, 2021 for EP Application No. 13734158.2 (EP2844667), 2 pages.
EPO Communication dated Mar. 11, 2019, enclosing Notice of Opposition for EP13734158.2 (EP2844667), 42 pages.
Grounds for the Decision (Annex) Opposition for EP Application No. 13734158.2 (EP2844667) dated Mar. 12, 2021, 16 pages.
Hsieh, et al., Micro-heterogeneity of the monoclonal antibody Erbitux ((TM)) characterized by ion exchange chromatography, isoelectric focusing, peptide mapping, and LC-MS/MS, Abstracts of Papers of The American Chemical Society, Aug. 2004, pp. U195.
Keil, Specificity of Proteolysis, Springer-Verlag Berlin Heidelberg 1992, pp. 6, 12, 67, 108 (8 total pages).
Keil, Specificity of Proteolysis, Springer-Verlag Berlin Heidelberg 1992, pp. 6, 12, 67, 108 (8 total pages), annotated copy.
Magdelaine-Beuzelin, et al., "Structure-function relationships of the variable domains of monoclonal antibodies approved for cancer treatment," Crit Rev Oncol Hematol. Dec. 2007; 64(3):210-25. Epub Jul. 12, 2007.
Nakano, et al., "Molecular genetics of vaccinia virus: demonstration of marker rescue," Proc Natl Acad Sci USA., vol. 79(5), pp. 1593-1596, Mar. 1982.
Notice of Opposition for EP13734158.2 (EP2844667), dated and filed Feb. 28, 2019, with Exhibits, 709 total pages.
Office Action, issued by the European Patent Office for EP Application No. 13734158.2, dated Jul. 27, 2016, 7 pages.
Podar, et al., "Inhibition of the TGF-beta signaling pathway in tumor cells," Recent Results Cancer Res. 2007; 172:77-97.
Schrama, David, et al., "Antibody targeted drugs as cancer therapeutics," Nature Reviews Drug Discovery (2006); 5.2: 147-159.
Summons to attend oral proceedings for EP Application No. 13734158.2 (EP2844667), dated Jun. 22, 2020, 13 pages.
Summons to attend oral proceedings for EP Application No. 13734158.2 (EP2844667), dated Jun. 6, 2017, 9 pages.
Termination of Opposition Proceedings for EP13734158.2 (EP2844667) dated Mar. 30, 2023, 1 page.
Written submission of ABG Patentes dated Nov. 13, 2017 for EP13734158.2 (EP2844667), 11 pages.
Yao, et al., "Contribution of B7-H1/PD-1 Co-inhibitory pathway to T-Cell dysfunction in Cancer," Tumor Induced Immune Suppression: Mechanisms and Therapeutic Reversal 2008 (pp. 29-40). Springer New York.
Author Unknown, Sequence alignment of i) the amino acid sequence translated from SEQ ID No. 16 and ii) the fused amino acid sequence consisting of SEQ ID No. 5 and SEQ ID No. 3 (in this order), annotated copy of D18, dated Feb. 3, 2020, 2 pages, retrieved from https://www.ebi.ac.uk/Tools/services/rest/emboss needle/result/emboss_needle-12020 . . . , full website address unknown, Exhibit D18a as filed with Notice of Opposition in EP2844667 (Application No. 13734158.2) on Jul. 11, 2019.
Author Unknown, Sequence alignment of i) the amino acid sequence translated from SEQ ID No. 16 and ii) the fused amino acid sequence consisting of SEQ ID No. 5 and SEQ ID No. 3 (in this order), dated Feb. 3, 2020, 2 pages, retrieved from https://www.ebi.ac.uk/Tools/services/rest/emboss_needle/result/emboss_needle-12020 . . . , full website address unknown, Exhibit D18 as filed with Notice of Opposition in EP2844667 (Application No. 13734158.2) on Jul. 11, 2019.

* cited by examiner

SEQ ID NO: 1

Codon optimized Anti-EGFR1 Heavy chain sequence:
```
   1 CAGGTGCAGC TGAAGCAGTC TGGCCCTGGC CTGGTGCAGC CCTCCCAGTC CCTGTCCATC
  61 ACCTGTACCG TGTCCGGCTT CTCCCTGACC AACTACGGCG TGCACTGGGT GCGACAGTCC
 121 CCCGGCAAGG GCCTGGAATG GCTGGGAGTG ATTTGGAGCG GCGGCAACAC CGACTACAAC
 181 ACCCCCTTCA CCTCCCGGCT GTCCATCAAC AAGGACAACT CCAAGTCCCA GGTGTTCTTC
 241 AAGATGAACT CCCTGCAGTC CAACGACACC GCCATCTACT ACTGCGCCAG AGCCCTGACC
 301 TACTATGACT ACGAGTTCGC CTACTGGGGC CAGGGCACCC TGGTGACAGT GTCCGCCGCT
 361 TCCACCAAGG GCCCCTCCGT GTTCCCTCTG GCCCCCTCCA GCAAGTCCAC CTCTGGCGGC
 421 ACCGCTGCCC TGGGCTGCCT GGTGAAAGAC TACTTCCCCG AGCCCGTGAC CGTGTCCTGG
 481 AACTCTGGCG CCCTGACCTC CGGCGTGCAC ACCTTCCCTG CCGTGCTGCA GTCCTCCGGC
 541 CTGTACTCCC TGTCCTCCGT GGTGACCGTG CCCTCCAGCT CTCTGGGCAC CCAGACCTAC
 601 ATCTGCAACG TGAACCACAA GCCCTCCAAC ACCAAGGTGG ACAAGCGGGT GGAACCCAAG
 661 TCCTGCGACA AGACCCACAC CTGTCCCCCC TGCCCTGCCC TGAACTGCT GGGCGGACCT
 721 TCCGTGTTCC TGTTCCCCCC AAAGCCCAAG GACACCCTGA TGATCTCCCG GACCCCCGAA
 781 GTGACCTGCG TGGTGGTGGA CGTGTCCCAC GAGGACCCTG AAGTGAAGTT CAATTGGTAC
 841 GTGGACGGCG TGGAAGTGCA CAACGCCAAG ACCAAGCCCA GAGAGGAACA GTACAACTCC
 901 ACCTACCGGG TGGTGTCTGT GCTGACCGTG CTGCACCAGG ACTGGCTGAA CGGCAAAGAG
 961 TACAAGTGCA AGGTGTCCAA CAAGGCCCTG CCTGCCCCCA TCGAAAAGAC CATCTCCAAG
1021 GCCAAGGGCC AGCCCCGCGA GCCCCAGGTG TACACCCTGC CCCCTAGCCG GGACGAGCTG
1081 ACCAAGAACC AGGTGTCCCT GACCTGTCTG GTGAAAGGCT TCTACCCCTC CGATATCGCC
1141 GTGGAATGGG AGTCCAACGG CCAGCCCGAG AACAACTACA AGACCACCCC CCTGTGCTG
1201 GACTCCGACG GCTCATTCTT CCTGTACTCC AAGCTGACCG TGGACAAGTC CCGGTGGCAG
1261 CAGGGCAACG TGTTCTCCTG CTCCGTGATG CACGAGGCCC TGCACAACCA CTACACCCAG
1321 AAGTCCCTGT CTCTGTCCCC CGGC
```

SEQ ID NO: 2
Codon optimized Anti-EGFR1 light chain nucleotide sequence:
```
   1 GACATCCTGC TGACCCAGTC CCCCGTGATC CTGTCCGTGT CTCCTGGCGA GCGGGTGTCC
  61 TTCTCCTGCC GGGCCTCTCA GTCCATCGGC ACCAACATCC ACTGGTATCA GCAGCGGACC
 121 AACGGCTCCC CTCGGCTGCT GATTAAGTAC GCCTCCGAGT CCATCTCCGG CATCCCTTCC
 181 CGGTTCTCCG GCTCCGGCTC TGGCACCGAC TTCACCCTGT CCATCAACTC CGTGGAATCC
 241 GAGGACATTG CCGACTACTA CTGCCAGCAG AACAACAACT GGCCCACCAC CTTCGGCGCT
 301 GGCACCAAGC TGGAACTGAA GCGGACCGTG GCCGCTCCCT CCGTGTTCAT CTTCCCACCC
 361 TCCGACGAGC AGCTGAAGTC CGGCACCGCC TCCGTGGTGT GCCTGCTGAA CAACTTCTAC
 421 CCCCGCGAGG CCAAGGTGCA GTGGAAGGTG GACAACGCCC TGCAGTCCGG CAACTCCCAG
 481 GAATCCGTGA CCGAGCAGGA CTCCAAGGAC AGCACCTACT CCCTGTCCTC CACCCTGACC
 541 CTGTCCAAGG CCGACTACGA GAAGCACAAG GTGTACGCCT GCGAAGTGAC CCACCAGGGC
 601 CTGTCCAGCC CCGTGACCAA GTCCTTCAAC CGGGGCGAGT GT
```

Figure 2

SEQ ID NO: 3
Codon optimized nucleotide sequence of TGFβRII:

```
  1 ACAATCCCTC CACACGTGCA GAAATCCGTG AACAACGACA TGATCGTGAC CGACAACAAT
 61 GGCGCCGTGA AGTTCCCCCA GCTGTGCAAG TTCTGCGACG TGCGGTTCTC TACCTGCGAC
121 AACCAGAAAT CCTGCATGTC CAACTGCTCC ATCACCTCCA TCTGCGAGAA GCCCCAGGAA
181 GTGTGCGTGG CCGTGTGGCG GAAGAACGAC GAGAACATCA CCCTGGAAAC CGTGTGCCAC
241 GACCCCAAGC TGCCCTACCA CGACTTCATC CTGGAAGATG CCGCCTCCCC CAAGTGCATC
301 ATGAAGGAAA AGAAGAAGCC CGGCGAGACT TTCTTCATGT GCAGCTGCTC CTCCGACGA
361 TGCAACGACA ACATCATCTT CTCCGAAGAG TACAACACCT CCAACCCCGA C
```

SEQ ID NO: 4

Codon optimized nucleotide sequence of the Linker:

```
  1 GGAGGCGGAG GATCTGGCGG AGGTGGAAGT GGCGGCGGAG GCTCT
```

SEQ ID NO: 5

Codon optimized nucleotide sequence of AntiCTLA4 heavy chain:

```
   1 CAGGTGCAGC TGGTGGAATC TGGTGGCGGA GTGGTGCAGC CTGGCAGATC CCTGAGACTG
  61 TCTTGTGCCG CCTCCGGCTT CACCTTCTCC TCGTACACCA TGCACTGGGT GCGACAGGCC
 121 CCTGGCAAGG GACTGGAATG GGTCACCTTC ATCTCTTACG ACGGCAACAA CAAGTACTAC
 181 GCCGACTCCG TGAAGGGCCG GTTCACCATC TCCCGGGACA ACTCCAAGAA CACCCTGTAC
 241 CTGCAGATGA ACTCCCTGCG GGCCGAGGAC ACCGCCATCT ACTACTGTGC TAGAACCGGC
 301 TGGCTGGGCC CCTTCGATTA TTGGGGCCAG GGCACCCTCG TGACCGTCTC GAGCGCTAGC
 361 ACAAAGGGCC CTAGTGTGTT TCCTCTGGCT CCCTCTTCCA AATCCACTTC TGGTGGCACT
 421 GCTGCTCTGG GATGCCTGGT GAAGGATTAC TTTCCTGAAC CTGTGACTGT CTCATGGAAC
 481 TCTGGTGCTC TGACTTCTGG TGTCCACACT TTCCCTGCTG TGCTGCAGTC TAGTGGACTG
 541 TACTCTCTGT CATCTGTGGT CACTGTGCCC TCTTCATCTC TGGGAACCCA GACCTACATT
 601 TGTAATGTGA ACCACAAACC ATCCAACACT AAAGTGGACA AACGGGTGGA ACCCAAATCC
 661 TGTGACAAAA CCCACACCTG CCCACCTTGT CCTGCCCCTG AACTGCTGGG AGGACCTTCT
 721 GTGTTTCTGT TCCCCCCCAA ACCAAAGGAT ACCCTGATGA TCTCTAGAAC CCCTGAGGTG
 781 ACATGTGTGG TGGTGGATGT GTCTCATGAG GACCCTGAGG TCAAATTCAA CTGGTACGTG
 841 GATGGAGTGG AAGTCCACAA TGCCAAAACC AAGCCTAGAG AGGAACAGTA CAATTCAACC
 901 TACAGAGTGG TCAGTGTGCT GACTGTGCTG CATCAGGATT GGCTGAATGG CAAGGAATAC
 961 AAGTGTAAAG TCTCAAACAA GGCCCTGCCT GCTCCAATTG AGAAAACAAT CTCAAAGGCC
1021 AAGGGACAGC CTAGGGAACC CCAGGTCTAC ACCCTGCCAC CTTCAAGAGA TGAACTGACC
1081 AAAAACCAGG TGTCCCTGAC ATGCCTGGTC AAAGGCTTCT ACCCTTCTGA CATTGCTGTG
1141 GAGTGGGAGT CAAATGGACA GCCTGAGAAC AACTACAAAA CAACCCCCCC TGTGCTGGAT
1201 TCTGATGGCT CTTTCTTTCT GTACTCCAAA CTGACTGTGG ACAAGTCTAG ATGGCAGCAG
1261 GGGAATGTCT TTCTTGCTC TGTCATGCAT GAGGCTCTGC ATAACCACTA CACTCAGAAA
1321 TCCCTGTCTC TGTCTCCCGG G
```

Figure 2 Cont.

SEQ ID NO: 6

Codon optimized nucleotide sequence of Anti-CTLA4 light chain:
```
  1 GAGATCGTGC TGACCCAGTC TCCTGGCACC CTGTCTCTGA GCCCTGGCGA GAGAGCTACC
 61 CTGTCCTGCA GAGCCTCTCA GTCCGTGGGC TCCTCTTACC TGGCCTGGTA TCAACAAAAA
121 CCCGGCCAAG CTCCCCGGCT GCTGATCTAC GGTGCCTTTT CTCGCGCCAC CGGCATCCCC
181 GACCGGTTCT CCGGATCTGG CTCTGGCACC GACTTCACCC TGACCATCTC CCGGCTGGAA
241 CCCGAGGACT TCGCCGTGTA CTACTGCCAG CAGTACGGCT CCTCCCCCTG GACCTTTGGC
301 CAGGGCACCA AGGTGGAAAT CAAACGTACG GTCGCGGCGC CTTCCGTGTT CATCTTCCCA
361 CCCTCCGACG AGCAGCTGAA GTCCGGCACC GCCTCCGTGG TGTGCCTGCT GAACAACTTC
421 TACCCCGCG AGGCCAAGGT GCAGTGGAAG GTGGACAACG CCCTGCAGTC CGGCAACTCC
481 CAGGAATCCG TGACCGAGCA GGACTCCAAG GACAGCACCT ACTCCCTGTC CTCCACCCTG
541 ACCCTGTCCA AGGCCGACTA CGAGAAGCAC AAGGTGTACG CCTGCGAAGT GACCCACCAG
601 GGCCTGTCCA GCCCCGTGAC CAAGTCCTTC AACCGGGGCG AGTGT
```

SEQ ID NO: 7

Codon optimized nucleotide sequence of PD1
```
  1 CCTGGCTGGT TTCTGGACTC CCCTGACCGG CCCTGGAACC CCCCAACCTT CTCTCCTGCC
 61 CTGCTGGTGG TGACAGAGGG CGACAACGCC ACCTTCACCT GTTCCTTCAG CAACACCTCC
121 GAGTCCTTCG TGCTGAACTG GTACAGAATG TCCCCCAGCA ACCAGACCGA CAAGCTGGCC
181 GCCTTCCCCG AGGACAGATC CCAGCCTGGC CAGGACTGCC GGTTCAGAGT GACCCAGCTG
241 CCCAACGGCC GGGACTTCCA CATGTCCGTG GTGCAGCCA GACGGAACGA CTCCGGCACC
301 TACCTGTGCG CGCCATCTC TCTGGCCCCC AAGGCCCAGA TCAAAGAGTC CCTGCGGGCC
361 GAGCTGAGAG TGACCGAGAG AAGGGCCGAG GTGCCCACCG CCCACCCTAG CCCATCTCCA
421 AGACCTGCCG GCCAGTTCCA GACCCTGGTG
```

Figure 2 Cont.

SEQ ID NO: 8

Amino acid sequence of Anti-EGFR1 Heavy Chain constant

QVQLKQSGPGLVQPSQSLSITCTVSGFSLTNYGVHWVRQSPGKGLEWL
GVIWSGGNTDYNTPFTSRLSINKDNSKSQVFFKMNSLQSNDTAIYYCAR
ALTYYDYEFAYWGQGTLVTVSAASTKGPSVFPLAPSSKSTSGGTAALG
CLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNH
YTQKSLSLSPG

SEQ ID NO: 9

Amino acid sequence of Anti-EGFR1 Light chain

DILLTQSPVILSVSPGERVSFSCRASQSIGTNIHWYQQRTNGSPRLLIKYA
SESISGIPSRFSGSGSGTDFTLSINSVESEDIADYYCQQNNNWPTTFGAGT
KLELKRTVAAPSVFIFPPSDEQLKSGTASVVCLLNNFYPREAKVQWKVD
NALQSGNSQESVTEQDSKDSTYSLSSTLTLSKADYEKHKVYACEVTHQ
GLSSPVTKSFNRGEC

SEQ ID NO: 10

Amino acid sequence of linker

GGGGSGGGGSGGGGS

SEQ ID NO: 11

Amino acid sequence of PD1

PGWFLDSPDRPWNPPTFSPALLVVTEGDNATFTCSFSNTSESFVLNWYR
MSPSNQTDKLAAFPEDRSQPGQDCRFRVTQLPNGRDFHMSVVRARRND
SGTYLCGAISLAPKAQIKESLRAELRVTERRAEVPTAHPSPSPRPAGQFQ
TLV

Figure 3

SEQ ID NO: 8

Amino acid sequence of Anti-EGFR1 Heavy Chain constant

QVQLKQSGPGLVQPSQSLSITCTVSGFSLTNYGVHWVRQSPGKGLE
WLGVIWSGGNTDYNTPFTSRLSINKDNSKSQVFFKMNSLQSNDTAIY
YCARALTYYDYEFAYWGQGTLVTVSAASTKGPSVFPLAPSSKSTSG
GTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWY
VDGVEVHNAKTKPREEQYNSTYRVVSVLTVLHQDWLNGKEYKCK
VSNKALPAPIEKTISKAKGQPREPQVYTLPPSRDELTKNQVSLTCLV
KGFYPSDIAVEWESNGQPENNYKTTPPVLDSDGSFFLYSKLTVDKSR
WQQGNVFSCSVMHEALHNHYTQKSLSLSPG

SEQ ID NO: 9

Amino acid sequence of Anti-EGFR1 Light chain

DILLTQSPVILSVSPGERVSFSCRASQSIGTNIHWYQQRTNGSPRLLIK
YASESISGIPSRFSGSGSGTDFTLSINSVESEDIADYYCQQNNNWPTTF
GAGTKLELKRTVAAPSVFIFPPSDEQLKSGTASVVCLLNNFYPREAK
VQWKVDNALQSGNSQESVTEQDSKDSTYSLSSTLTLSKADYEKHKV
YACEVTHQGLSSPVTKSFNRGEC

SEQ ID NO: 10

Amino acid sequence of linker

GGGGSGGGGSGGGGS

SEQ ID NO: 12

Amino acid sequence of TGFRII

TIPPHVQKSVNNDMIVTDNNGAVKFPQLCKFCDVRFSTCDNQKSCMSNCSITS
ICEKPQEVCVAVWRKNDENITLETVCHDPKLPYHDFILEDAASPKCIMKEKKK
PGETFFMCSCSSDECNDNIIFSEEYNTSNPD

Figure 4

SEQ ID NO: 13

Amino acid sequence of Anti-CTLA-4 Heavy Chain constant

QVQLVESGGGVVQPGRSLRLSCAASGFTFSSYTMHWVRQAPGKGLEWVTFISY
DGNNKYYADSVKGRFTISRDNSKNTLYLQMNSLRAEDTAIYYCARTGWLGPFD
YWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVF
SCSVMHEALHNHYTQKSLSLSPG

SEQ ID NO: 14

Amino acid sequence of Anti-CTLA-4 Light chain

EIVLTQSPGTLSLSPGERATLSCRASQSVGSSYLAWYQQKPGQAPRLLIYGAF
SRATGIPDRFSGSGSGTDFTLTISRLEPEDFAVYYCQQYGSSPWTFGQGTKVE
IKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNR
GEC

SEQ ID NO: 10

Amino acid sequence of linker

GGGGSGGGGSGGGGS

SEQ ID NO: 11

Amino acid sequence of PD1

PGWFLDSPDRPWNPPTFSPALLVVTEGDNATFTCSFSNTSESFVLNW
YRMSPSNQTDKLAAFPEDRSQPGQDCRFRVTQLPNGRDFHMSVVR
ARRNDSGTYLCGAISLAPKAQIKESLRAELRVTERRAEVPTAHPSPS
PRPAGQFQTLV

Figure 5

5. Anti-EGFR1-PD1 (HC-C-terminus):

Amino acid sequence of Anti-EGFR1 HC constant- PD1 fusion protein: SEQ ID NO: 15

QVQLKQSGPGLVQPSQSLSITCTVSGFSLTNYGVHWVRQSPGKGLE
WLGVIWSGGNTDYNTPFTSRLSINKDNSKSQVFFKMNSLQSNDTAIY
YCARALTYYDYEFAYWGQGTLVTVSAASTKGPSVFPLAPSSKSTSG
GTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWY
VDGVEVHNAKTKPREEQYNSTYRVVSVLTVLHQDWLNGKEYKCK
VSNKALPAPIEKTISKAKGQPREPQVYTLPPSRDELTKNQVSLTCLV
KGFYPSDIAVEWESNGQPENNYKTTPPVLDSDGSFFLYSKLTVDKSR
WQQGNVFSCSVMHEALHNHYTQKSLSLSPG*GGGGSGGGGSGGGGS*
PGWFLDSPDRPWNPPTFSPALLVVTEGDNATFTCSFSNTSESFVLNW
YRMSPSNQTDKLAAFPEDRSQPGQDCRFRVTQLPNGRDFHMSVVR
ARRNDSGTYLCGAISLAPKAQIKESLRAELRVTERRAEVPTAHPSPS
PRPAGQFQTLV

Amino acid sequence of Anti-EGFR1 light chain: SEQ ID NO: 9
DILLTQSPVILSVSPGERVSFSCRASQSIGTNIHWYQQRTNGSPRLLIK
YASESISGIPSRFSGSGSGTDFTLSINSVESEDIADYYCQQNNNWPTTF
GAGTKLELKRTVAAPSVFIFPPSDEQLKSGTASVVCLLNNFYPREAK
VQWKVDNALQSGNSQESVTEQDSKDSTYSLSSTLTLSKADYEKHKV
YACEVTHQGLSSPVTKSFNRGEC

Figure 7

6. Anti-EGFR1-PD1 (LC-C-terminus):

Amino acid sequence of Anti-EGFR1 heavy chain: SEQ ID NO: 8

QVQLKQSGPGLVQPSQSLSITCTVSGFSLTNYGVHWVRQSPGKGLEWL
GVIWSGGNTDYNTPFTSRLSINKDNSKSQVFFKMNSLQSNDTAIYYCAR
ALTYYDYEFAYWGQGTLVTVSAASTKGPSVFPLAPSSKSTSGGTAALG
CLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNH
YTQKSLSLSPG

Amino acid sequence of Anti-EGFR1 LC constant-PD1 fusion protein: SEQ ID NO: 16

DILLTQSPVILSVSPGERVSFSCRASQSIGTNIHWYQQRTNGSPRLLIKYA
SESISGIPSRFSGSGSGTDFTLSINSVESEDIADYYCQQNNNWPTTFGAGT
KLELKRTVAAPSVFIFPPSDEQLKSGTASVVCLLNNFYPREAKVQWKVD
NALQSGNSQESVTEQDSKDSTYSLSSTLTLSKADYEKHKVYACEVTHQ
GLSSPVTKSFNRGEC*GGGGSGGGGSGGGGS*PGWFLDSPDRPWNPPTFSP
ALLVVTEGDNATFTCSFSNTSESFVLNWYRMSPSNQTDKLAAFPEDRSQ
PGQDCRFRVTQLPNGRDFHMSVVRARRNDSGTYLCGAISLAPKAQIKES
LRAELRVTERRAEVPTAHPSPSRPAGQFQTLV

Figure 8

7. Anti-EGFR1-PD1 (HC-N-terminus):

Amino acid sequence of PD1-Anti-EGFR1 HC variable fusion protein: SEQ ID NO: 17

PGWFLDSPDRPWNPPTFSPALLVVTEGDNATFTCSFSNTSESFVLNW
YRMSPSNQTDKLAAFPEDRSQPGQDCRFRVTQLPNGRDFHMSVVR
ARRNDSGTYLCGAISLAPKAQIKESLRAELRVTERRAEVPTAHPSPS
PRPAGQFQTLV*GGGGSGGGGSGGGGS*QVQLKQSGPGLVQPSQSLSIT
CTVSGFSLTNYGVHWVRQSPGKGLEWLGVIWSGGNTDYNTPFTSR
LSINKDNSKSQVFFKMNSLQSNDTAIYYCARALTYYDYEFAYWGQG
TLVTVSAASTKGPSVFPLAPSSKSTSGGTAALGCLVKDYFPEPVTVS
WNSGALTSGVHTFPAVLQSSGLYSLSSVVTVPSSSLGTQTYICNVNH
KPSNTKVDKRVEPKSCDKTHTCPPCPAPELLGGPSVFLFPPKPKDTL
MISRTPEVTCVVVDVSHEDPEVKFNWYVDGVEVHNAKTKPREEQY
NSTYRVVSVLTVLHQDWLNGKEYKCKVSNKALPAPIEKTISKAKGQ
PREPQVYTLPPSRDELTKNQVSLTCLVKGFYPSDIAVEWESNGQPEN
NYKTTPPVLDSDGSFFLYSKLTVDKSRWQQGNVFSCSVMHEALHN
HYTQKSLSLSPG

Amino acid sequence of Anti-EGFR1 light chain: SEQ ID NO: 9

DILLTQSPVILSVSPGERVSFSCRASQSIGTNIHWYQQRTNGSPRLLIK
YASESISGIPSRFSGSGSGTDFTLSINSVESEDIADYYCQQNNNWPTTF
GAGTKLELKRTVAAPSVFIFPPSDEQLKSGTASVVCLLNNFYPREAK
VQWKVDNALQSGNSQESVTEQDSKDSTYSLSSTLTLSKADYEKHKV
YACEVTHQGLSSPVTKSFNRGEC

Figure 9

8. Anti-EGFR1-PD1 (LC-N-terminus):

Amino acid sequence of Anti-EGFR1 heavy chain: SEQ ID NO: 8

QVQLKQSGPGLVQPSQSLSITCTVSGFSLTNYGVHWVRQSPGKGLE
WLGVIWSGGNTDYNTPFTSRLSINKDNSKSQVFFKMNSLQSNDTAIY
YCARALTYYDYEFAYWGQGTLVTVSAASTKGPSVFPLAPSSKSTSG
GTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWY
VDGVEVHNAKTKPREEQYNSTYRVVSVLTVLHQDWLNGKEYKCK
VSNKALPAPIEKTISKAKGQPREPQVYTLPPSRDELTKNQVSLTCLV
KGFYPSDIAVEWESNGQPENNYKTTPPVLDSDGSFFLYSKLTVDKSR
WQQGNVFSCSVMHEALHNHYTQKSLSLSPG

Amino acid sequence of PD1-Anti-EGFR1 LC variable fusion protein: SEQ ID NO: 18

PGWFLDSPDRPWNPPTFSPALLVVTEGDNATFTCSFSNTSESFVLNW
YRMSPSNQTDKLAAFPEDRSQPGQDCRFRVTQLPNGRDFHMSVVR
ARRNDSGTYLCGAISLAPKAQIKESLRAELRVTERRAEVPTAHPSPS
PRPAGQFQTLV*GGGGSGGGGSGGGGS*DILLTQSPVILSVSPGERVSFS
CRASQSIGTNIHWYQQRTNGSPRLLIKYASESISGIPSRFSGSGSGTDF
TLSINSVESEDIADYYCQQNNNWPTTFGAGTKLELKRTVAAPSVFIF
PPSDEQLKSGTASVVCLLNNFYPREAKVQWKVDNALQSGNSQESVT
EQDSKDSTYSLSSTLTLSKADYEKHKVYACEVTHQGLSSPVTKSFNR
GEC

Figure 10

Expression constructs developed using the cDNAs:

1. Anti-EGFR1-TGFRII (HC-C-terminus):

Amino acid sequence of Anti-EGFR1 HC constant-TGFβRII fusion protein: SEQ ID NO: 27

QVQLKQSGPGLVQPSQSLSITCTVSGFSLTNYGVHWVRQSPGKGLEWLGVIWSGGNTDYNTP
FTSRLSINKDNSKSQVFFKMNSLQSNDTAIYYCARALTYYDYEFAYWGQGTLVTVSAASTKG
PSVFPLAPSSKSTSGGTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEAL
HNHYTQKSLSLSPGGGGGSGGGGSGGGGSTIPPHVQKSVNNDMIVTDNNGAVKFPQLCKFCD
VRFSTCDNQKSCMSNCSITSICEKPQEVCVAVWRKNDENITLETVCHDPKLPYHDFILEDAA
SPKCIMKEKKKPGETFFMCSCSSDECNDNIIFSEEYNTSNPD

Amino acid sequence of Anti-EGFR1 light chain: SEQ ID NO: 9

DILLTQSPVILSVSPGERVSFSCRASQSIGTNIHWYQQRTNGSPRLLIKYASESISGIPSRF
SGSGSGTDFTLSINSVESEDIADYYCQQNNNWPTTFGAGTKLELKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC

Figure 13

2. Anti-EGFR1-TGFβRII (LC-C-terminus):

Amino acid sequence of Anti-EGFR1 heavy chain: SEQ ID NO: 8
QVQLKQSGPGLVQPSQSLSITCTVSGFSLTNYGVHWVRQSPGKGLEWLGVIWSGGNTDYNTP
FTSRLSINKDNSKSQVFFKMNSLQSNDTAIYYCARALTYYDYEFAYWGQGTLVTVSAASTKG
PSVFPLAPSSKSTSGGTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEAL
HNHYTQKSLSLSPG Amino acid sequence of Anti-EGFR1 LC constant-TGFβRII fusion protein: SEQ ID NO: 28

DILLTQSPVILSVSPGERVSFSCRASQSIGTNIHWYQQRTNGSPRLLIKYASESISGIPSRF
SGSGSGTDFTLSINSVESEDIADYYCQQNNNWPTTFGAGTKLELKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGECGGGGSGGGGSGGGGSTIPPHVQKSVNNDMIVTDN
NGAVKFPQLCKFCDVRFSTCDNQKSCMSNCSITSICEKPQEVCVAVWRKNDENITLETVCHD
PKLPYHDFILEDAASPKCIMKEKKKPGETFFMCSCSSDECNDNIIFSEEYNTSNPD

Figure 14

3. Anti-EGFR1-TGFβRII (HC-N-terminus):

Amino acid sequence of TGFβRII-Anti-EGFR1 HC variable fusion protein: SEQ ID NO: 29

TIPPHVQKSVNNDMIVTDNNGAVKFPQLCKFCDVRFSTCDNQKSCMSNCSITSICEKPQEVC
VAVWRKNDENITLETVCHDPKLPYHDFILEDAASPKCIMKEKKKPGETFFMCSCSSDECNDN
IIFSEEYNTSNPDGGGGSGGGGSGGGGSQVQLKQSGPGLVQPSQSLSITCTVSGFSLTNYGV
HWVRQSPGKGLEWLGVIWSGGNTDYNTPFTSRLSINKDNSKSQVFFKMNSLQSNDTAIYYCA
RALTYYDYEFAYWGQGTLVTVSAASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKRVEPK
SCDKTHTCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPG

Amino acid sequence of Anti-EGFR1 light chain: SEQ ID NO: 9

DILLTQSPVILSVSPGERVSFSCRASQSIGTNIHWYQQRTNGSPRLLIKYASESISGIPSRF
SGSGSGTDFTLSINSVESEDIADYYCQQNNNWPTTFGAGTKLELKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC

Figure 15

4. Anti-EGFR1-TGFβRII (LC-N-terminus):

Amino acid sequence of Anti-EGFR1 heavy chain: SEQ ID NO: 8
QVQLKQSGPGLVQPSQSLSITCTVSGFSLTNYGVHWVRQSPGKGLEWLGVIWSGGNTDYNTP
FTSRLSINKDNSKSQVFFKMNSLQSNDTAIYYCARALTYYDYEFAYWGQGTLVTVSAASTKG
PSVFPLAPSSKSTSGGTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEAL
HNHYTQKSLSLSPG Amino acid sequence of TGFβRII-Anti-EGFR1 LC variable fusion
protein: SEQ ID NO: 30

TIPPHVQKSVNNDMIVTDNNGAVKFPQLCKFCDVRFSTCDNQKSCMSNCSITSICEKPQEVC
VAVWRKNDENITLETVCHDPKLPYHDFILEDAASPKCIMKEKKKPGETFFMCSCSSDECNDN
IIFSEEYNTSNPDGGGGSGGGGSGGGGSDILLTQSPVILSVSPGERVSFSCRASQSIGTNIH
WYQQRTNGSPRLLIKYASESISGIPSRFSGSGSGTDFTLSINSVESEDIADYYCQQNNNWPT
TFGAGTKLELKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC

Figure 16

9. Anti-EGFR1-TGFβRII (HC-C-terminus & LC- C-terminus):

Amino acid sequence of Anti-EGFR1 HC constant-TGFβRII fusion protein: SEQ ID NO: 31

QVQLKQSGPGLVQPSQSLSITCTVSGFSLTNYGVHWVRQSPGKGLEWLGVIWSGGNTDYNTP
FTSRLSINKDNSKSQVFFKMNSLQSNDTAIYYCARALTYYDYEFAYWGQGTLVTVSAASTKG
PSVFPLAPSSKSTSGGTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEAL
HNHYTQKSLSLSPGGGGSGGGGSGGGGSTIPPHVQKSVNNDMIVTDNNGAVKFPQLCKFCD
VRFSTCDNQKSCMSNCSITSICEKPQEVCVAVWRKNDENITLETVCHDPKLPYHDFILEDAA
SPKCIMKEKKKPGETFFMCSCSSDECNDNIIFSEEYNTSNPD

Amino acid sequence of Anti-EGFR1 LC constant- TGFβRII fusion: SEQ ID NO: 28

DILLTQSPVILSVSPGERVSFSCRASQSIGTNIHWYQQRTNGSPRLLIKYASESISGIPSRF
SGSGSGTDFTLSINSVESEDIADYYCQQNNNWPTTFGAGTKLELKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGECGGGGSGGGGSGGGGSTIPPHVQKSVNNDMIVTDN
NGAVKFPQLCKFCDVRFSTCDNQKSCMSNCSITSICEKPQEVCVAVWRKNDENITLETVCHD
PKLPYHDFILEDAASPKCIMKEKKKPGETFFMCSCSSDECNDNIIFSEEYNTSNPD

Figure 17

10. Anti-EGFR1-TGFβRII (HC-C-terminus & LC- N-terminus):

Amino acid sequence of Anti-EGFR1 HC constant-TGFβRII fusion protein: SEQ ID NO: 31

QVQLKQSGPGLVQPSQSLSITCTVSGFSLTNYGVHWVRQSPGKGLEWLGVIWSGGNTDYNTP
FTSRLSINKDNSKSQVFFKMNSLQSNDTAIYYCARALTYYDYEFAYWGQGTLVTVSAASTKG
PSVFPLAPSSKSTSGGTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEAL
HNHYTQKSLSLSPGGGGGSGGGGSGGGGSTIPPHVQKSVNNDMIVTDNNGAVKFPQLCKFCD
VRFSTCDNQKSCMSNCSITSICEKPQEVCVAVWRKNDENITLETVCHDPKLPYHDFILEDAA
SPKCIMKEKKKPGETFFMCSCSSDECNDNIIFSEEYNTSNPD

Amino acid sequence of TGFβRII-Anti-EGFR1 LC variable fusion protein: SEQ ID NO: 30

TIPPHVQKSVNNDMIVTDNNGAVKFPQLCKFCDVRFSTCDNQKSCMSNCSITSICEKPQEVC
VAVWRKNDENITLETVCHDPKLPYHDFILEDAASPKCIMKEKKKPGETFFMCSCSSDECNDN
IIFSEEYNTSNPDGGGGSGGGGSGGGGSDILLTQSPVILSVSPGERVSFSCRASQSIGTNIH
WYQQRTNGSPRLLIKYASESISGIPSRFSGSGSGTDFTLSINSVESEDIADYYCQQNNNWPT
TFGAGTKLELKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC

Figure 18

11. Anti-EGFR1-TGFβRII (HC-N-terminus & LC- C-terminus):

Amino acid sequence of TGFβRII-Anti-EGFR1 HC variable fusion protein: SEQ ID NO: 29

TIPPHVQKSVNNDMIVTDNNGAVKFPQLCKFCDVRFSTCDNQKSCMSNCSITSICEKPQEVC
VAVWRKNDENITLETVCHDPKLPYHDFILEDAASPKCIMKEKKKPGETFFMCSCSSDECNDN
IIFSEEYNTSNPDGGGGSGGGGSGGGGSQVQLKQSGPGLVQPSQSLSITCTVSGFSLTNYGV
HWVRQSPGKGLEWLGVIWSGGNTDYNTPFTSRLSINKDNSKSQVFFKMNSLQSNDTAIYYCA
RALTYYDYEFAYWGQGTLVTVSAASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKRVEPK
SCDKTHTCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPG

Amino acid sequence of Anti-EGFR1 LC constant-TGFβRII fusion protein: SEQ ID NO: 28

DILLTQSPVILSVSPGERVSFSCRASQSIGTNIHWYQQRTNGSPRLLIKYASESISGIPSRF
SGSGSGTDFTLSINSVESEDIADYYCQQNNNWPTTFGAGTKLELKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGECGGGGSGGGGSGGGGSTIPPHVQKSVNNDMIVTDN
NGAVKFPQLCKFCDVRFSTCDNQKSCMSNCSITSICEKPQEVCVAVWRKNDENITLETVCHD
PKLPYHDFILEDAASPKCIMKEKKKPGETFFMCSCSSDECNDNIIFSEEYNTSNPD

Figure 19

12. Anti-EGFR1-TGFβRII (HC-N-terminus & LC- N-terminus):

Amino acid sequence of TGFβRII-Anti-EGFR1 Hc variable fusion protein: SEQ ID NO: 29

TIPPHVQKSVNNDMIVTDNNGAVKFPQLCKFCDVRFSTCDNQKSCMSNCSITSICEKPQEVC
VAVWRKNDENITLETVCHDPKLPYHDFILEDAASPKCIMKEKKKPGETFFMCSCSSDECNDN
IIFSEEYNTSNPDGGGGSGGGGSGGGGSQVQLKQSGPGLVQPSQSLSITCTVSGFSLTNYGV
HWVRQSPGKGLEWLGVIWSGGNTDYNTPFTSRLSINKDNSKSQVFFKMNSLQSNDTAIYYCA
RALTYYDYEFAYWGQGTLVTVSAASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKRVEPK
SCDKTHTCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPG

Amino acid sequence of TGFβRII-Anti-EGFR1 LC variable fusion protein: SEQ ID NO: 30

TIPPHVQKSVNNDMIVTDNNGAVKFPQLCKFCDVRFSTCDNQKSCMSNCSITSICEKPQEVC
VAVWRKNDENITLETVCHDPKLPYHDFILEDAASPKCIMKEKKKPGETFFMCSCSSDECNDN
IIFSEEYNTSNPDGGGGSGGGGSGGGGSDILLTQSPVILSVSPGERVSFSCRASQSIGTNIH
WYQQRTNGSPRLLIKYASESISGIPSRFSGSGSGTDFTLSINSVESEDIADYYCQQNNNWPT
TFGAGTKLELKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC

Figure 20

13. Anti-CTLA4-PD1 (HC-C-terminus):

Amino acid sequence of Anti-CTLA4 HC constant-PD1 fusion protein: SEQ ID NO: 32

QVQLVESGGGVVQPGRSLRLSCAASGFTFSSYTMHWVRQAPGKGLEWVTFISYDGNNKYYAD
SVKGRFTISRDNSKNTLYLQMNSLRAEDTAIYYCARTGWLGPFDYWGQGTLVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEALH
NHYTQKSLSLSPGGGGSGGGGSGGGGSPGWFLDSPDRPWNPPTFSPALLVVTEGDNATFTC
SFSNTSESFVLNWYRMSPSNQTDKLAAFPEDRSQPGQDCRFRVTQLPNGRDFHMSVVRARRN
DSGTYLCGAISLAPKAQIKESLRAELRVTERRAEVPTAHPSPSRPAGQFQTLV

Amino acid sequence of Anti-CTLA4 light chain: SEQ ID NO: 14

EIVLTQSPGTLSLSPGERATLSCRASQSVGSSYLAWYQQKPGQAPRLLIYGAFSRATGIPDR
FSGSGSGTDFTLTISRLEPEDFAVYYCQQYGSSPWTFGQGTKVEIKRTVAAPSVFIFPPSDE
QLKSGTASVVCLLNNFYPREAKVQWKVDNALQSGNSQESVTEQDSKDSTYSLSSTLTLSKAD
YEKHKVYACEVTHQGLSSPVTKSFNRGEC

Figure 25

14. Anti-CTLA4-PD1 (LC-C-terminus):

Amino acid sequence of Anti-CTLA4 heavy chain: SEQ ID NO: 13

QVQLVESGGGVVQPGRSLRLSCAASGFTFSSYTMHWVRQAPGKGLEWVTFISYDGNNKYYAD
SVKGRFTISRDNSKNTLYLQMNSLRAEDTAIYYCARTGWLGPFDYWGQGTLVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEALH
NHYTQKSLSLSPG

Amino acid sequence of Anti-CTLA4 LC constant-PD1 fusion protein: SEQ ID NO: 33

EIVLTQSPGTLSLSPGERATLSCRASQSVGSSYLAWYQQKPGQAPRLLIYGAFSRATGIPDR
FSGSGSGTDFTLTISRLEPEDFAVYYCQQYGSSPWTFGQGTKVEIKRTVAAPSVFIFPPSDE
QLKSGTASVVCLLNNFYPREAKVQWKVDNALQSGNSQESVTEQDSKDSTYSLSSTLTLSKAD
YEKHKVYACEVTHQGLSSPVTKSFNRGECGGGGSGGGGSGGGGSPGWFLDSPDRPWNPPTFS
PALLVVTEGDNATFTCSFSNTSESFVLNWYRMSPSNQTDKLAAFPEDRSQPGQDCRFRVTQL
PNGRDFHMSVVRARRNDSGTYLCGAISLAPKAQIKESLRAELRVTERRAEVPTAHPSPSRP
AGQFQTLV

Figure 26

15. Anti-CTLA4-PD1 (HC-N-terminus):

Amino acid sequence of PD1-Anti-CTLA4 HC variable fusion protein: SEQ ID NO: 34

PGWFLDSPDRPWNPPTFSPALLVVTEGDNATFTCSFSNTSESFVLNWYRMSPSNQTDKLAAF
PEDRSQPGQDCRFRVTQLPNGRDFHMSVVRARRNDSGTYLCGAISLAPKAQIKESLRAELRV
TERRAEVPTAHPSPSPRPAGQFQTLVGGGGSGGGGSGGGGSQVQLVESGGGVVQPGRSLRLS
CAASGFTFSSYTMHWVRQAPGKGLEWVTFISYDGNNKYYADSVKGRFTISRDNSKNTLYLQM
NSLRAEDTAIYYCARTGWLGPFDYWGQGTLVTVSSASTKGPSVFPLAPSSKSTSGGTAALGC
LVKDYFPEPVTVSWNSGALTSGVHTFPAVLQSSGLYSLSSVVTVPSSSLGTQTYICNVNHKP
SNTKVDKRVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPG

Amino acid sequence of Anti-CTLA4 light chain: SEQ ID NO: 14

EIVLTQSPGTLSLSPGERATLSCRASQSVGSSYLAWYQQKPGQAPRLLIYGAFSRATGIPDR
FSGSGSGTDFTLTISRLEPEDFAVYYCQQYGSSPWTFGQGTKVEIKRTVAAPSVFIFPPSDE
QLKSGTASVVCLLNNFYPREAKVQWKVDNALQSGNSQESVTEQDSKDSTYSLSSTLTLSKAD
YEKHKVYACEVTHQGLSSPVTKSFNRGEC

Figure 27

16. Anti-CTLA4-PD1 (LC-N-terminus):

Amino acid sequence of Anti-CTLA4 heavy chain: SEQ ID NO: 13

QVQLVESGGGVVQPGRSLRLSCAASGFTFSSYTMHWVRQAPGKGLEWVTFISYDGNNKYYAD
SVKGRFTISRDNSKNTLYLQMNSLRAEDTAIYYCARTGWLGPFDYWGQGTLVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEALH
NHYTQKSLSLSPG

Amino acid sequence of PD1-Anti-CTLA4 LC variable fusion
protein: SEQ ID NO: 35

PGWFLDSPDRPWNPPTFSPALLVVTEGDNATFTCSFSNTSESFVLNWYRMSPSNQTDKLAAF
PEDRSQPGQDCRFRVTQLPNGRDFHMSVVRARRNDSGTYLCGAISLAPKAQIKESLRAELRV
TERRAEVPTAHPSPSPRPAGQFQTLVGGGGSGGGGSGGGGSEIVLTQSPGTLSLSPGERATL
SCRASQSVGSSYLAWYQQKPGQAPRLLIYGAFSRATGIPDRFSGSGSGTDFTLTISRLEPED
FAVYYCQQYGSSPWTFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVT
KSFNRGEC

Figure 28

17. Anti-CTLA4-PD1 (HC-C-terminus & LC- C-terminus):

Amino acid sequence of Anti-CTLA4 HC constant-PD1 fusion protein: SEQ ID NO: 32

QVQLVESGGGVVQPGRSLRLSCAASGFTFSSYTMHWVRQAPGKGLEWVTFISYDGNNKYYAD
SVKGRFTISRDNSKNTLYLQMNSLRAEDTAIYYCARTGWLGPFDYWGQGTLVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEALH
NHYTQKSLSLSPGGGGSGGGGSGGGGSPGWFLDSPDRPWNPPTFSPALLVVTEGDNATFTC
SFSNTSESFVLNWYRMSPSNQTDKLAAFPEDRSQPGQDCRFRVTQLPNGRDFHMSVVRARRN
DSGTYLCGAISLAPKAQIKESLRAELRVTERRAEVPTAHPSPSRPAGQFQTLV

Amino acid sequence of Anti-CTLA4 LC constant-PD1 fusion protein: SEQ ID NO: 33

EIVLTQSPGTLSLSPGERATLSCRASQSVGSSYLAWYQQKPGQAPRLLIYGAFSRATGIPDR
FSGSGSGTDFTLTISRLEPEDFAVYYCQQYGSSPWTFGQGTKVEIKRTVAAPSVFIFPPSDE
QLKSGTASVVCLLNNFYPREAKVQWKVDNALQSGNSQESVTEQDSKDSTYSLSSTLTLSKAD
YEKHKVYACEVTHQGLSSPVTKSFNRGECGGGGSGGGGSGGGGSPGWFLDSPDRPWNPPTFS
PALLVVTEGDNATFTCSFSNTSESFVLNWYRMSPSNQTDKLAAFPEDRSQPGQDCRFRVTQL
PNGRDFHMSVVRARRNDSGTYLCGAISLAPKAQIKESLRAELRVTERRAEVPTAHPSPSRP
AGQFQTLV

Figure 29

18. Anti-CTLA4-PD1 (HC-C-terminus & LC- N-terminus):

Amino acid sequence of Anti-CTLA4 HC constant-PD1 fusion protein: SEQ ID NO: 32

QVQLVESGGGVVQPGRSLRLSCAASGFTFSSYTMHWVRQAPGKGLEWVTFISYDGNNKYYAD
SVKGRFTISRDNSKNTLYLQMNSLRAEDTAIYYCARTGWLGPFDYWGQGTLVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEALH
NHYTQKSLSLSPGGGGSGGGGSGGGGSPGWFLDSPDRPWNPPTFSPALLVVTEGDNATFTC
SFSNTSESFVLNWYRMSPSNQTDKLAAFPEDRSQPGQDCRFRVTQLPNGRDFHMSVVRARRN
DSGTYLCGAISLAPKAQIKESLRAELRVTERRAEVPTAHPSPSRPAGQFQTLV

Amino acid sequence of PD1-Anti-CTLA4 LC variable fusion protein: SEQ ID NO: 35

PGWFLDSPDRPWNPPTFSPALLVVTEGDNATFTCSFSNTSESFVLNWYRMSPSNQTDKLAAF
PEDRSQPGQDCRFRVTQLPNGRDFHMSVVRARRNDSGTYLCGAISLAPKAQIKESLRAELRV
TERRAEVPTAHPSPSRPAGQFQTLVGGGGSGGGGSGGGGSEIVLTQSPGTLSLSPGERATL
SCRASQSVGSSYLAWYQQKPGQAPRLLIYGAFSRATGIPDRFSGSGSGTDFTLTISRLEPED
FAVYYCQQYGSSPWTFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVT
KSFNRGEC

Figure 30

19. Anti-CTLA4-PD1 (HC-N-terminus & LC- C-terminus):

Amino acid sequence of PD1-Anti-CTLA4 HC variable fusion protein: SEQ ID NO: 34

PGWFLDSPDRPWNPPTFSPALLVVTEGDNATFTCSFSNTSESFVLNWYRMSPSNQTDKLAAF
PEDRSQPGQDCRFRVTQLPNGRDFHMSVVRARRNDSGTYLCGAISLAPKAQIKESLRAELRV
TERRAEVPTAHPSPSPRPAGQFQTLVGGGGSGGGGSGGGGSQVQLVESGGGVVQPGRSLRLS
CAASGFTFSSYTMHWVRQAPGKGLEWVTFISYDGNNKYYADSVKGRFTISRDNSKNTLYLQM
NSLRAEDTAIYYCARTGWLGPFDYWGQGTLVTVSSASTKGPSVFPLAPSSKSTSGGTAALGC
LVKDYFPEPVTVSWNSGALTSGVHTFPAVLQSSGLYSLSSVVTVPSSSLGTQTYICNVNHKP
SNTKVDKRVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPG

Amino acid sequence of Anti-CTLA4 LC constant-PD1 fusion protein: SEQ ID NO: 33

EIVLTQSPGTLSLSPGERATLSCRASQSVGSSYLAWYQQKPGQAPRLLIYGAFSRATGIPDR
FSGSGSGTDFTLTISRLEPEDFAVYYCQQYGSSPWTFGQGTKVEIKRTVAAPSVFIFPPSDE
QLKSGTASVVCLLNNFYPREAKVQWKVDNALQSGNSQESVTEQDSKDSTYSLSSTLTLSKAD
YEKHKVYACEVTHQGLSSPVTKSFNRGECGGGGSGGGGSGGGGSPGWFLDSPDRPWNPPTFS
PALLVVTEGDNATFTCSFSNTSESFVLNWYRMSPSNQTDKLAAFPEDRSQPGQDCRFRVTQL
PNGRDFHMSVVRARRNDSGTYLCGAISLAPKAQIKESLRAELRVTERRAEVPTAHPSPSRP
AGQFQTLV

Figure 31

20. Anti-CTLA4-PD1(HC-N-terminus & LC- N-terminus):

Amino acid sequence of PD1-Anti-CTLA4 HC variable fusion protein:SEQ ID NO: 34

PGWFLDSPDRPWNPPTFSPALLVVTEGDNATFTCSFSNTSESFVLNWYRMSPSNQTDKLAAF
PEDRSQPGQDCRFRVTQLPNGRDFHMSVVRARRNDSGTYLCGAISLAPKAQIKESLRAELRV
TERRAEVPTAHPSPSPRPAGQFQTLVGGGGSGGGGSGGGGSQVQLVESGGGVVQPGRSLRLS
CAASGFTFSSYTMHWVRQAPGKGLEWVTFISYDGNNKYYADSVKGRFTISRDNSKNTLYLQM
NSLRAEDTAIYYCARTGWLGPFDYWGQGTLVTVSSASTKGPSVFPLAPSSKSTSGGTAALGC
LVKDYFPEPVTVSWNSGALTSGVHTFPAVLQSSGLYSLSSVVTVPSSSLGTQTYICNVNHKP
SNTKVDKRVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPG

Amino acid sequence of PD1-Anti-CTLA4 LC variable fusion protein: SEQ ID NO: 35

PGWFLDSPDRPWNPPTFSPALLVVTEGDNATFTCSFSNTSESFVLNWYRMSPSNQTDKLAAF
PEDRSQPGQDCRFRVTQLPNGRDFHMSVVRARRNDSGTYLCGAISLAPKAQIKESLRAELRV
TERRAEVPTAHPSPSPRPAGQFQTLVGGGGSGGGGSGGGGSEIVLTQSPGTLSLSPGERATL
SCRASQSVGSSYLAWYQQKPGQAPRLLIYGAFSRATGIPDRFSGSGSGTDFTLTISRLEPED
FAVYYCQQYGSSPWTFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVT
KSFNRGEC

Figure 32

SEQUENCE LISTING

```
<160> NUMBER OF SEQ ID NOS: 35

<210> SEQ ID NO 1
<211> LENGTH: 1344
<212> TYPE: DNA
<213> ORGANISM: Artificial Sequence
<220> FEATURE:
<223> OTHER INFORMATION: Synthetic Construct

<400> SEQUENCE: 1
caggtgcagc tgaagcagtc tggccctggc ctggtgcagc cctcccagtc cctgtccatc      60
acctgtaccg tgtccggctt ctccctgacc aactacggcg tgcactgggt gcgacagtcc     120
cccggcaagg gcctggaatg gctgggagtg atttggagcg gcggcaacac cgactacaac     180
acccccttca cctcccggct gtccatcaac aaggacaact ccaagtccca ggtgttcttc     240
aagatgaact ccctgcagtc caacgacacc gccatctact actgcgccag agccctgacc     300
tactatgact acgagttcgc ctactggggc cagggcaccc tggtgacagt gtccgccgct     360
tccaccaagg gcccctccgt gttccctctg gcccctcca gcaagtccac ctctggcggc     420
accgctgccc tgggctgcct ggtgaaagac tacttccccg agcccgtgac cgtgtcctgg     480
aactctggcg ccctgacctc cggcgtgcac accttccctg ccgtgctgca gtcctccggc     540
ctgtactccc tgtcctccgt ggtgaccgtg ccctccagct ctctgggcac ccagacctac     600
atctgcaacg tgaaccacaa gccctccaac accaaggtgg acaagcgggt ggaacccaag     660
tcctgcgaca gacccacac ctgtcccccc tgccctgccc ctgaactgct gggcggacct     720
tccgtgttcc tgttccccccc aaagcccaag gacaccctga tgatctcccg gacccccgaa     780
gtgacctgcg tggtggtgga cgtgtcccac gaggaccctg aagtgaagtt caattggtac     840
gtggacggcg tggaagtgca caacgccaag accaagccca gagaggaaca gtacaactcc     900
acctaccggg tggtgtctgt gctgaccgtg ctgcaccagg actggctgaa cggcaaagag     960
tacaagtgca aggtgtccaa caaggccctg cctgccccca tcgaaaagac catctccaag    1020
```

| gccaagggcc agccccgcga gccccaggtg tacaccctgc cccctagccg ggacgagctg | 1080 |
| accaagaacc aggtgtccct gacctgtctg gtgaaaggct tctacccctc cgatatcgcc | 1140 |
| gtggaatggg agtccaacgg ccagcccgag aacaactaca agaccacccc ccctgtgctg | 1200 |
| gactccgacg gctcattctt cctgtactcc aagctgaccg tggacaagtc ccggtggcag | 1260 |
| cagggcaacg tgttctcctg ctccgtgatg cacgaggccc tgcacaacca ctacacccag | 1320 |
| aagtccctgt ctctgtcccc cggc | 1344 |

```
<210> SEQ ID NO 2
<211> LENGTH: 642
<212> TYPE: DNA
<213> ORGANISM: Artificial Sequence
<220> FEATURE:
<223> OTHER INFORMATION: Synthetic Construct

<400> SEQUENCE: 2
```

| gacatcctgc tgacccagtc ccccgtgatc ctgtccgtgt ctcctggcga gcgggtgtcc | 60 |
| ttctcctgcc gggcctctca gtccatcggc accaacatcc actggtatca gcagcggacc | 120 |
| aacggctccc ctcggctgct gattaagtac gcctccgagt ccatctccgg catcccttcc | 180 |
| cggttctccg gctccggctc tggcaccgac ttcaccctgt ccatcaactc cgtggaatcc | 240 |
| gaggacattg ccgactacta ctgccagcag aacaacaact ggcccaccac cttcggcgct | 300 |
| ggcaccaagc tggaactgaa gcggaccgtg gccgctccct ccgtgttcat cttcccaccc | 360 |
| tccgacgagc agctgaagtc cggcaccgcc tccgtggtgt gcctgctgaa caacttctac | 420 |
| ccccgcgagg ccaaggtgca gtggaaggtg gacaacgccc tgcagtccgg caactcccag | 480 |
| gaatccgtga ccgagcagga ctccaaggac agcacctact ccctgtcctc cacccctgacc | 540 |
| ctgtccaagg ccgactacga aagcacaag gtgtacgcct gcgaagtgac ccaccagggc | 600 |
| ctgtccagcc ccgtgaccaa gtccttcaac cggggcgagt gt | 642 |

```
<210> SEQ ID NO 3
<211> LENGTH: 411
<212> TYPE: DNA
<213> ORGANISM: Artificial Sequence
<220> FEATURE:
<223> OTHER INFORMATION: Synthetic Construct

<400> SEQUENCE: 3
```

| acaatccctc cacacgtgca gaaatccgtg aacaacgaca tgatcgtgac cgacaacaat | 60 |
| ggcgccgtga gttcccccca gctgtgcaag ttctgcgacg tgcggttctc tacctgcgac | 120 |
| aaccagaaat cctgcatgtc caactgctcc atcacctcca tctgcgagaa gccccaggaa | 180 |
| gtgtgcgtgg ccgtgtggcg gaagaacgac gagaacatca ccctggaaac cgtgtgccac | 240 |
| gacccccaagc tgcctaccca cgacttcatc ctggaagatg ccgcctcccc caagtgcatc | 300 |
| atgaaggaaa agaagaagcc cggcgagact ttcttcatgt gcagctgctc ctccgacgag | 360 |
| tgcaacgaca acatcatctt ctccgaagag tacaacacct ccaaccccga c | 411 |

```
<210> SEQ ID NO 4
<211> LENGTH: 45
<212> TYPE: DNA
<213> ORGANISM: Artificial Sequence
<220> FEATURE:
<223> OTHER INFORMATION: Synthetic Construct

<400> SEQUENCE: 4
```
ggaggcggag gatctggcgg aggtggaagt ggcggcggag gctct         45

<210> SEQ ID NO 5
<211> LENGTH: 1341
<212> TYPE: DNA
<213> ORGANISM: Artificial Sequence
<220> FEATURE:
<223> OTHER INFORMATION: Synthetic Construct

<400> SEQUENCE: 5

```
caggtgcagc tggtggaatc tggtggcgga gtggtgcagc tggcagatcc cctgagactg    60
tcttgtgccg cctccggctt caccttctcc tcgtacacca tgcactgggt gcgacaggcc   120
cctggcaagg gactggaatg ggtcaccttc atctcttacg acggcaacaa caagtactac   180
gccgactccg tgaagggccg gttcaccatc tcccggaca actccaagaa caccctgtac    240
ctgcagatga actccctgcg ggccgaggac accgccatct actactgtgc tagaaccggc   300
tggctgggcc cctccgatta ttggggccag ggcaccctcg tgaccgtctc gagcgctagc   360
acaaagggcc ctagtgtgtt tcctctggct ccctcttcca atccacttc tggtggcact    420
gctgctctgg gatgcctggt gaaggattac tttcctgaac ctgtgactgt ctcatggaac   480
tctggtgctc tgacttctgg tgtccacact ttccctgctg tgctgcagtc tagtggactg   540
tactctctgt catctgtggt cactgtgccc tcttcatctc tgggaaccca gacctacatt   600
tgtaatgtga accacaaacc atccaacact aaagtggaca acgggtggga acccaaatcc    660
tgtgacaaaa cccacacctg cccaccttgt cctgcccctg aactgctggg aggaccttct   720
gtgtttctgt tccccccaa accaaggat accctgatga tctctagaac ccctgaggtg     780
acatgtgtgg tggtggatgt gtctcatgag accctgagg tcaaattcaa ctggtacgtg    840
gatggagtgg aagtccacaa tgccaaaacc aagcctagag aggaacagta caattcaacc   900
tacagagtgg tcagtgtgct gactgtgctg catcaggatt ggctgaatgg caaggaatac   960
aagtgtaaag tctcaaacaa ggccctgcct gctccaattg agaaaacaat ctcaaaggcc  1020
aagggacagc ctagggaacc ccaggtctac accctgccac cttcaagaga tgaactgacc  1080
aaaaaccagg tgtccctgac atgcctggtc aaaggcttct acccttctga cattgctgtg  1140
gagtgggagt caaatggaca gcctgagaac aactacaaaa caacccccc tgtgctggat   1200
tctgatggct ctttctttct gtactccaaa ctgactgtgg acaagtctag atggcagcag  1260
gggaatgtct tttcttgctc tgtcatgcat gaggctctgc ataaccacta cactcagaaa  1320
tccctgtctc tgtctcccgg g                                            1341
```

<210> SEQ ID NO 6
<211> LENGTH: 645
<212> TYPE: DNA
<213> ORGANISM: Artificial Sequence
<220> FEATURE:
<223> OTHER INFORMATION: Synthetic Construct

<400> SEQUENCE: 6

```
gagatcgtgc tgacccagtc tcctggcacc ctgtctctga gccctggcga gagagctacc    60
ctgtcctgca gagcctctca gtccgtgggc tcctcttacc tggcctggta tcaacaaaaa   120
cccggccaag ctccccggct gctgatctac ggtgcctttt ctcgcgccac cggcatcccc   180
gaccggttct ccggatctgg ctctggcacc gacttcaccc tgaccatctc ccggctggaa   240
cccgaggact tcgccgtgta ctactgccag cagtacggct cctcccctg gacctttggc    300
cagggcacca aggtggaaat caaacgtacg gtcgcggcgc cttccgtgtt catcttccca   360
```

```
cctctccgacg agcagctgaa gtccggcacc gcctccgtgg tgtgcctgct gaacaacttc    420
tacccccgcg aggccaaggt gcagtggaag gtggacaacg ccctgcagtc cggcaactcc    480
caggaatccg tgaccgagca ggactccaag acagcacct actccctgtc ctccaccctg    540
accctgtcca aggccgacta cgagaagcac aaggtgtacg cctgcgaagt gacccaccag    600
ggcctgtcca gccccgtgac caagtccttc aaccggggcg agtgt                   645
```

```
<210> SEQ ID NO 7
<211> LENGTH: 450
<212> TYPE: DNA
<213> ORGANISM: Artificial Sequence
<220> FEATURE:
<223> OTHER INFORMATION: Synthetic Construct

<400> SEQUENCE: 7
cctggctggt ttctggactc ccctgaccgg ccctggaacc cccaaccttt ctctcctgcc     60
ctgctggtgg tgacagaggg cgacaacgcc accttcacct gttccttcag caacacctcc    120
gagtccttcg tgctgaactg gtacagaatg tcccccagca accagaccga caagctggcc    180
gccttccccg aggacagatc ccagcctggc caggactgcc ggttcagagt gacccagctg    240
cccaacggcc gggacttcca catgtccgtg gtgcgagcca gacggaacga ctccggcacc    300
tacctgtgcg cgccatctc tctggccccc aaggcccaga tcaaagagtc cctgcgggcc    360
gagctgagag tgaccgagag aagggccgag gtgcccaccg cccacccctag cccatctcca    420 agacctgccg gccagttcca gaccctggtg                                      450
```

```
<210> SEQ ID NO 8
<211> LENGTH: 448
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 9
<211> LENGTH: 214
<212> TYPE: PRT
<213> ORGANISM: Artificial Sequence
<220> FEATURE:
<223> OTHER INFORMATION: Synthetic Construct

<400> SEQUENCE: 9

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

```
Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 10
<211> LENGTH: 15
<212> TYPE: PRT
<213> ORGANISM: Artificial Sequence
<220> FEATURE:
<223> OTHER INFORMATION: Synthetic Construct

<400> SEQUENCE: 10

Gly Gly Gly Gly Ser Gly Gly Gly Ser Gly Gly Gly Gly Ser
1               5                   10                  15

<210> SEQ ID NO 11
<211> LENGTH: 150
<212> TYPE: PRT
<213> ORGANISM: Artificial Sequence
<220> FEATURE:
<223> OTHER INFORMATION: Synthetic Construct

<400> SEQUENCE: 11

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
            130                 135                 140

Gln Phe Gln Thr Leu Val
145                 150
```

```
<210> SEQ ID NO 12
<211> LENGTH: 137
<212> TYPE: PRT
<213> ORGANISM: Artificial Sequence
<220> FEATURE:
<223> OTHER INFORMATION: Synthetic Construct

<400> SEQUENCE: 12

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
                20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
        50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135

<210> SEQ ID NO 13
<211> LENGTH: 447
<212> TYPE: PRT
<213> ORGANISM: Artificial Sequence
<220> FEATURE:
<223> OTHER INFORMATION: Synthetic Construct

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

-continued

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 14
<211> LENGTH: 215
<212> TYPE: PRT
<213> ORGANISM: Artificial Sequence
<220> FEATURE:
<223> OTHER INFORMATION: Synthetic Construct

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

-continued

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 15
<211> LENGTH: 613
<212> TYPE: PRT
<213> ORGANISM: Artificial Sequence
<220> FEATURE:
<223> OTHER INFORMATION: Synthetic Construct

<400> SEQUENCE: 15

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Gly Ser Gly Gly Gly Gly Ser Gly Gly Gly Gly Ser Pro
    450                 455                 460

Gly Trp Phe Leu Asp Ser Pro Asp Arg Pro Trp Asn Pro Pro Thr Phe
465                 470                 475                 480

Ser Pro Ala Leu Leu Val Val Thr Glu Gly Asp Asn Ala Thr Phe Thr
                485                 490                 495

Cys Ser Phe Ser Asn Thr Ser Glu Ser Phe Val Leu Asn Trp Tyr Arg
            500                 505                 510

Met Ser Pro Ser Asn Gln Thr Asp Lys Leu Ala Ala Phe Pro Glu Asp
        515                 520                 525

Arg Ser Gln Pro Gly Gln Asp Cys Arg Phe Arg Val Thr Gln Leu Pro
    530                 535                 540

Asn Gly Arg Asp Phe His Met Ser Val Val Arg Ala Arg Arg Asn Asp
545                 550                 555                 560

Ser Gly Thr Tyr Leu Cys Gly Ala Ile Ser Leu Ala Pro Lys Ala Gln
                565                 570                 575

Ile Lys Glu Ser Leu Arg Ala Glu Leu Arg Val Thr Glu Arg Arg Ala
            580                 585                 590

Glu Val Pro Thr Ala His Pro Ser Pro Ser Pro Arg Pro Ala Gly Gln
        595                 600                 605

Phe Gln Thr Leu Val
    610

<210> SEQ ID NO 16
<211> LENGTH: 379
<212> TYPE: PRT
<213> ORGANISM: Artificial Sequence
<220> FEATURE:
<223> OTHER INFORMATION: Synthetic Construct
```

<400> SEQUENCE: 16

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Ser
210                 215                 220

Gly Gly Gly Gly Ser Pro Gly Trp Phe Leu Asp Ser Pro Asp Arg Pro
225                 230                 235                 240

Trp Asn Pro Pro Thr Phe Ser Pro Ala Leu Leu Val Val Thr Glu Gly
                245                 250                 255

Asp Asn Ala Thr Phe Thr Cys Ser Phe Ser Asn Thr Ser Glu Ser Phe
            260                 265                 270

Val Leu Asn Trp Tyr Arg Met Ser Pro Ser Asn Gln Thr Asp Lys Leu
        275                 280                 285

Ala Ala Phe Pro Glu Asp Arg Ser Gln Pro Gly Gln Asp Cys Arg Phe
    290                 295                 300

Arg Val Thr Gln Leu Pro Asn Gly Arg Asp Phe His Met Ser Val Val
305                 310                 315                 320

Arg Ala Arg Arg Asn Asp Ser Gly Thr Tyr Leu Cys Gly Ala Ile Ser
                325                 330                 335

Leu Ala Pro Lys Ala Gln Ile Lys Glu Ser Leu Arg Ala Glu Leu Arg
            340                 345                 350

Val Thr Glu Arg Arg Ala Glu Val Pro Thr Ala His Pro Ser Pro Ser
        355                 360                 365

Pro Arg Pro Ala Gly Gln Phe Gln Thr Leu Val
    370                 375
```

<210> SEQ ID NO 17
<211> LENGTH: 613
<212> TYPE: PRT

<213> ORGANISM: Artificial Sequence
<220> FEATURE:
<223> OTHER INFORMATION: Synthetic Construct

<400> SEQUENCE: 17

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Gly Gly Ser Gly Gly Gly Gly Ser
145                 150                 155                 160

Gly Gly Gly Gly Ser Gln Val Gln Leu Lys Gln Ser Gly Pro Gly Leu
                165                 170                 175

Val Gln Pro Ser Gln Ser Leu Ser Ile Thr Cys Thr Val Ser Gly Phe
            180                 185                 190

Ser Leu Thr Asn Tyr Gly Val His Trp Val Arg Gln Ser Pro Gly Lys
        195                 200                 205

Gly Leu Glu Trp Leu Gly Val Ile Trp Ser Gly Gly Asn Thr Asp Tyr
    210                 215                 220

Asn Thr Pro Phe Thr Ser Arg Leu Ser Ile Asn Lys Asp Asn Ser Lys
225                 230                 235                 240

Ser Gln Val Phe Phe Lys Met Asn Ser Leu Gln Ser Asn Asp Thr Ala
                245                 250                 255

Ile Tyr Tyr Cys Ala Arg Ala Leu Thr Tyr Tyr Asp Tyr Glu Phe Ala
            260                 265                 270

Tyr Trp Gly Gln Gly Thr Leu Val Thr Val Ser Ala Ala Ser Thr Lys
        275                 280                 285

Gly Pro Ser Val Phe Pro Leu Ala Pro Ser Ser Lys Ser Thr Ser Gly
    290                 295                 300

Gly Thr Ala Ala Leu Gly Cys Leu Val Lys Asp Tyr Phe Pro Glu Pro
305                 310                 315                 320

Val Thr Val Ser Trp Asn Ser Gly Ala Leu Thr Ser Gly Val His Thr
                325                 330                 335

Phe Pro Ala Val Leu Gln Ser Ser Gly Leu Tyr Ser Leu Ser Ser Val
            340                 345                 350

Val Thr Val Pro Ser Ser Ser Leu Gly Thr Gln Thr Tyr Ile Cys Asn
        355                 360                 365

Val Asn His Lys Pro Ser Asn Thr Lys Val Asp Lys Arg Val Glu Pro
    370                 375                 380

Lys Ser Cys Asp Lys Thr His Thr Cys Pro Pro Cys Pro Ala Pro Glu
```

```
385                 390                 395                 400
Leu Leu Gly Gly Pro Ser Val Phe Leu Phe Pro Pro Lys Pro Lys Asp
                405                 410                 415

Thr Leu Met Ile Ser Arg Thr Pro Glu Val Thr Cys Val Val Val Asp
                420                 425                 430

Val Ser His Glu Asp Pro Glu Val Lys Phe Asn Trp Tyr Val Asp Gly
                435                 440                 445

Val Glu Val His Asn Ala Lys Thr Lys Pro Arg Glu Glu Gln Tyr Asn
        450                 455                 460

Ser Thr Tyr Arg Val Val Ser Val Leu Thr Val Leu His Gln Asp Trp
465                 470                 475                 480

Leu Asn Gly Lys Glu Tyr Lys Cys Lys Val Ser Asn Lys Ala Leu Pro
                485                 490                 495

Ala Pro Ile Glu Lys Thr Ile Ser Lys Ala Lys Gly Gln Pro Arg Glu
                500                 505                 510

Pro Gln Val Tyr Thr Leu Pro Pro Ser Arg Asp Glu Leu Thr Lys Asn
            515                 520                 525

Gln Val Ser Leu Thr Cys Leu Val Lys Gly Phe Tyr Pro Ser Asp Ile
        530                 535                 540

Ala Val Glu Trp Glu Ser Asn Gly Gln Pro Glu Asn Asn Tyr Lys Thr
545                 550                 555                 560

Thr Pro Pro Val Leu Asp Ser Asp Gly Ser Phe Phe Leu Tyr Ser Lys
                565                 570                 575

Leu Thr Val Asp Lys Ser Arg Trp Gln Gln Gly Asn Val Phe Ser Cys
                580                 585                 590

Ser Val Met His Glu Ala Leu His Asn His Tyr Thr Gln Lys Ser Leu
            595                 600                 605

Ser Leu Ser Pro Gly
        610

<210> SEQ ID NO 18
<211> LENGTH: 379
<212> TYPE: PRT
<213> ORGANISM: Artificial Sequence
<220> FEATURE:
<223> OTHER INFORMATION: Synthetic Construct

<400> SEQUENCE: 18

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
```

```
                    130                 135                 140
Gln Phe Gln Thr Leu Val Gly Gly Gly Ser Gly Gly Gly Gly Ser
145                 150                 155                 160

Gly Gly Gly Gly Ser Asp Ile Leu Leu Thr Gln Ser Pro Val Ile Leu
                165                 170                 175

Ser Val Ser Pro Gly Glu Arg Val Ser Phe Ser Cys Arg Ala Ser Gln
            180                 185                 190

Ser Ile Gly Thr Asn Ile His Trp Tyr Gln Gln Arg Thr Asn Gly Ser
        195                 200                 205

Pro Arg Leu Leu Ile Lys Tyr Ala Ser Glu Ser Ile Ser Gly Ile Pro
210                 215                 220

Ser Arg Phe Ser Gly Ser Gly Ser Gly Thr Asp Phe Thr Leu Ser Ile
225                 230                 235                 240

Asn Ser Val Glu Ser Glu Asp Ile Ala Asp Tyr Tyr Cys Gln Gln Asn
                245                 250                 255

Asn Asn Trp Pro Thr Thr Phe Gly Ala Gly Thr Lys Leu Glu Leu Lys
            260                 265                 270

Arg Thr Val Ala Ala Pro Ser Val Phe Ile Phe Pro Pro Ser Asp Glu
        275                 280                 285

Gln Leu Lys Ser Gly Thr Ala Ser Val Val Cys Leu Leu Asn Asn Phe
290                 295                 300

Tyr Pro Arg Glu Ala Lys Val Gln Trp Lys Val Asp Asn Ala Leu Gln
305                 310                 315                 320

Ser Gly Asn Ser Gln Glu Ser Val Thr Glu Gln Asp Ser Lys Asp Ser
                325                 330                 335

Thr Tyr Ser Leu Ser Ser Thr Leu Thr Leu Ser Lys Ala Asp Tyr Glu
            340                 345                 350

Lys His Lys Val Tyr Ala Cys Glu Val Thr His Gln Gly Leu Ser Ser
        355                 360                 365

Pro Val Thr Lys Ser Phe Asn Arg Gly Glu Cys
370                 375

<210> SEQ ID NO 19
<211> LENGTH: 28
<212> TYPE: DNA
<213> ORGANISM: Artificial Sequence
<220> FEATURE:
<223> OTHER INFORMATION: Synthetic Construct

<400> SEQUENCE: 19
agatatcgcc accatgatgt ccttcgtg                                28

<210> SEQ ID NO 20
<211> LENGTH: 35
<212> TYPE: DNA
<213> ORGANISM: Artificial Sequence
<220> FEATURE:
<223> OTHER INFORMATION: Synthetic Construct

<400> SEQUENCE: 20
ggcggcggag gctctcaggt gcagctgaag cagtc                        35

<210> SEQ ID NO 21
<211> LENGTH: 25
<212> TYPE: DNA
<213> ORGANISM: Artificial Sequence
<220> FEATURE:
<223> OTHER INFORMATION: Synthetic Construct
```

<400> SEQUENCE: 21
agtatactca gccggggac agaga          25

<210> SEQ ID NO 22
<211> LENGTH: 34
<212> TYPE: DNA
<213> ORGANISM: Artificial Sequence
<220> FEATURE:
<223> OTHER INFORMATION: Synthetic Construct

<400> SEQUENCE: 22
ttcagctgca cctgagagcc tccgccgcca cttc          34

<210> SEQ ID NO 23
<211> LENGTH: 35
<212> TYPE: DNA
<213> ORGANISM: Artificial Sequence
<220> FEATURE:
<223> OTHER INFORMATION: Synthetic Construct

<400> SEQUENCE: 23
attaattaat caacactcgc cccggttgaa ggact          35

<210> SEQ ID NO 24
<211> LENGTH: 35
<212> TYPE: DNA
<213> ORGANISM: Artificial Sequence
<220> FEATURE:
<223> OTHER INFORMATION: Synthetic Construct

<400> SEQUENCE: 24
ctctgtcccc cggcggcggc ggaggatctg gcgga          35

<210> SEQ ID NO 25
<211> LENGTH: 35
<212> TYPE: DNA
<213> ORGANISM: Artificial Sequence
<220> FEATURE:
<223> OTHER INFORMATION: Synthetic Construct

<400> SEQUENCE: 25
gatcctccgc cgccgccggg ggacagagac aggga          35

<210> SEQ ID NO 26
<211> LENGTH: 26
<212> TYPE: DNA
<213> ORGANISM: Artificial Sequence
<220> FEATURE:
<223> OTHER INFORMATION: Synthetic Construct

<400> SEQUENCE: 26
agtatactca caccagggtc tggaac          26

<210> SEQ ID NO 27
<211> LENGTH: 600
<212> TYPE: PRT
<213> ORGANISM: Artificial Sequence
<220> FEATURE:
<223> OTHER INFORMATION: Synthetic Construct

<400> SEQUENCE: 27

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

-continued

```
Gly Val His Trp Val Arg Gln Ser Pro Gly Lys Gly Leu Glu Trp Leu
         35                  40                  45
Gly Val Ile Trp Ser Gly Gly Asn Thr Asp Tyr Asn Thr Pro Phe Thr
 50                  55                  60
Ser Arg Leu Ser Ile Asn Lys Asp Asn Ser Lys Ser Gln Val Phe Phe
 65                  70                  75                  80
Lys Met Asn Ser Leu Gln Ser Asn Asp Thr Ala Ile Tyr Tyr Cys Ala
                 85                  90                  95
Arg Ala Leu Thr Tyr Tyr Asp Tyr Glu Phe Ala Tyr Trp Gly Gln Gly
                100                 105                 110
Thr Leu Val Thr Val Ser Ala Ala Ser Thr Lys Gly Pro Ser Val Phe
                115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
```

```
Gly Gly Gly Ser Gly Gly Gly Ser Gly Gly Gly Ser Thr
        450             455             460

Ile Pro Pro His Val Gln Lys Ser Val Asn Asn Asp Met Ile Val Thr
465             470             475             480

Asp Asn Asn Gly Ala Val Lys Phe Pro Gln Leu Cys Lys Phe Cys Asp
                485             490             495

Val Arg Phe Ser Thr Cys Asp Asn Gln Lys Ser Cys Met Ser Asn Cys
            500             505             510

Ser Ile Thr Ser Ile Cys Glu Lys Pro Gln Glu Val Cys Val Ala Val
        515             520             525

Trp Arg Lys Asn Asp Glu Asn Ile Thr Leu Glu Thr Val Cys His Asp
530             535             540

Pro Lys Leu Pro Tyr His Asp Phe Ile Leu Glu Asp Ala Ala Ser Pro
545             550             555             560

Lys Cys Ile Met Lys Glu Lys Lys Pro Gly Glu Thr Phe Phe Met
                565             570             575

Cys Ser Cys Ser Ser Asp Glu Cys Asn Asp Asn Ile Ile Phe Ser Glu
            580             585             590

Glu Tyr Asn Thr Ser Asn Pro Asp
        595             600

<210> SEQ ID NO 28
<211> LENGTH: 366
<212> TYPE: PRT
<213> ORGANISM: Artificial Sequence
<220> FEATURE:
<223> OTHER INFORMATION: Synthetic Construct

<400> SEQUENCE: 28

Asp Ile Leu Leu Thr Gln Ser Pro Val Ile Leu Ser Val Ser Pro Gly
1               5                  10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys Gly Gly Gly Ser Gly Gly Gly Ser
    210             215             220
Gly Gly Gly Gly Ser Thr Ile Pro Pro His Val Gln Lys Ser Val Asn
225             230             235             240
Asn Asp Met Ile Val Thr Asp Asn Gly Ala Val Lys Phe Pro Gln
            245             250             255
Leu Cys Lys Phe Cys Asp Val Arg Phe Ser Thr Cys Asp Asn Gln Lys
            260             265             270
Ser Cys Met Ser Asn Cys Ser Ile Thr Ser Ile Cys Glu Lys Pro Gln
        275             280             285
Glu Val Cys Val Ala Val Trp Arg Lys Asn Asp Glu Asn Ile Thr Leu
290             295             300
Glu Thr Val Cys His Asp Pro Lys Leu Pro Tyr His Asp Phe Ile Leu
305             310             315             320
Glu Asp Ala Ala Ser Pro Lys Cys Ile Met Lys Glu Lys Lys Pro
                325             330             335
Gly Glu Thr Phe Phe Met Cys Ser Cys Ser Ser Asp Glu Cys Asn Asp
            340             345             350
Asn Ile Ile Phe Ser Glu Glu Tyr Asn Thr Ser Asn Pro Asp
            355             360             365
```

<210> SEQ ID NO 29
<211> LENGTH: 600
<212> TYPE: PRT
<213> ORGANISM: Artificial Sequence
<220> FEATURE:
<223> OTHER INFORMATION: Synthetic Construct

<400> SEQUENCE: 29

```
Thr Ile Pro Pro His Val Gln Lys Ser Val Asn Asn Asp Met Ile Val
1               5               10              15
Thr Asp Asn Asn Gly Ala Val Lys Phe Pro Gln Leu Cys Lys Phe Cys
            20              25              30
Asp Val Arg Phe Ser Thr Cys Asp Asn Gln Lys Ser Cys Met Ser Asn
        35              40              45
Cys Ser Ile Thr Ser Ile Cys Glu Lys Pro Gln Glu Val Cys Val Ala
50              55              60
Val Trp Arg Lys Asn Asp Glu Asn Ile Thr Leu Glu Thr Val Cys His
65              70              75              80
Asp Pro Lys Leu Pro Tyr His Asp Phe Ile Leu Glu Asp Ala Ala Ser
            85              90              95
Pro Lys Cys Ile Met Lys Glu Lys Lys Pro Gly Glu Thr Phe Phe
        100             105             110
Met Cys Ser Cys Ser Ser Asp Glu Cys Asn Asp Asn Ile Ile Phe Ser
    115             120             125
Glu Glu Tyr Asn Thr Ser Asn Pro Asp Gly Gly Gly Ser Gly Gly
130             135             140
Gly Gly Ser Gly Gly Gly Ser Gln Val Gln Leu Lys Gln Ser Gly
145             150             155             160
Pro Gly Leu Val Gln Pro Ser Gln Ser Leu Ser Ile Thr Cys Thr Val
            165             170             175
Ser Gly Phe Ser Leu Thr Asn Tyr Gly Val His Trp Val Arg Gln Ser
        180             185             190
Pro Gly Lys Gly Leu Glu Trp Leu Gly Val Ile Trp Ser Gly Gly Asn
    195             200             205
```

```
Thr Asp Tyr Asn Thr Pro Phe Thr Ser Arg Leu Ser Ile Asn Lys Asp
    210                 215                 220

Asn Ser Lys Ser Gln Val Phe Phe Lys Met Asn Ser Leu Gln Ser Asn
225                 230                 235                 240

Asp Thr Ala Ile Tyr Tyr Cys Ala Arg Ala Leu Thr Tyr Tyr Asp Tyr
                245                 250                 255

Glu Phe Ala Tyr Trp Gly Gln Gly Thr Leu Val Thr Val Ser Ala Ala
                260                 265                 270

Ser Thr Lys Gly Pro Ser Val Phe Pro Leu Ala Pro Ser Ser Lys Ser
            275                 280                 285

Thr Ser Gly Gly Thr Ala Ala Leu Gly Cys Leu Val Lys Asp Tyr Phe
    290                 295                 300

Pro Glu Pro Val Thr Val Ser Trp Asn Ser Gly Ala Leu Thr Ser Gly
305                 310                 315                 320

Val His Thr Phe Pro Ala Val Leu Gln Ser Ser Gly Leu Tyr Ser Leu
                325                 330                 335

Ser Ser Val Val Thr Val Pro Ser Ser Ser Leu Gly Thr Gln Thr Tyr
                340                 345                 350

Ile Cys Asn Val Asn His Lys Pro Ser Asn Thr Lys Val Asp Lys Arg
            355                 360                 365

Val Glu Pro Lys Ser Cys Asp Lys Thr His Thr Cys Pro Pro Cys Pro
    370                 375                 380

Ala Pro Glu Leu Leu Gly Gly Pro Ser Val Phe Leu Phe Pro Pro Lys
385                 390                 395                 400

Pro Lys Asp Thr Leu Met Ile Ser Arg Thr Pro Glu Val Thr Cys Val
                405                 410                 415

Val Val Asp Val Ser His Glu Asp Pro Glu Val Lys Phe Asn Trp Tyr
                420                 425                 430

Val Asp Gly Val Glu Val His Asn Ala Lys Thr Lys Pro Arg Glu Glu
            435                 440                 445

Gln Tyr Asn Ser Thr Tyr Arg Val Val Ser Val Leu Thr Val Leu His
    450                 455                 460

Gln Asp Trp Leu Asn Gly Lys Glu Tyr Lys Cys Lys Val Ser Asn Lys
465                 470                 475                 480

Ala Leu Pro Ala Pro Ile Glu Lys Thr Ile Ser Lys Ala Lys Gly Gln
                485                 490                 495

Pro Arg Glu Pro Gln Val Tyr Thr Leu Pro Pro Ser Arg Asp Glu Leu
                500                 505                 510

Thr Lys Asn Gln Val Ser Leu Thr Cys Leu Val Lys Gly Phe Tyr Pro
            515                 520                 525

Ser Asp Ile Ala Val Glu Trp Glu Ser Asn Gly Gln Pro Glu Asn Asn
    530                 535                 540

Tyr Lys Thr Thr Pro Pro Val Leu Asp Ser Asp Gly Ser Phe Phe Leu
545                 550                 555                 560

Tyr Ser Lys Leu Thr Val Asp Lys Ser Arg Trp Gln Gln Gly Asn Val
                565                 570                 575

Phe Ser Cys Ser Val Met His Glu Ala Leu His Asn His Tyr Thr Gln
                580                 585                 590

Lys Ser Leu Ser Leu Ser Pro Gly
            595                 600

<210> SEQ ID NO 30
<211> LENGTH: 366
<212> TYPE: PRT
```

<213> ORGANISM: Artificial Sequence
<220> FEATURE:
<223> OTHER INFORMATION: Synthetic Construct

<400> SEQUENCE: 30

```
Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Gly Gly Gly Ser Gly Gly
            130                 135                 140

Gly Gly Ser Gly Gly Gly Ser Asp Ile Leu Leu Thr Gln Ser Pro
145                 150                 155                 160

Val Ile Leu Ser Val Ser Pro Gly Glu Arg Val Ser Phe Ser Cys Arg
                165                 170                 175

Ala Ser Gln Ser Ile Gly Thr Asn Ile His Trp Tyr Gln Gln Arg Thr
            180                 185                 190

Asn Gly Ser Pro Arg Leu Leu Ile Lys Tyr Ala Ser Glu Ser Ile Ser
            195                 200                 205

Gly Ile Pro Ser Arg Phe Ser Gly Ser Gly Ser Gly Thr Asp Phe Thr
    210                 215                 220

Leu Ser Ile Asn Ser Val Glu Ser Glu Asp Ile Ala Asp Tyr Tyr Cys
225                 230                 235                 240

Gln Gln Asn Asn Asn Trp Pro Thr Thr Phe Gly Ala Gly Thr Lys Leu
            245                 250                 255

Glu Leu Lys Arg Thr Val Ala Ala Pro Ser Val Phe Ile Phe Pro Pro
            260                 265                 270

Ser Asp Glu Gln Leu Lys Ser Gly Thr Ala Ser Val Val Cys Leu Leu
            275                 280                 285

Asn Asn Phe Tyr Pro Arg Glu Ala Lys Val Gln Trp Lys Val Asp Asn
            290                 295                 300

Ala Leu Gln Ser Gly Asn Ser Gln Glu Ser Val Thr Glu Gln Asp Ser
305                 310                 315                 320

Lys Asp Ser Thr Tyr Ser Leu Ser Ser Thr Leu Thr Leu Ser Lys Ala
            325                 330                 335

Asp Tyr Glu Lys His Lys Val Tyr Ala Cys Glu Val Thr His Gln Gly
            340                 345                 350

Leu Ser Ser Pro Val Thr Lys Ser Phe Asn Arg Gly Glu Cys
            355                 360                 365
```

<210> SEQ ID NO 31
<211> LENGTH: 600
<212> TYPE: PRT

<213> ORGANISM: Artificial Sequence
<220> FEATURE:
<223> OTHER INFORMATION: Synthetic Construct

<400> SEQUENCE: 31

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

```
            385                 390                 395                 400
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Gly Gly Gly Gly Ser Gly Gly Gly Ser Gly Gly Gly Ser Thr
        450                 455                 460

Ile Pro Pro His Val Gln Lys Ser Val Asn Asn Asp Met Ile Val Thr
465                 470                 475                 480

Asp Asn Asn Gly Ala Val Lys Phe Pro Gln Leu Cys Lys Phe Cys Asp
                485                 490                 495

Val Arg Phe Ser Thr Cys Asp Asn Gln Lys Ser Cys Met Ser Asn Cys
            500                 505                 510

Ser Ile Thr Ser Ile Cys Glu Lys Pro Gln Glu Val Cys Val Ala Val
            515                 520                 525

Trp Arg Lys Asn Asp Glu Asn Ile Thr Leu Glu Thr Val Cys His Asp
            530                 535                 540

Pro Lys Leu Pro Tyr His Asp Phe Ile Leu Glu Asp Ala Ala Ser Pro
545                 550                 555                 560

Lys Cys Ile Met Lys Glu Lys Lys Pro Gly Glu Thr Phe Phe Met
                565                 570                 575

Cys Ser Cys Ser Ser Asp Glu Cys Asn Asp Asn Ile Ile Phe Ser Glu
            580                 585                 590

Glu Tyr Asn Thr Ser Asn Pro Asp
        595                 600

<210> SEQ ID NO 32
<211> LENGTH: 612
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
```

```
            145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Arg Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
                290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Gly
                435                 440                 445
Gly Gly Gly Ser Gly Gly Gly Ser Gly Gly Gly Ser Pro Gly
                450                 455                 460
Trp Phe Leu Asp Ser Pro Asp Arg Pro Trp Asn Pro Pro Thr Phe Ser
465                 470                 475                 480
Pro Ala Leu Leu Val Val Thr Glu Gly Asp Asn Ala Thr Phe Thr Cys
                485                 490                 495
Ser Phe Ser Asn Thr Ser Glu Ser Phe Val Leu Asn Trp Tyr Arg Met
                500                 505                 510
Ser Pro Ser Asn Gln Thr Asp Lys Leu Ala Ala Phe Pro Glu Asp Arg
                515                 520                 525
Ser Gln Pro Gly Gln Asp Cys Arg Phe Arg Val Thr Gln Leu Pro Asn
                530                 535                 540
Gly Arg Asp Phe His Met Ser Val Val Arg Ala Arg Arg Asn Asp Ser
545                 550                 555                 560
Gly Thr Tyr Leu Cys Gly Ala Ile Ser Leu Ala Pro Lys Ala Gln Ile
                565                 570                 575
```

```
Lys Glu Ser Leu Arg Ala Glu Leu Arg Val Thr Glu Arg Ala Glu
            580                 585                 590

Val Pro Thr Ala His Pro Ser Pro Ser Pro Arg Pro Ala Gly Gln Phe
            595                 600                 605

Gln Thr Leu Val
    610

<210> SEQ ID NO 33
<211> LENGTH: 380
<212> TYPE: PRT
<213> ORGANISM: Artificial Sequence
<220> FEATURE:
<223> OTHER INFORMATION: Synthetic Construct

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Gly Gly Gly Gly
    210                 215                 220

Ser Gly Gly Gly Gly Ser Pro Gly Trp Phe Leu Asp Ser Pro Asp Arg
225                 230                 235                 240

Pro Trp Asn Pro Pro Thr Phe Ser Pro Ala Leu Leu Val Val Thr Glu
                245                 250                 255

Gly Asp Asn Ala Thr Phe Thr Cys Ser Phe Ser Asn Thr Ser Glu Ser
            260                 265                 270

Phe Val Leu Asn Trp Tyr Arg Met Ser Pro Ser Asn Gln Thr Asp Lys
        275                 280                 285

Leu Ala Ala Phe Pro Glu Asp Arg Ser Gln Pro Gly Gln Asp Cys Arg
    290                 295                 300

Phe Arg Val Thr Gln Leu Pro Asn Gly Arg Asp Phe His Met Ser Val
305                 310                 315                 320
```

```
Val Arg Ala Arg Arg Asn Asp Ser Gly Thr Tyr Leu Cys Gly Ala Ile
            325                 330                 335

Ser Leu Ala Pro Lys Ala Gln Ile Lys Glu Ser Leu Arg Ala Glu Leu
            340                 345                 350

Arg Val Thr Glu Arg Arg Ala Glu Val Pro Thr Ala His Pro Ser Pro
            355                 360                 365

Ser Pro Arg Pro Ala Gly Gln Phe Gln Thr Leu Val
    370                 375                 380

<210> SEQ ID NO 34
<211> LENGTH: 612
<212> TYPE: PRT
<213> ORGANISM: Artificial Sequence
<220> FEATURE:
<223> OTHER INFORMATION: Synthetic Construct

<400> SEQUENCE: 34

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Gly Gly Ser Gly Gly Gly Gly Ser
145                 150                 155                 160

Gly Gly Gly Gly Ser Gln Val Gln Leu Val Glu Ser Gly Gly Gly Val
                165                 170                 175

Val Gln Pro Gly Arg Ser Leu Arg Leu Ser Cys Ala Ala Ser Gly Phe
            180                 185                 190

Thr Phe Ser Ser Tyr Thr Met His Trp Val Arg Gln Ala Pro Gly Lys
        195                 200                 205

Gly Leu Glu Trp Val Thr Phe Ile Ser Tyr Asp Gly Asn Asn Lys Tyr
    210                 215                 220

Tyr Ala Asp Ser Val Lys Gly Arg Phe Thr Ile Ser Arg Asp Asn Ser
225                 230                 235                 240

Lys Asn Thr Leu Tyr Leu Gln Met Asn Ser Leu Arg Ala Glu Asp Thr
                245                 250                 255

Ala Ile Tyr Tyr Cys Ala Arg Thr Gly Trp Leu Gly Pro Phe Asp Tyr
            260                 265                 270

Trp Gly Gln Gly Thr Leu Val Thr Val Ser Ser Ala Ser Thr Lys Gly
        275                 280                 285

Pro Ser Val Phe Pro Leu Ala Pro Ser Ser Lys Ser Thr Ser Gly Gly
    290                 295                 300
```

Thr Ala Ala Leu Gly Cys Leu Val Lys Asp Tyr Phe Pro Glu Pro Val
305                 310                 315                 320

Thr Val Ser Trp Asn Ser Gly Ala Leu Thr Ser Gly Val His Thr Phe
            325                 330                 335

Pro Ala Val Leu Gln Ser Ser Gly Leu Tyr Ser Leu Ser Ser Val Val
        340                 345                 350

Thr Val Pro Ser Ser Ser Leu Gly Thr Gln Thr Tyr Ile Cys Asn Val
        355                 360                 365

Asn His Lys Pro Ser Asn Thr Lys Val Asp Lys Arg Val Glu Pro Lys
    370                 375                 380

Ser Cys Asp Lys Thr His Thr Cys Pro Pro Cys Pro Ala Pro Glu Leu
385                 390                 395                 400

Leu Gly Gly Pro Ser Val Phe Leu Phe Pro Pro Lys Pro Lys Asp Thr
            405                 410                 415

Leu Met Ile Ser Arg Thr Pro Glu Val Thr Cys Val Val Val Asp Val
        420                 425                 430

Ser His Glu Asp Pro Glu Val Lys Phe Asn Trp Tyr Val Asp Gly Val
        435                 440                 445

Glu Val His Asn Ala Lys Thr Lys Pro Arg Glu Glu Gln Tyr Asn Ser
    450                 455                 460

Thr Tyr Arg Val Val Ser Val Leu Thr Val Leu His Gln Asp Trp Leu
465                 470                 475                 480

Asn Gly Lys Glu Tyr Lys Cys Lys Val Ser Asn Lys Ala Leu Pro Ala
            485                 490                 495

Pro Ile Glu Lys Thr Ile Ser Lys Ala Lys Gly Gln Pro Arg Glu Pro
        500                 505                 510

Gln Val Tyr Thr Leu Pro Pro Ser Arg Asp Glu Leu Thr Lys Asn Gln
        515                 520                 525

Val Ser Leu Thr Cys Leu Val Lys Gly Phe Tyr Pro Ser Asp Ile Ala
530                 535                 540

Val Glu Trp Glu Ser Asn Gly Gln Pro Glu Asn Asn Tyr Lys Thr Thr
545                 550                 555                 560

Pro Pro Val Leu Asp Ser Asp Gly Ser Phe Phe Leu Tyr Ser Lys Leu
            565                 570                 575

Thr Val Asp Lys Ser Arg Trp Gln Gln Gly Asn Val Phe Ser Cys Ser
        580                 585                 590

Val Met His Glu Ala Leu His Asn His Tyr Thr Gln Lys Ser Leu Ser
        595                 600                 605

Leu Ser Pro Gly
    610

<210> SEQ ID NO 35
<211> LENGTH: 380
<212> TYPE: PRT
<213> ORGANISM: Artificial Sequence
<220> FEATURE:
<223> OTHER INFORMATION: Synthetic Construct

<400> SEQUENCE: 35

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

```
Arg Met Ser Pro Ser Asn Gln Thr Asp Lys Leu Ala Ala Phe Pro Glu
        50              55              60

Asp Arg Ser Gln Pro Gly Gln Asp Cys Arg Phe Arg Val Thr Gln Leu
65              70              75              80

Pro Asn Gly Arg Asp Phe His Met Ser Val Val Arg Ala Arg Arg Asn
                85              90              95

Asp Ser Gly Thr Tyr Leu Cys Gly Ala Ile Ser Leu Ala Pro Lys Ala
                100             105             110

Gln Ile Lys Glu Ser Leu Arg Ala Glu Leu Arg Val Thr Glu Arg Arg
        115             120             125

Ala Glu Val Pro Thr Ala His Pro Ser Pro Ser Pro Arg Pro Ala Gly
        130             135             140

Gln Phe Gln Thr Leu Val Gly Gly Gly Ser Gly Gly Gly Gly Gly Ser
145             150             155             160

Gly Gly Gly Gly Ser Glu Ile Val Leu Thr Gln Ser Pro Gly Thr Leu
                165             170             175

Ser Leu Ser Pro Gly Glu Arg Ala Thr Leu Ser Cys Arg Ala Ser Gln
                180             185             190

Ser Val Gly Ser Ser Tyr Leu Ala Trp Tyr Gln Gln Lys Pro Gly Gln
                195             200             205

Ala Pro Arg Leu Leu Ile Tyr Gly Ala Phe Ser Arg Ala Thr Gly Ile
        210             215             220

Pro Asp Arg Phe Ser Gly Ser Gly Ser Gly Thr Asp Phe Thr Leu Thr
225             230             235             240

Ile Ser Arg Leu Glu Pro Glu Asp Phe Ala Val Tyr Tyr Cys Gln Gln
                245             250             255

Tyr Gly Ser Ser Pro Trp Thr Phe Gly Gln Gly Thr Lys Val Glu Ile
                260             265             270

Lys Arg Thr Val Ala Ala Pro Ser Val Phe Ile Phe Pro Pro Ser Asp
        275             280             285

Glu Gln Leu Lys Ser Gly Thr Ala Ser Val Val Cys Leu Leu Asn Asn
        290             295             300

Phe Tyr Pro Arg Glu Ala Lys Val Gln Trp Lys Val Asp Asn Ala Leu
305             310             315             320

Gln Ser Gly Asn Ser Gln Glu Ser Val Thr Glu Gln Asp Ser Lys Asp
                325             330             335

Ser Thr Tyr Ser Leu Ser Ser Thr Leu Thr Leu Ser Lys Ala Asp Tyr
                340             345             350

Glu Lys His Lys Val Tyr Ala Cys Glu Val Thr His Gln Gly Leu Ser
        355             360             365

Ser Pro Val Thr Lys Ser Phe Asn Arg Gly Glu Cys
370             375             380
```

FUSION IMMUNOMODULATORY PROTEINS AND METHODS FOR MAKING SAME

CROSS REFERENCE TO RELATED APPLICATIONS

This application is a continuation application and claims priority to copending U.S. patent application Ser. No. 15/968,122 filed on May 1, 2018 and now U.S. Pat. No. 10,766,963, which in turn is a divisional and claims priority to copending U.S. patent application Ser. No. 14/771,308 filed on Aug. 28, 2015 and now U.S. Pat. No. 9,988,456 which was filed under the provisions of 35 U.S.C. § 371 and claims the priority of International Patent Application No. PCT/US2014/022404 filed on Mar. 10, 2014 which in turn claims priority to U.S. Provisional Patent Application No. 61/777,016 filed on Mar. 12, 2013 the contents of which are hereby incorporated by reference herein for all purposes.

SEQUENCE LISTING

The instant application contains a Sequence Listing which has been submitted in text format via EFS-Web and is hereby incorporated by reference in its entirety. Said text copy, created on Aug. 31, 2020, is named 650_147_CON_1014_ST25 and is 80,776 bytes in size.

BACKGROUND OF THE INVENTION

Technical Field

The present invention relates generally to the field of generating recombinant chimeric fusion proteins to be used in the cancer therapy, and more specifically, to fusion molecules of Anti-EGFR1-TGFβRII, Anti-EGFR1-PD1 and Anti-CTLA4-PD1 and methods of generating same, wherein the methods reduce production costs and increase homogeneity of the recombinant chimeric fusion proteins.

Related Art

In spite of numerous advances in medical research, cancer remains the second leading cause of death in the United States. Traditional modes of clinical care, such as surgical resection, radiotherapy and chemotherapy, have a significant failure rate, especially for solid tumors. Failure occurs either because the initial tumor is unresponsive, or because of recurrence due to regrowth at the original site or metastasis. Cancer remains a central focus for medical research and development.

Immunotherapy of cancer has been explored for over a century, but it is only in the last decade that various antibody-based products have been introduced into the management of patients with diverse forms of cancer. At present, this is one of the most active areas of clinical research, with numerous antibody therapeutic products already approved in oncology.

Using specific antibodies as therapeutic agents offers advantages over the non-targeted therapies such as systemic chemotherapy via oral or intravenous administration of drugs or radiation therapy. There are two types of antibody-based therapies. The more common type is to identify a tumor antigen (i.e., a protein expressed on tumors and cancer cells and not in normal tissues) and develop an antibody, preferably a monoclonal antibody (mAb) directed to the tumor antigen. One can then conjugate any therapeutic agent, such as a chemotherapeutic agent, a radionuclide, modified toxin, etc., to this antibody to achieve targeted therapy by the therapeutic agent to the tumor. The other kind of antibody based therapy is by providing an antibody which in itself has therapeutic properties against the tumor/cancer cells it targets. The added advantage of this second form of antibody-based therapy is that one may additionally conjugate another therapeutic agent to the therapeutic antibody to achieve a more effective treatment. The major advantage with any antibody-directed therapy and of therapy using monoclonal antibodies (mAbs) in particular, is the ability to deliver increased doses of a therapeutic agent to a tumor, with greater sparing of normal tissue from the side effects of the therapeutic agent.

Despite the identification of several antibodies for cancer therapies, there is still a need to identify new and more effective therapeutics to overcome immune tolerance and activate T cell responses. Further, even though molecular engineering has improved the prospects for such antibody-based therapeutics issues still remain regarding continuity in the generated recombinant products.

SUMMARY OF THE INVENTION

The present invention provides for a novel and consistent synthesis method for generating homogeneous recombinant fusion immunomodulatory molecules, and more specifically, recombinant chimeric polypeptides including targeting antibodies linked to immunomodulatory proteins.

To mediate an immune response against cancer, T cell activation and co-stimulation are both important. Co-stimulation of T cells is mainly mediated through engaging of CD28 with its ligands of B7 family on antigen presenting cells (APCs). However, after activation, T cells express a molecule called Cytotoxic T-Lymphocyte Antigen 4 (CTLA-4), which binds to B7 ligands with much more affinity than CD28 and such binding down-modulates T cell activity. Thus, including an antibody that binds to the CTLA-4 receptor would block interaction with ligands of the B7 family and enhance anti-tumor response.

Programmed Death Ligand-1 (PDL1), one of the B7 ligands discussed above, obstructs anti-tumor immunity by (i) tolerizing tumor-reactive T cells by binding to its receptor PD1 (CD279) on T cells; (ii) rendering tumor cells resistant to CD8+ T cell and FasL-mediated lysis by PD-1 signaling through tumor cell-expressed PDL1; and (iii) promoting the development and maintenance of induced T regulatory cells. Therefore, PDL1 is a major obstacle to natural anti-tumor immunity and to cancer immunotherapies requiring activation of host T cell-mediated anti-tumor immunity. This concept is supported by studies demonstrating that antibody blocking of PDL1-PD1 interactions improves T cell activation and reduces tumor progression. Although antibodies to PDL1 or PD1 have shown therapeutic efficacy in a subset of cancer patients, the majority of patients do not benefit from antibody treatment. Thus, there is needed a mechanism for regulating PD-L1 function that will lead to a new universally applicable treatment for minimizing PD-L1-mediated immune suppression in cancer patients and that is more effective than currently available mAbs to PD-1 or PD-L1.

A characteristic of many epithelial cancers, such as, cancers of the colon, head and neck, breast, ovary, non-small cell lung (NSCL), and pancreas, is abnormally high levels of epidermal growth factor receptor (EGFR) on the surface of cancer cells. The family of epidermal growth factor receptors (EGFR; HER1, HER2/neu, HER3, and HER4) includes cell membrane receptors with intrinsic tyrosine kinase activity that trigger a cascade of biophysiological signaling reactions in response to the binding of different ligands. These receptors play a key role in the behavior of malignant cells in a variety of human tumors, inducing increased proliferation, decreasing apoptosis, and enhancing tumor cell motility and angiogenesis. Thus, the present invention includes antibodies targeting EGFR family members.

The present invention further provides methods of reducing growth of cancer cells by counteracting immune tolerance of cancer cells, wherein T cells remain active and inhibit the recruitment of T-regulatory that are known to suppress the immune system's response to the tumor. Thus, the chimeric polypeptides generated by the polynucleotides sequences of the present invention are useful for treating cancer because of the expressed fusion or chimeric polypeptides.

In one aspect, the present invention provides for chimeric polypeptides containing at least one targeting moiety to target a cancer cell and at least one immunomodulating moiety that counteracts immune tolerance of cancer cell, wherein the targeting moiety and the immunomodulating moiety are linked by an amino acid spacer of sufficient length of amino acid residues so that both moieties can successfully bond to their individual target. In the alternative, the targeting moiety and the immunomodulating moiety that counteract immune tolerance of cancer cell may be bound directly to each other. The chimeric/fusion polypeptides of the invention are useful for binding to a cancer cell receptor and reducing the ability of cancer cells to avoid an immune response.

Preferably the targeting moiety is an antibody having binding affinity for CTLA-4 or EGFR1, wherein the antibody is transcribed from a polynucleotide sequence lacking nucleotides for expression of the C-terminal lysine of the heavy chain of the expressed antibody. It has been discovered that by removing the C-terminal lysine of the heavy chain of an antibody during transcription that the end product exhibits increased homogeneity, thereby reducing the need and costs for further purification.

It is known that during the process of transcription and translation of an IgG molecule in CHO cells, the lysine (K) at the C-terminal of the heavy chain will be expressed. In the commercial product such expressed lysines have to be removed to increase purity. There is much heterogeneity in the produced product, as shown in FIG. 1. This occurs because the CHO cell has an endogenous enzyme Carboxypeptidase B (CPB) which will cleave the C-terminal lysine as long as the expressed antibody is still available intracellularly. However, this enzyme will not cleave the lysine once the antibody is secreted into the medium. Thus, the cleavage efficiency of this endogenous CPB is based on the availability within the cell. As such, some of the antibodies will be secreted with the lysine and some will not, and such combination will cause significant heterogeneity in the secreted product, that being some antibodies with the C-terminal lysine and some without. As the recombinant product is being used for the therapeutic use, one needs to purify to homogeneity. Thus, the recombinant products of the prior art requires additional purification steps wherein the recombinant product need to be treated with the enzyme CPB first and purified once again using an additional step to remove any lysine and the enzyme CPB from the final product. These additional steps add a significant cost to the manufacturing process.

The present invention avoids the shortcomings of previous methods of synthesizing recombinant anti-CTLA-4 and anti-EGFR1 antibodies by transcribing an expressed protein from a polynucleotide sequence lacking nucleotides for expression of the C-terminal lysine at the heavy chain of the expressed antibody.

The present invention is based on preparing chimeric/fusion proteins by expression of polynucleotides encoding the fusion proteins that counteract or reverse immune tolerance of cancer cells. Cancer cells are able to escape elimination by chemotherapeutic agents or tumor-targeted antibodies via specific immunosuppressive mechanisms in the tumor microenvironment and such ability of cancer cells is recognized as immune tolerance. Such immunosuppressive mechanisms include immunosuppressive cytokines (for example, Transforming growth factor beta (TGF-β)) and regulatory T cells and/or immunosuppressive myeloid dendritic cells (DCs). By counteracting tumor-induced immune tolerance, the present invention provides effective compositions and methods for cancer treatment, optional in combination with another existing cancer treatment. The present invention provides strategies to counteract tumor-induced immune tolerance and enhance the antitumor efficacy of chemotherapy by activating and leveraging T cell-mediated adaptive antitumor against resistant or disseminated cancer cells.

In another aspect, the present invention provides a molecule including at least one targeting moiety fused with at least one immunomodulatory moiety. The targeting moiety specifically binds a target molecule, and the immunomodulatory moiety specifically binds one of the following molecules: (i) Transforming growth factor-beta (TGF-β) and or (ii) Programmed death-1 ligand 1 (PD-L1).

In a further aspect, the targeting moiety includes an antibody, including both heavy chains and light chains, wherein the antibody specifically binds a component of a tumor cell, tumor antigen, tumor vasculature, tumor microenvironment, or tumor-infiltrating immune cell. Notably the heavy chain and/or light chain may individually be linked to a same type immunomodulatory moiety or a separate and distinct immunomodulatory moiety. Further, a heavy or light chain of an antibody targeting moiety may be linked to an immunomodulatory moiety which in turn can be further linked to a second immunomodulatory moiety wherein there is a linker between the two immunomodulatory moieties.

In a still further aspect, there is provided a chimeric polypeptide that comprised a tumor targeting moiety and an immunomodulatory moiety comprising a molecule that binds transforming growth factor beta (TGF-β), wherein the tumor targeting moiety is an antibody that binds to EGFR1, where in the antibody can be the full antibody, heavy chain or light chain.

The tumor targeting moiety may include monoclonal antibodies that target a cancer cell, including but not limited to cetuximab, trastuzumab, ritubximab, ipilimumab, tremelimumab, muromonab-CD3, abciximab, daclizumab, basiliximab, palivizumab, infliximab. gemtuzumab ozogamicin, alemtuzumab, ibritumomab tiuxetan, adalimumab, omalizumab, tositumomab, 1-131 tositumomab, efalizumab, bevacizumab, panitumumab, pertuzumab, natalizumab, etanercept, IGN101 (Aphton), voloximab (Biogen Idec and PDL BioPharm), Anti-CD80 mAb (Biogen Idec), Anti-CD23 mAb (Biogen Idel), CAT-3888 (Cambridge Antibody Technology), CDP-791 (Imclone), eraptuzumab (Immunomedics), MDX-010 (Medarex and BMS), MDX-060 (Medarex), MDX-070 (Medarex), matuzumab (Merck), CP-675, 206 (Pfizer), CAL (Roche), SGN-30 (Seattle Genetics), zanolimumab (Serono and Genmab), adecatumumab (Sereno), oregovomab (United Therapeutics), nimotuzumab (YM Bioscience), ABT-874 (Abbott Laboratories), denosumab (Amgen), AM 108 (Amgen), AMG 714 (Amgen), fontolizumab (Biogen Idec and PDL BioPharm), daclizumab (Biogent Idec and PDL BioPharm), golimumab (Centocor and Schering-Plough), CNTO 1275 (Centocor), ocrelizumab (Genetech and Roche), HuMax-CD20 (Genmab), belimumab (HGS and GSK), epratuzumab (Immunomedics), MLN1202 (Millennium Pharmaceuticals), visilizumab (PDL BioPharm), tocilizumab (Roche), ocrerlizumab (Roche), certolizumab pegol (UCB, formerly Celltech), eculizumab (Alexion Pharmaceuticals), pexelizumab (Alexion Pharmaceuticals and Procter & Gamble), abciximab (Centocor), ranibizimumab (Genetech), mepolizumab (GSK), TNX-355 (Tanox), or MYO-029 (Wyeth).

In a preferred embodiment, the tumor targeting moiety is a monoclonal antibody that binds to CTLA-4 or EGFR1 generated by the methods of the present invention, wherein the method comprises the following steps:

a. preparing a codon optimized nucleotide sequence encoding the fusion protein, wherein the codon optimized sequence for the antibody is lacking nucleotides for expression of a lysine at the C-terminal end of the heavy chains of the antibody;
b. cloning the optimized sequence of said fusion protein in a host cell capable of transient or continued expression;
c. growing the host cell in a media under suitable conditions for growing and allowing the host cell to express the fusion protein; and
d. collecting secreted fusion proteins.

In yet another aspect, the immunomodulatory moiety includes a molecule that binds TGF-β and inhibits the function thereof. Specifically the immunomodulatory moiety includes an extracellular ligand-binding domain of Transforming growth factor-beta receptor TGF-βRII, TGF-βRIIb or TGF-βRIII In another aspect the immunomodulatory moiety includes an extracellular ligand-binding domain (ECD) of TGF-βRII In a still further aspect, the targeting moiety includes an antibody that specifically binds to HER2/neu, EGFR1, CD20, or cytotoxic T-lymphocyte antigen-4 (CTLA-4) and wherein the immunomodulatory moiety includes an extracellular ligand-binding domain of TGF-βRII.

In yet another aspect, the immunomodulatory moiety includes a molecule that specifically binds to and inhibits the activity of Programmed death-1 ligand 1 (PD-L 1).

In a further aspect, the targeting moiety includes an antibody, antibody fragment, or polypeptide that specifically binds to HER2/neu, EGFR1, CD20, cytotoxic T-lymphocyte antigen-4 (CTLA-4), CD25 (1L-2a receptor; IL-2aR), or CD4 and wherein, the immunomodulatory moiety includes an extracellular ligand-binding domain or ectodomain of Programmed Death-1 (PD-1).

In a still further aspect, the targeting moiety includes an antibody that specifically binds to EGFR1 and CTLA-4, and the immunomodulatory moiety includes a sequence from interacts with transforming growth factor-0 (TGF-β).

In one aspect, the present invention provides for optimized genes encoding for a fusion polypeptide comprising at least one targeting moiety and at least one immunomodulatory moiety for treating cancer in a human subject wherein the genes have been optimized to increase expression in a human subject and/or cells.

In another aspect, the present invention provides for a vector comprising optimized genes for treating cancer in a human subject wherein the optimized genes have been modified to increase CG sequences. Preferably, the vector includes nucleotide sequences for encoding at least one targeting moiety, at least one immunomodulatory moiety and a linking moiety, wherein the optimized nucleotide sequences are selected from SEQ ID NOs: 1 to 7, as set forth in FIG. 2.

In yet another aspect, the present invention provides for a method of treating cancer in a subject, the method comprising:

providing at least one recombinant vector comprising nucleotide sequences that encode at least one targeting moiety, at least one immunomodulatory moiety and a linking moiety positioned between the targeting moiety and immunomodulatory moiety, wherein the nucleotide sequences are selected from SEQ ID NOs: 1 to 7; and
administering the recombinant vector to the subject under conditions such that said nucleotide sequences are expressed at a level which produces a therapeutically effective amount of the encoded fusion proteins in the subject.

In yet another aspect, the present invention provides a recombinant host cell transfected with a polynucleotide sequence that encodes a fusion protein peptide of the present invention, wherein the polynucleotide sequences are selected from SEQ ID NOs: 1 to 7.

In a still further aspect, the present invention contemplates a process of preparing a chimeric fusion protein of the present invention comprising:

transfecting a host cell with a polynucleotide sequence that encodes a chimeric fusion protein to produce a transformed host cell, wherein the polynucleotide sequence encodes at least one targeting moiety and at least one immunomodulatory moiety, wherein the polynucleotide sequence comprises a combination of sequences selected from SEQ ID NOs: 1 to 7; and
maintaining the transformed host cell under biological conditions sufficient for expression of the chimeric fusion protein.

In another aspect, the present invention relates to the use of a chimeric fusion protein, wherein the chimeric fusion protein comprises anti-EGFR1 linker PD1 (SEQ ID NOs: 8, 9, 10 and 11); anti-EGFR1-linker-TGFβRII (SEQ ID NOs: 8, 9, 10 and 12); Anti-CTLA-4-linker-PD1 (SEQ ID NOs: 13, 14, 10 and 11), as shown in FIGS. 3, 4 and 5 respectively, in the use of a medicament for the treatment of cancer. Preferably, the fusion protein is expressed in a host cell and such expressed proteins are administered in a therapeutic amount to reduce the effects of cancer in a subject in need thereof.

In a still further aspect, the present invention provides a method of treating a neoplastic disease. The method includes administration to a subject in need thereof one or more fusion proteins of the present invention, in various aspects, the subject is administered one or more fusion protein of the present invention in combination with another anticancer therapy. In one aspect, the anticancer therapy includes a chemotherapeutic molecule, antibody, small molecule kinase inhibitor, hormonal agent or cytotoxic agent. The anticancer therapy may also include ionizing radiation, ultraviolet radiation, cryoablation, thermal ablation, or radiofrequency ablation.

In a preferred embodiment the therapeutically active antibody-peptide fusion proteins is a targeting antibody fused to one or more immunomodulating moiety that counteracts immune tolerance of a cancer cell. In one aspect, the immunomodulating moiety may be linked by an amino acid spacer of sufficient length to allow bi-specific binding of the molecule. The immunomodulating moiety may be bound to either the N-terminus or C-terminus of the heavy chain or the N-terminus or C-terminus of the light chain of the antibody The method of the present invention provides nucleotide sequences that encode the therapeutically active antibody-peptide fusion proteins and such expression may be conducted in a transient cell line or a stable cell line. The transient expression is accomplished by transfecting or transforming the host cell with vectors carrying the encoded fusion proteins into mammalian host cells Once the fusion peptides are expressed, they are preferably subjected to purification and in-vitro tests to check its bi-specificity, that being, having the ability to bind to both the target moiety and immunomodulating moiety. Such tests may include in-vitro tests such as ELISA or NK/T-cell binding assays to validate bi-functional target binding or immune cell stimulation.

Notably once the specific fusion peptides demonstrate the desired bi-specificity, the polynucleotide sequences encoding such fusion peptides are selected for sub-cloning into a stable cell line for larger scale expression and purification. Such stable cell lines are previously disclosed, such as a mammalian cell line, including but not limited to HEK293, CHO or NSO.

In another aspect the present invention provides for a method to inhibit and/or reduce binding of PDL1 to PD1 thereby increasing immune response against tumor cells, the method comprising:
 a. providing a chimeric polypeptide comprising PD1 and an anti-EGFR1 or anti-CTLA-4 antibody; and
 b. contacting a tumor cell with the chimeric polypeptide wherein the chimeric polypeptide binds with at least PDL1 of the tumor cell.

In yet another aspect, the present invention provides for a method of preparing therapeutically active antibody-peptide fusion proteins, the method comprising;
 a. preparing a codon optimized sequence of the said fusion protein, wherein the codon optimized sequences for anti-EGFR1 and anti-CTLA-4 antibodies are lacking nucleotides for expression of a lysine at the C-terminal end of the heavy chains of the antibodies;
 b. cloning the optimized sequence of said fusion protein in a host cell capable of transient or continued expression;
 c. growing the host cell in a media under suitable conditions for growing and allowing the host cell to express the fusion protein; and
 d. collecting secreted fusion proteins.

In a still further aspect the present invention provides for a nucleic acid sequence encoding a chimeric fusion protein, wherein the chimeric fusion protein comprises at least one targeting moiety having affinity for a cancer cell and at least one immunomodulatory moiety that counteract immune tolerance of the cancer cell, wherein targeting moiety is an antibody and the nucleic acid sequence of the targeting moiety is lacking nucleotides for expression of a lysine at the C-terminal end of the heavy chains of the antibody. The nucleic acid sequence encoding the heavy chain of the antibody preferably includes SEQ ID NO: 1 or SEQ ID NO:5. The nucleic acid sequence encoding the chimeric fusion proteins preferably comprises a sequence selected from the group consisting of SEQ ID NOs: 1, 2, 4 and 7; SEQ ID NOs: 1, 2, 3 and 4; and SEQ ID NOs: 5, 6, 3 and 4.

In yet another aspect the present invention provides for a method of treating cancer in a subject, the method comprising:
 a) preparing a preparing therapeutically active fusion protein, wherein the fusion protein comprises a tumor targeting moiety and at least one immunomodulatory molecule, wherein the tumor targeting moiety is an antibody that binds to CTLA-4 or EGFR1 and wherein the fusion protein is prepared by the following steps:
  i) preparing a codon optimized nucleotide sequence encoding the fusion protein, wherein the codon optimized nucleotide sequence for the antibody is lacking nucleotides for expression of a lysine at the C-terminal end of the heavy chains of the antibody;
  ii) cloning the optimized sequence of said fusion protein in a host cell capable of transient or continued expression;
  iii) growing the host cell in a media under suitable conditions for growing and allowing the host cell to express the fusion protein; and
  iv) collecting secreted fusion proteins;
 b) administering a therapeutically active amount of the secreted fusion proteins to the subject.

The fusion protein is selected from the group of amino acid sequences consisting of SEQ ID NOs: 15 and 9; SEQ ID NOs: 8 and 16; SEQ ID NOs: 17 and 9; SEQ ID NOs: 8 and 18; SEQ ID NOs: 27 and 9; SEQ ID NOs: 8 and 28; SEQ ID NOs: 29 and 9; SEQ ID NOs: 8 and 30; SEQ ID NOs: 31 and 28; SEQ ID NOs: 31 and 30; SEQ ID NOs: 29 and 28; SEQ ID NOs: 29 and 30; SEQ ID NOs: 32 and 14; SEQ ID NOs: 13 and 33; SEQ ID NOs: 34 and 14; SEQ ID NOs: 13 and 35; SEQ ID NOs: 32 and 33; SEQ ID NOs: 32 and 35; SEQ ID NOs: 34 and 33 and SEQ ID NOs: 34 and 35.

In another aspect, the present invention provides for a method of treating a neoplastic disease, the method comprising administration to a subject in need thereof one or more fusion proteins encoded by at least one polynucleotide sequence selected from the group consisting of SEQ ID NOs: 1, 2, 4 and 7; SEQ ID NOs: 1, 2, 3 and 4; and SEQ ID NOs: 5, 6, 3 and 4. Notably by using the above defined polynucleotide sequences, the following combination of fusion proteins can be expressed including anti-EGFR1 linker PD1 (SEQ ID NOs: 8, 9, 10 and 11); anti-EGFR1-linker-TGFβRII (SEQ ID NOs: 8, 9, 10 and 12); and Anti-CTLA-4-linker-PD1 (SEQ ID NOs: 13, 14, 10 and 11).

Other features and advantages of the invention will be apparent from the following detailed description, drawings and claims.

BRIEF DESCRIPTION OF THE FIGURES

FIG. 2 shows the optimized codon nucleotide sequences used for expression of the antibody-peptide fusion proteins of the present invention, including Anti-EGFR1 heavy chain (SEQ ID NO: 1); Anti-EGFR1 light chain (SEQ ID NO: 2); PD1 (SEQ ID NO: 7); Linker (SEQ ID NO: 4); Anti-CTLA-4 heavy chain (SEQ ID NO: 5); Anti-CTLA-4 light chain (SEQ ID NO: 6) and TGFβRII (SEQ ID NO: 3).

FIG. 3 shows the amino acid residues for the anti-EGFR1 linker PD1 construct (SEQ ID NOs: 8, 9, 10 and 11).

FIG. 4 shows the amino acid residues for anti-EGFR1-linker-TGFβRII construct (SEQ ID NOs: 8, 9, 10 and 12).

FIG. 5 shows the amino acid residues for the anti-CTLA-4-linker-PD1 (SEQ ID NOs: 13, 14, 10 and 11).

FIG. 7 shows the amino acid sequences for Anti-EGFR1 HC-PD1+Anti-EGFR1 LC wherein the PD1 molecule is connected to the C terminus of the heavy chain separated by a linker and including SEQ ID NOs: 15 and 9.

FIG. 8 shows the amino acid sequences for Anti-EGFR1 HC+Anti-EGFR1 LC–PD1 wherein the PD1 molecule is connected to the C terminus of the light chain separated by a linker and including SEQ ID NOs: 8 and 16.

FIG. 9 shows the amino acid sequences for Anti-EGFR1 HC+Anti-EGFR1 LC–PD1 wherein the PD1 molecule is connected to the N terminus of the heavy chain separated by a linker and including SEQ ID NOs: 17 and 9.

FIG. 10 shows the amino acid sequences for Anti-EGFR1 HC+PD1-Anti-EGFR1 LC wherein the PD1 molecule is connected to the N terminus of the light chain separated by a linker and including SEQ ID NOs: 8 and 18.

FIG. 13 shows the amino acid sequences for Anti-EGFR1 HC-TGFβRII+Anti-EGFR1 LC wherein the TGFβRII molecule is connected to the C terminus of the heavy chain separated by a linker and including SEQ ID NOs: 27 and 9.

FIG. 14 shows the amino acid sequences for Anti-EGFR1 HC+Anti-EGFR1 LC-TGFβRII wherein the TGFβRII molecule is connected to the C terminus of the light chain separated by a linker and including SEQ ID NOs: 8 and 28.

FIG. 15 shows the amino acid sequences for TGFβRII-Anti-EGFR1 HC+Anti-EGFR1 LC wherein the TGFβRII molecule is connected to the N terminus of the heavy chain separated by a linker and including SEQ ID NOs: 29 and 9.

FIG. 16 shows the amino acid sequences for Anti-EGFR1 HC+TGFβRII-Anti-EGFR1 LC wherein the TGFβRII molecule is connected to the N terminus of the light chain separated by a linker and including SEQ ID NOs: 8 and 30.

FIG. 17 shows the amino acid sequences for Anti-EGFR1 HC-TGFβRII+Anti-EGFR1 LC-TGFβRII wherein the TGFβRII molecule is connected to the C terminus of the heavy and light chain separated by a linker and including SEQ ID NOs: 31 and 28.

FIG. 18 shows the amino acid sequences for Anti-EGFR1 HC-TGFβRII+TGFβRII-Anti-EGFR1 LC wherein the TGFβRII molecule is connected to the C terminus of the heavy chain and N terminus of the light chain separated by a linker and including SEQ ID NOs: 31 and 30.

FIG. 19 shows the amino acid sequences for TGFβRII-Anti-EGFR1 HC+Anti-EGFR1 LC-TGFβRII wherein the TGFβRII molecule is connected to the N terminus of the heavy chain and C terminus of the light chain separated by a linker and including SEQ ID NOs: 29 and 28.

FIG. 20 shows the amino acid sequences for TGFβRII-Anti-EGFR1 HC+TGFβRII-Anti-EGFR1 LC wherein the TGFβRII molecule is connected to the N terminus of the heavy chain and N terminus of the light chain separated by a linker and including SEQ ID NOs: 29 and 30.

FIG. 25 shows the amino acid sequences for Anti-CTLA4 HC-PD1+Anti-CTLA4 LC wherein the PD1 molecule is connected to the C terminus of the heavy chain separated by a linker and including SEQ ID NOs: 32 and 14.

FIG. 26 shows the amino acid sequences for Anti-CTLA4 HC+Anti-CTLA4 LC-PD1 wherein the PD1 molecule is connected to the C terminus of the light chain separated by a linker and including SEQ ID NOs: 13 and 33.

FIG. 27 shows the amino acid sequences for PD1-Anti-CTLA4 HC+Anti-CTLA4 LC wherein the PD1 molecule is connected to the N terminus of the heavy chain separated by a linker and including SEQ ID NOs: 34 and 14.

FIG. 28 shows the amino acid sequences for Anti-CTLA4 HC+PD1-Anti-CTLA4 LC wherein the PD1 molecule is connected to the N terminus of the light chain separated by a linker and including SEQ ID NOs: 13 and 35.

FIG. 29 shows the amino acid sequences for Anti-CTLA4 HC-PD1+Anti-CTLA4 LC-PD1 wherein the PD1 molecule is connected to the C terminus of the heavy chain and light chain separated by a linker and including SEQ ID NOs: 32 and 33.

FIG. 30 shows the amino acid sequences for Anti-CTLA4 HC-PD1+PD1-Anti-CTLA4 LC wherein the PD1 molecule is connected to the C terminus of the heavy chain separated by a linker and N terminus of the light chain including SEQ ID NOs: 32 and 35.

FIG. 31 shows the amino acid sequences for PD1-Anti-CTLA4 HC+Anti-CTLA4 LC-PD1 wherein the PD1 molecule is connected to the N terminus of the heavy chain separated by a linker and C terminus of the light chain including SEQ ID NOs: 34 and 33.

FIG. 32 shows the amino acid sequences for PD1-Anti-CTLA4 HC+PD1-Anti-CTLA4 LC wherein the PD1 molecule is connected to the N terminus of the heavy chain separated by a linker and N terminus of the light chain including SEQ ID NOs: 34 and 35.

DETAILED DESCRIPTION OF THE INVENTION

Figure 1:
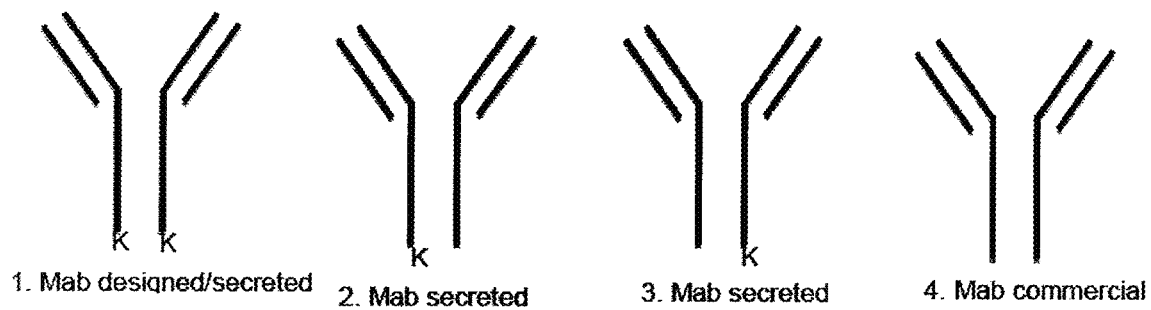
FIG. 1 shows the different possibilities of lysine placement on a heavy chain and such heterogeneity causing the need to provide purification.

In order to facilitate review of the various embodiments of the invention and provide an understanding of the various elements and constituents used in making and using the present invention, the following terms used in the invention description have the following meanings.

As used herein, the terms "polypeptide," "protein" and "peptide" are used interchangeably to denote a sequence polymer of at least two amino acids covalently linked by an amide bond, regardless of length or post-translational modification (e.g., glycosylation, phosphorylation, lipidation, myristilation, ubiquitination, etc.). D- and L-amino acids, and mixtures of D- and L-amino acids are also included.

Chimeric polypeptide refers to an amino acid sequence having two or more parts which generally are not found together in an amino acid sequence in nature.

The term "spacer/linker" as used herein refers to a molecule that connects two monomeric protein units to form a chimeric molecule and still provides for binding of the parts to the desired receptors. Particular examples of spacer/linkers may include an amino acid spacer, wherein thee amino acid sequence can essentially be any length, for example, as few as 5 or as many as 200 or more preferably from about 5 to 30 amino acid residues.

The term "therapeutic," as used herein, means a treatment administered to a subject who exhibits signs of pathology for the purpose of diminishing or eliminating those signs.

The term "therapeutically effective amount," as used herein means an amount of the chimeric protein that is sufficient to provide a beneficial effect to the subject to which the chimeric protein is administered.

Another example of a modification is the addition of a heterologous domain that imparts a distinct functionality upon the chimeric polypeptide. A heterologous domain can be any small organic or inorganic molecule or macromolecule, so long as it imparts an additional function. Particular examples of heterologous domains that impart a distinct function include an amino acid sequence that imparts targeting (e.g., receptor ligand, antibody, etc.), immunopotentiating function (e.g., immunoglobulin, an adjuvant), enable purification, isolation or detection (e.g., myc, T7 tag, polyhistidine, avidin, biotin, lectins, etc.).

As exemplified herein, polypeptide sequences may include substitutions, variations, or derivitizations of the amino acid sequence of one or both of the polypeptide sequences that comprise the chimeric polypeptide, so long as the modified chimeric polypeptide has substantially the same activity or function as the unmodified chimeric polypeptide.

As used herein, the term "substantially the same activity or function," when used in reference to a chimeric polypeptide so modified, means that the polypeptide retains most, all or more of the activity associated with the unmodified polypeptide, as described herein or known in the art.

Modified chimeric polypeptides that are "active" or "functional" included herein can be identified through a routine functional assay. For example, by using antibody binding assays or co-receptor binding assays one can readily determine whether the modified chimeric polypeptide has activity. As the modified chimeric polypeptides will retain activity or function associated with unmodified chimeric polypeptide, modified chimeric polypeptides will generally have an amino acid sequence "substantially identical" or "substantially homologous" with the amino acid sequence of the unmodified polypeptide.

As used herein, the term "substantially identical" or "substantially homologous," when used in reference to a polypeptide sequence, means that a sequence of the polypeptide is at least 50% identical to a reference sequence. Modified polypeptides and substantially identical polypeptides will typically have at least 70%, alternatively 85%, more likely 90%, and most likely 95% homology to a reference polypeptide.

As set forth herein, substantially identical or homologous polypeptides include additions, truncations, internal deletions or insertions, conservative and non-conservative substitutions, or other modifications located at positions of the amino acid sequence which do not destroy the function of the chimeric polypeptide (as determined by functional assays, e.g., as described herein). A particular example of a substitution is where one or more amino acids are replaced by another, chemically or biologically similar residue. As used herein, the term "conservative substitution" refers to a substitution of one residue with a chemically or biologically similar residue. Examples of conservative substitutions include the replacement of a hydrophobic residue, such as isoleucine, valine, leucine, or methionine for another, the replacement of a polar residue for another, such as the substitution of arginine for lysine, glutamic for aspartic acids, or glutamine for asparagine, and the like. Those of skill in the art will recognize the numerous amino acids that can be modified or substituted with other chemically similar residues without substantially altering activity.

Modified polypeptides further include "chemical derivatives," in which one or more of the amino acids therein have a side chain chemically altered or derivatized. Such derivatized polypeptides include, for example, amino acids in which free amino groups form amine hydrochlorides, p-toluene sulfonyl groups, carobenzoxy groups; the free carboxy groups form salts, methyl and ethyl esters; free hydroxyl groups that form O-acyl or O-alkyl derivatives, as well as naturally occurring amino acid derivatives, for example, 4-hydroxyproline, for proline, 5-hydroxylysine for lysine, homoserine for serine, ornithine for lysine, and so forth. Also included are D-amino acids and amino acid derivatives that can alter covalent bonding, for example, the disulfide linkage that forms between two cysteine residues that produces a cyclized polypeptide.

As used herein, the terms "isolated" or "substantially pure," when used as a modifier of invention chimeric polypeptides, sequence fragments thereof, and polynucleotides, means that they are produced by human intervention and are separated from their native in vivo-cellular environment. Generally, polypeptides and polynucleotides so separated are substantially free of other proteins, nucleic acids, lipids, carbohydrates or other materials with which they are naturally associated.

Polypeptides of the present invention may be prepared by standard techniques well known to those skilled in the art. Such techniques include, but are not limited to, isolation and purification from tissues known to contain that polypeptide, and expression from cloned DNA that encodes such a polypeptide using transformed cells. Chimeric polypeptides can be obtained by expression of a polynucleotide encoding the polypeptide in a host cell, such as a bacteria, yeast or mammalian cell, and purifying the expressed chimeric polypeptide by purification using typical biochemical methods (e.g., immunoaffinity purification, gel purification, expression screening etc.). Other well-known methods are described in Deutscher et al., 1990. Alternatively, the chimeric polypeptide can be chemically synthesized. Purity can be measured by any appropriate method, e.g., polyacrylamide gel electrophoresis, and subsequent staining of the gel (e.g., silver stain) or by HPLC analysis.

The present invention further provides polynucleotide sequences encoding chimeric polypeptides, fragments thereof, and complementary sequences. As used herein, the terms "nucleic acid," "polynucleotide," "oligonucleotide," and "primer" are used interchangeably to refer to deoxyribonucleic acid (DNA) or ribonucleic (RNA), either double- or single-stranded, linear or circular. RNA can be unspliced or spliced mRNA, rRNA, tRNA, or antisense RNAi. DNA can be complementary DNA (cDNA), genomic DNA, or an antisense. Specifically included are nucleotide analogues and derivatives, such as those that are resistant to nuclease degradation, which can function to encode an invention chimeric polypeptide. Nuclease resistant oligonucleotides and polynucleotides are particularly useful for the present nucleic acid vaccines described herein.

An "isolated" or "substantially pure" polynucleotide means that the nucleic acid is not immediately contiguous with the coding sequences with either the 5' end or the 3' end with which it is immediately contiguous in the naturally occurring genome of the organism from which it is derived. The term therefore includes, for example, a recombinant DNA (e.g., a cDNA or a genomic DNA fragment produced by PCR or restriction endonuclease treatment produced during cloning), as well as a recombinant DNA incorporated into a vector, an autonomously replicating plasmid or virus, or a genomic DNA of a prokaryote or eukaryote.

The polynucleotides sequences of the present invention can be obtained using standard techniques known in the art (e.g., molecular cloning, chemical synthesis) and the purity can be determined by polyacrylamide or agarose gel electrophoresis, sequencing analysis, and the like. Polynucleotides also can be isolated using hybridization or computer-based techniques that are well known in the art. Such techniques include, but are not limited to: (1) hybridization of genomic DNA or cDNA libraries with probes to detect homologous nucleotide sequences; (2) antibody screening of polypeptides expressed by DNA sequences (e.g., using an expression library); (3) polymerase chain reaction (PCR) of genomic DNA or cDNA using primers capable of annealing to a nucleic acid sequence of interest; (4) computer searches of sequence databases for related sequences; and (5) differential screening of a subtracted nucleic acid library.

The invention also includes substantially homologous polynucleotides. As used herein, the term "homologous," when used in reference to nucleic acid molecule, refers to similarity between two nucleotide sequences. When a nucleotide position in both of the molecules is occupied by identical nucleotides, then they are homologous at that position. "Substantially homologous" nucleic acid sequences are at least 50% homologous, more likely at least 75% homologous, and most likely 90% or more homologous. As with substantially homologous invention chimeric polypeptides, polynucleotides substantially homologous to invention polynucleotides encoding chimeric polypeptides encode polypeptides that retain most or all of the activity or function associated with the sequence to which it is homologous. For polynucleotides, the length of comparison between sequences will generally be at least 30 nucleotides, alternatively at least 50 nucleotides, more likely at least 75 nucleotides, and most likely 110 nucleotides or more. Algorithms for identifying homologous sequences that account for polynucleotide sequence gaps and mismatched oligonucleotides are known in the art, such as BLAST (see Altschul, 1990).

The polynucleotides of the present invention can, if desired: be naked or be in a carrier suitable for passing through a cell membrane (e.g., polynucleotide-liposome complex or a colloidal dispersion system), contained in a vector (e.g., retrovirus vector, adenoviral vectors, and the like), linked to inert beads or other heterologous domains (e.g., antibodies, ligands, biotin, streptavidin, lectins, and the like), or other appropriate compositions disclosed herein or known in the art. Thus, viral and non-viral means of polynucleotide delivery can be achieved and are contemplated. The polynucleotides of the present invention can also contain additional nucleic acid sequences linked thereto that encode a polypeptide having a distinct functionality, such as the various heterologous domains set forth herein.

The polynucleotides of the present invention can also be modified, for example, to be resistant to nucleases to enhance their stability in a pharmaceutical formulation. The described polynucleotides are useful for encoding chimeric polypeptides of the present invention, especially when such polynucleotides are incorporated into expression systems disclosed herein or known in the art. Accordingly, polynucleotides including an expression vector are also included.

For propagation or expression in cells, polynucleotides described herein can be inserted into a vector. The term "vector" refers to a plasmid, virus, or other vehicle known in the art that can be manipulated by insertion or incorporation of a nucleic acid. Such vectors can be used for genetic manipulation (i.e., "cloning vectors") or can be used to transcribe or translate the inserted polynucleotide (i.e., "expression vectors"). A vector generally contains at least an origin of replication for propagation in a cell and a promoter. Control elements, including promoters present within an expression vector, are included to facilitate proper transcription and translation (e.g., splicing signal for introns, maintenance of the correct reading frame of the gene to permit in-frame translation of mRNA and stop codons). In vivo or in vitro expression of the polynucleotides described herein can be conferred by a promoter operably linked to the nucleic acid.

"Promoter" refers to a minimal nucleic acid sequence sufficient to direct transcription of the nucleic acid to which the promoter is operably linked (see Bitter 1987). Promoters can constitutively direct transcription, can be tissue-specific, or can render inducible or repressible transcription; such elements are generally located in the 5' or 3' regions of the gene so regulated.

As used herein, the term "operably linked" means that a selected polynucleotide (e.g., encoding a chimeric polypeptide) and regulatory sequence(s) are connected in such a way as to permit transcription when the appropriate molecules (e.g., transcriptional activator proteins) are bound to the regulatory sequence(s). Typically, a promoter is located at the 5' end of the polynucleotide and may be in close proximity of the transcription initiation site to allow the promoter to regulate expression of the polynucleotide.

When cloning in bacterial systems, constitutive promoters, such as T7 and the like, as well as inducible promoters, such as pL of bacteriophage gamma, plac, ptrp, ptac, may be used. When cloning in mammalian cell systems, constitutive promoters, such as SV40, RSV and the like, or inducible promoters derived from the genome of mammalian cells (e.g., the metallothionein promoter) or from mammalian viruses (e.g., the mouse mammary tumor virus long terminal repeat, the adenovirus late promoter), may be used. Promoters produced by recombinant DNA or synthetic techniques may also be used to provide for transcription of the nucleic acid sequences of the invention.

Mammalian expression systems that utilize recombinant viruses or viral elements to direct expression may be engineered. For example, when using adenovirus expression vectors, the nucleic acid sequence may be ligated to an adenovirus transcription/translation control complex, e.g., the late promoter and tripartite leader sequence. Alternatively, the vaccinia virus 7.5K promoter may be used (see Mackett 1982; Mackett 1984; Panicali 1982).

For yeast expression, a number of vectors containing constitutive or inducible promoters may be used (see Ausubel 1988; Grant 1987; Glover 1986; Bitter 1987; and Strathem 1982). The polynucleotides may be inserted into an expression vector for expression in vitro (e.g., using in vitro transcription/translation kits, which are available commercially), or may be inserted into an expression vector that contains a promoter sequence that facilitates expression in either prokaryotes or eukaryotes by transfer of an appropriate nucleic acid into a suitable cell, organ, tissue, or organism in vivo.

As used herein, a "transgene" is any piece of a polynucleotide inserted by artifice into a host cell, and becomes part of the organism that develops from that cell. A transgene can include one or more promoters and any other DNA, such as introns, necessary for expression of the selected DNA, all operably linked to the selected DNA, and may include an enhancer sequence. A transgene may include a polynucleotide that is partly or entirely heterologous (i.e., foreign) to the transgenic organism, or may represent a gene homologous to an endogenous gene of the organism. Transgenes may integrate into the host cell's genome or be maintained as a self-replicating plasmid.

As used herein, a "host cell" is a cell into which a polynucleotide is introduced that can be propagated, transcribed, or encoded polypeptide expressed. The term also includes any progeny of the subject host cell. It is understood that all progeny may not be identical to the parental cell, since there may be mutations that occur during replication. Host cells include but are not limited to bacteria, yeast, insect, and mammalian cells. For example, bacteria transformed with recombinant bacteriophage polynucleotide, plasmid nucleic acid, or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV), or transformed with recombinant plasmid expression vectors (e.g., Ti plasmid), insect cell systems infected with recombinant virus expression vectors (e.g., baculovirus), or animal cell systems infected with recombinant virus expression vectors (e.g., retroviruses, adenovirus, vaccinia virus), or transformed animal cell systems engineered for stable expression.

As used herein, the term "transformation" means a genetic change in a cell following incorporation of a polynucleotide (e.g., a transgene) exogenous to the cell. Thus, a "transformed cell" is a cell into which, or a progeny of which, a polynucleotide has been introduced by means of recombinant techniques. Transformation of a host cell may be carried out by conventional techniques known to those skilled in the art. When the host cell is a eukaryote, methods of DNA transformation include, for example, calcium phosphate, microinjection, electroporation, liposomes, and viral vectors. Eukaryotic cells also can be co-transformed with invention polynucleotide sequences or fragments thereof, and a second DNA molecule encoding a selectable marker, as described herein or otherwise known in the art. Another method is to use a eukaryotic viral vector, such as simian virus 40 (SV40) or bovine papilloma virus, to transiently infect or transform eukaryotic cells, and express the protein (see Gluzman 1982). When the host is prokaryotic (e.g., *E. coli*), competent cells that are capable of DNA uptake can be prepared from cells harvested after exponential growth phase and subsequently treated by the $CaCl_2$) method using procedures well-known in the art. Transformation of prokaryotes also can be performed by protoplast fusion of the host cell.

Chimeric polypeptides, polynucleotides, and expression vectors containing same of the present invention can be encapsulated within liposomes using standard techniques and introduced into cells or whole organisms. Cationic liposomes are preferred for delivery of polynucleotides. The use of liposomes for introducing various compositions in vitro or in vivo, including proteins and polynucleotides, is known to those of skill in the art.

Liposomes can be targeted to a cell type or tissue of interest by the addition to the liposome preparation of a ligand, such as a polypeptide, for which a corresponding cellular receptor has been identified. Monoclonal antibodies can also be used for targeting; many such antibodies specific for a wide variety of cell surface proteins are known to those skilled in the art and are available. The selected ligand is covalently conjugated to a lipid anchor in either preformed liposomes or are incorporated during liposome preparation (see Lee 1994 and Lee 1995).

As the chimeric polypeptides or polynucleotides of the present invention will be administered to humans, the present invention also provides pharmaceutical formulations comprising the disclosed chimeric polypeptides or polynucleotides. The compositions administered to a subject will therefore be in a "pharmaceutically acceptable" or "physiologically acceptable" formulation.

As used herein, the terms "pharmaceutically acceptable" and "physiologically acceptable" refer to carriers, diluents, excipients, and the like that can be administered to a subject, preferably without excessive adverse side effects (e.g., nausea, headaches, etc.). Such preparations for administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions, or suspensions, including saline and buffered media. Vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present, such as, for example, antimicrobial, anti-oxidants, chelating agents, and inert gases and the like. Various pharmaceutical formulations appropriate for administration to a subject known in the art are applicable in the methods of the invention (e.g., Remington's Pharmaceutical Sciences, 18th ed., Mack Publishing Co., Easton, PA (1990); and The Merck Index, 12th ed., Merck Publishing Group, Whitehouse, NJ (1996)).

Controlling the duration of action or controlled delivery of an administered composition can be achieved by incorporating the composition into particles or a polymeric substance, such as polyesters, polyamine acids, hydrogel, poly-vinyl pyrrolidone, ethylene-vinylacetate, methylcellulose, carboxymethylcellulose, protamine sulfate or lactide/glycolide copolymers, polylactide/glycolide copolymers, or ethylenevinylacetate copolymers. The rate of release of the composition may be controlled by altering the concentration or composition of such macromolecules. Colloidal dispersion systems include macromolecule complexes, nano-capsules, microspheres, beads, and lipid-based systems, including oil-in-water emulsions, micelles, mixed micelles, and liposomes.

The compositions administered by a method of the present invention can be administered parenterally by injection, by gradual perfusion over time, or by bolus administration or by a microfabricated implantable device. The composition can be administered via inhalation, intravenously, intraperitoneally, intramuscularly, subcutaneously, intracavity (e.g., vaginal or anal), transdermally, topically, or intravascularly. The compositions can be administered in multiple doses. An effective amount can readily be determined by those skilled in the art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Other features and advantages of the invention will be apparent from the following detailed description, and from the claims. The invention is further described in the following examples, which do not limit the scope of the invention(s) described in the claims.

Examples

1. Anti-EGFR1-PD1 Fusion Protein Constructs for Cancer Targets

Anti-EGFR (Cetuximab) has been approved for squamous Head and Neck Cancer (locally or regionally advanced in combination with radiotherapy and metastatic after platinum based therapy) and EGFR expressing metastatic colorectal cancer (monotherapy in patients after failure of both oxaliplatin and irinotecan based chemo or in patients intolerant to irinotecan based chemo). Not applicable for colonrectal cancer (CRC) patients having K-RAS mutations.

Across various studies about 55-60% of mCRC patients respond to cetuximab in first line setting, however, this response too is transient (progression free survival (PFS) advantage of 1.5-2 mths) (EPAR). Significant numbers of patients either do not respond to cetuximab or become resistant to therapy. In the recurrent metastatic head and neck cancer, only 35% patients respond to cetuximab with chemo with only 2-3 month overall survival (OS) and (PFS) advantage.

Clearly, a significant unmet need exists to improve efficacy of cetuximab therapy in both these indications. Moreover, EGFR is also expressed in gastric cancer, non-small cell lung cancer (NSCLC) and pancreatic cancers. However, cetuximab has failed to prove any significant benefit in these indications over standard of care. Thus, the present invention provides for improvement by combining cetuximab with an immunomodulatory therapy.

Programmed death-1 (PD-1) is an inhibitory receptor expressed on T cells after activation. It has been shown to down-regulate T-cell activity upon binding its ligand PD-L1 on APCs. Many tumors constitutively express PD-L1 and its' over expression has been associated with impaired tumor immunity, more aggressive disease and decreased survival (see Thompson 2004). Till date PD-L1 expression has been demonstrated to correlate with poor prognosis in patients with renal cell carcinoma (RCC), ovarian cancer and melanoma. Immunohistochemical analysis of freshly isolated tumor samples from patients with ovarian, lung, and breast cancers, renal cell carcinoma, squamous cell carcinoma of the head and neck, esophageal carcinoma, glioblastoma, thymoma, colon carcinoma, pancreatic and melanoma found that the vast majority express B7-H1 (see Flies 2011; Nomi 2007). Several pre-clinical studies have demonstrated increased tumor rejection by blocking PD1-PDL1 interaction. Recently, anti-PD1 and PD-L1 based therapies have demonstrated considerable activity in melanoma and some other solid tumors confirming their application as one of the most promising anti-cancer therapies.

Cetuximab based therapy may be improved upon by combining it with immunomodulation to remove immunosuppressive environment or delay the development of resistance. Moreover, patients who develop resistance to cetuximab due to mutations in the downstream pathways may still benefit from Anti-EGFR1-PD-1 since the fusion protein of the present invention binds to the EGFR receptor and negates the PD-L1 expressed by the tumors, allowing T cells to mount an anti-tumor response. Accordingly, the fusion proteins of the present invention can bind to EGFR and PD-L1 on the surface of the tumor cells.

The anti-EGFR1-PD1 fusion protein constructs of the present invention may be used in colorectal cancer, squamous head and neck cancer, non-small cell lung cancer, gastric cancer and pancreatic cancer.

Design and Selection of the Molecules:

The antibody fusion molecules of the present invention have duel therapeutic properties. On one hand the molecule retains the complete activity of the Anti-EGFR1 (Cetuximab) and in parallel, it has the PD-L1 receptor binding activity in the tumor environment. The new molecules of the Anti-EGFR1-PD1 fusion proteins that were developed for the cancer therapies herein are devoid of the amino acid lysine 'K' from the C-terminus of heavy chain for the reasons described above. The main objective of the fusion protein design is to keep the anti-EGFR1 molecule intact along with its function unaffected and allows fusion of the PD1 molecule to the various location on the anti-EGFR1 antibody. That being, fusion to the HC C-terminus, LC C-terminus, HC N-terminus, and or LC N-terminus and double fusions on both the chains as shown in FIG. 6.

The following constructs were designed.

TABLE 1

Figure 6:
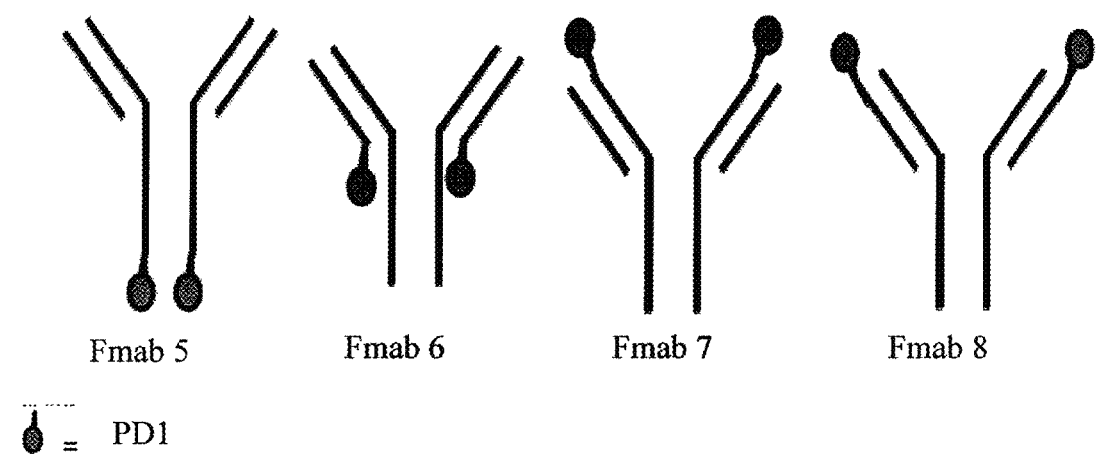
FIG. 6 shows the different possibilities for placement of the PD1 molecule on the anti-EGFR1 antibody for FMab5, FMab6, FMab7 and FMab8.

| Constructs. no. | Fusion mAbs name |
|---|---|
| FMab5 FIG. 6 | Anti-EGFR1 HC-PD1 + Anti-EGFR1 LC (AA sequences in FIG. 7, SEQ ID NO: 15 and 9) |
| FMab6 FIG. 6 | Anti-EGFR1 HC + Anti-EGFR1 LC -PD1 (AA sequences in FIG. 8, SEQ ID NO: 8 and 16) |
| FMab7 FIG. 6 | PD1-Anti-EGFR1 HC + Anti-EGFR1 LC (AA sequences in FIG. 9, SEQ ID NO: 17 and 9) |
| FMab8 FIG. 6 | Anti-EGFR1 HC + PD1-Anti-EGFR1 LC (AA sequences in FIG. 10, SEQ ID NO: 8 and 18) |

Expression of the above fusion constructs in CHO cells:

The codon-optimized nucleotide sequences of the Anti-EGFR1-PD1 individual domains were optimized for expression in CHO cells. Such optimized sequences (SEQ ID NOs: 1, 2, 7, and 4) were assemble in a mammalian expression vector with help of primers described in Table 2:

TABLE 2

| FMAB7FP1 | AGA TAT CGC CAC CAT GAT GTC CTT CGT G SEQ ID NO: 19 |
|---|---|
| FMAB7FP2 | GGC GGC GGA GGC TCT CAG GTG CAG CTG AAG CAG TC SEQ ID NO: 20 |
| FMAB7RP1 | AGT ATA CTC AGC CGG GGG ACA GAG A SEQ ID NO: 21 |
| FMAB7RP2 | TTC AGC TGC ACC TGA GAG CCT CCG CCG CCA CTT C SEQ ID NO: 22 |
| FMAB7LCRP | ATT AAT TAA TCA ACA CTC GCC CCG GTT GAA GGA CT SEQ ID NO: 23 |
| FMAB6FP2 | CTC TGT CCC CCG GCG GCG GCG GAG GAT CTG GCG GA SEQ ID NO: 24 |
| FMAB6RP2 | GAT CCT CCG CCG CCG CCG GGG GAC AGA GAC AGG GA SEQ ID NO: 25 |
| FMAB6RP1 | AGT ATA CTC ACA CCA GGG TCT GGA AC SEQ ID NO: 26 |

Figure 11:
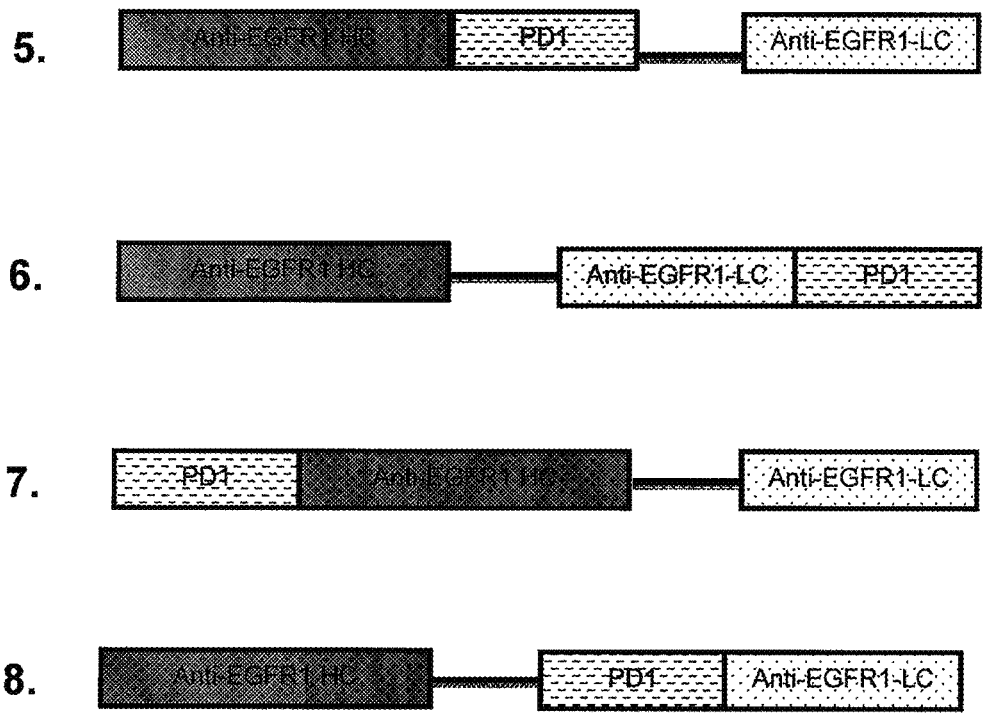
FIG. 11 shows expression constructs developed using the cDNAs as set forth in SEQ ID NOs: 1, 2 and 7.

Using the shown above cDNA primers set, constructs were assembled as shown in FIG. 11.

2. Anti-EGFR1-TGFβRII Fusion Proteins for Treatment of Cancer.

High levels of TGFβ are produced by many types of tumors, including melanomas and cancers of the breast, colon, esophagus, stomach, liver, lung, pancreas, and prostate, as well as hematologic malignancies (see Teicher 2001; Dong 2006). TGFβ is known to be immunosuppressive for T cells and NK cells through blocking of IL-2 and other mechanisms, including generation of T-regs. Several lines of evidence suggest that negating TGFβ activity may enhance anti-tumor effects of T cells (Wrzesinski 2007). Moreover, TGFβ can foster tumor growth through epithelial to mesenchymal transition and promoting angiogenesis. TGFβ expression is also associated with poor prognosis in patients and earlier recurrence. However, considering the pleotropic effects of TGFβ in controlling the immune response, it has been shown that generalized blocking of TGFβ activity may result in widespread auto-inflammatory activity. Hence, localized depletion of TGFβ in the tumor vicinity may be an alternative way to modulate immunosuppressive environment. Anti-EGFR1-TGFβRII fusion protein of the present invention binds to EGFR on the tumor cells and ties up the TGFβ around the tumor to enhance immune response against tumor cells.

Design and Selection of the Molecules:

The objective is to design the antibody fusion molecules which have duel therapeutic properties. On one hand the molecule should retain the complete activity of the Anti-EGFR1 (cetuximab) and in parallel; it should have the TGFβ binding activity in the tumor environment. The amino acid sequence of the Anti-EGFR1 IgG molecule was retained excepting that the lysine was not expressed at the C-terminus of the heavy chain. Both single and double fusion and expression levels are shown in Table 3, wherein TGFβRII was fused with Anti-EGFR1.

TABLE 3

Figure 12:
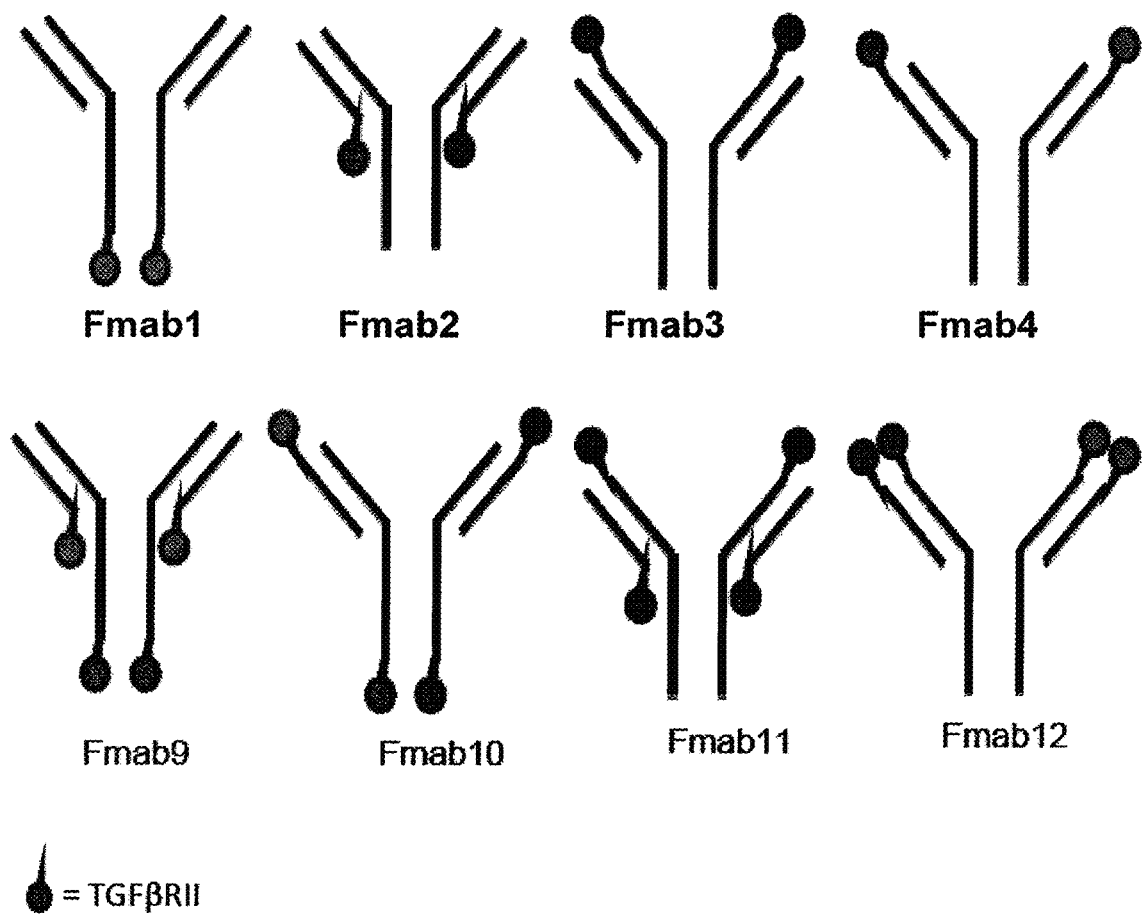
FIG. 12 shows the different possibilities for placement of the TGFβRII molecule on the anti-EGFR1 antibody, FMab1, FMab2, FMab3, FMab4, FMab9, FMab10, FMab11 and, FMab12.

| Construct. no. | Fusion Mabs name |
|---|---|
| FMab1 FIG. 12 | Anti-EGFR1 HC-TGFβRII + Anti-EGFR1 LC (AA sequences in FIG. 13, SEQ ID NO: 27 and 9) |
| FMab2 FIG. 12 | Anti-EGFR1 HC + Anti-EGFR1 LC -TGFβRII (AA sequences in FIG. 14, SEQ ID NO: 8 and 28) |

TABLE 3-continued

| Construct. no. | Fusion Mabs name |
|---|---|
| FMab3 FIG. 12 | TGFβRII-Anti-EGFR1 HC + Anti-EGFR1 LC (AA sequences in FIG. 15, SEQ ID NO: 29 and 9) |
| FMab4 FIG. 12 | Anti-EGFR1 HC + TGFβRII-Anti-EGFR1 LC (AA sequences in FIG. 16, SEQ ID NO: 8 and 30) |
| FMab9 FIG. 12 | Anti-EGFR1 HC-TGFβRII + Anti-EGFR1 LC -TGFβRII) (AA sequences in FIG. 17, SEQ ID NO: 31 and 28) |
| FMab10 FIG. 12 | Anti-EGFR1 HC-TGFβRII + TGFβRII-Anti-EGFR1 LC (AA sequences in FIG. 18, SEQ ID NO: 31 and 30) |
| FMab11 FIG. 12 | TGFβRII-Anti-EGFR1 HC + Anti-EGFR1 LC -TGFβRII (AA sequences in FIG. 19, SEQ ID NO: 29 and 28) |
| FMab12 FIG. 12 | TGFβRII-Anti-EGFR1 HC + TGFβRII-Anti-EGFR1 LC (AA sequences in FIG. 20, SEQ ID NO: 29 and 30) |

Expression of the Above Fusion Constructs in CHO Cells:

The codon-optimized nucleotide sequences of the Anti-EGFR1-TGFβRII individual domains were optimized for expression in CHO cells. Such sequences (SEQ ID NOs: 1, 2, 4, and 3) were assemble in a mammalian expression vector. The expression constructs are set forth in FIG. 21.

Transfection of the above vectors combination to obtain the desired cell line:

The expression constructs developed above were transfected in the following combination, as set forth in Table 4, into CHO cells to produce the following fusion proteins using the constructs as defined in FIG. 21.

TABLE 4

| Sl. No. | Fusion protein Name | Expression constructs combination transfected | Cell line used | Titer g/L |
|---|---|---|---|---|
| FMab1 | Anti-EGFR1 HC-TGFβRII + Anti-EGFR1 LC (HC-C-terminus) | Expression constructs # 2C and 3 C | CHO | 0.11 |
| FMab2 | Anti-EGFR1 HC + Anti-EGFR1 LC - TGFβRII | Expression constructs # 1 C and 4 C | CHO | 0.10 |
| FMab3 | TGFβRII -Anti-EGFR1 HC + Anti-EGFR1 LC | Expression constructs # 2 C and 5 C | CHO | 0.09 |
| FMab4 | Anti-EGFR1 HC + TGFβRII - Anti-EGFR1 LC | Expression constructs # 1 C and 6 C | CHO | 0.08 |
| FMab9 | Anti-EGFR1 HC-TGFβRII + Anti-EGFR1 LC -TGFβRII | Expression constructs # 3 C and 4 C | CHO | ND/VL |
| FMab10 | Anti-EGFR1 HC-TGFβRII + TGFβRII-Anti-EGFR1 LC | Expression constructs # 3 C and 6 C | CHO | 0.06 |
| FMab11 | TGFβRII-Anti-EGFR1 HC + Anti-EGFR1 LC - TGFβRII | Expression constructs # 4 C and 5 C | CHO | ND/VL |
| FMab12 | TGFβRII-Anti-EGFR1 HC + TGFβRII-Anti-EGFR1 LC | Expression constructs # 5 C and 6 C | CHO | 0.06 |

Purification of the Fusion Mabs supernatants using Protein A column:

The fusion monoclonal antibodies (Mabs) using recombinant protein producing CHO cell culture supernatant.

Procedure:

The procedure describes in detail the small scale purification process of IgG using C10/10 or XK26 column and using Mab Select Xtra affinity resin. The samples generated by this protocol can be used for various analysis Process Flow:

The culture supernatant secreted from recombinant cell line producing monoclonal antibodies or fusion monoclonal antibodies under sterile conditions were tested for titer and endotoxins;

The affinity chromatography using Mab Select Xtra Protein A resin was washed and equilibrated with binding buffer;

The pH of the supernatant was adjusted using 0.5M phosphate to the same pH has the column;

The supernatant was allowed to bind to the column/pass through the column at the flow rate of 0.5 ml/minute to achieve the maximum binding;

All the fusion Mabs binds through the Fc region and rest of the impurities passed pass through as flow through;

The column was washed with equilibration buffer;

The bound fusion Mabs were eluted using 0.1 M glycine pH 3.0;

The eluted proteins were adjusted back to neutral pH or the stable formulation pH;

The purified proteins were stored at −20° C. or at 2-8° C. depending on the stability.

Figure 22:
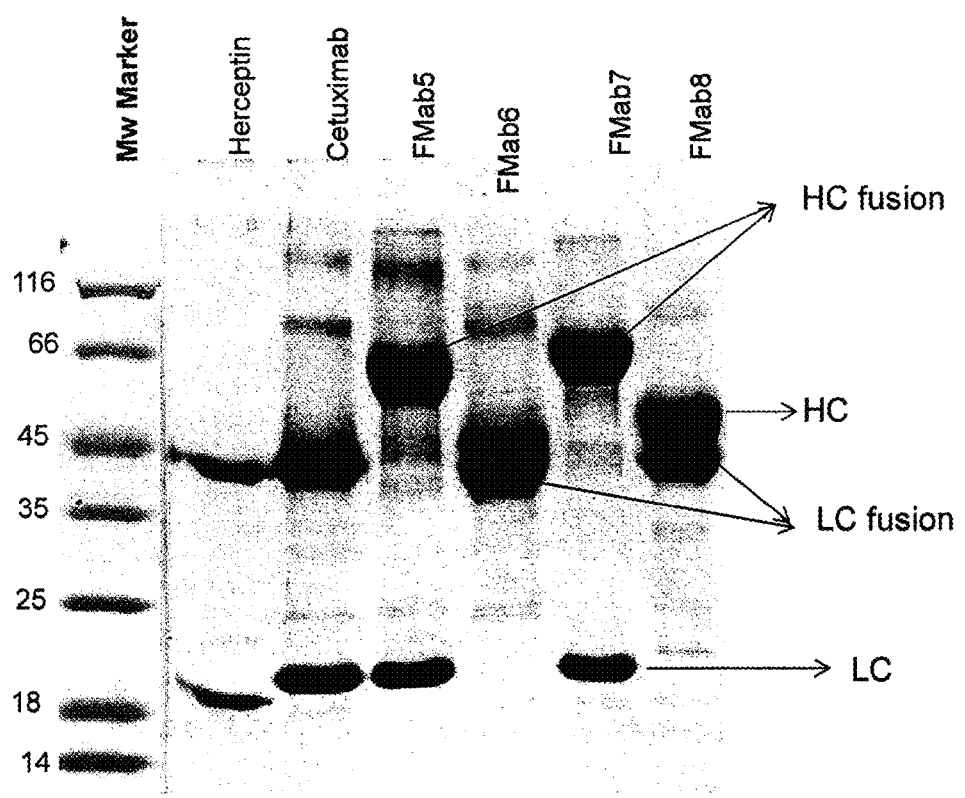
FIG. 22 shows ProteinA purified samples analyzed on 12% reducing SDS-PAGE.

Analysis of Protein A purified Fusion Mabs using SDS PAGE:

The transfected supernatants obtained were purified using proteinA affinity column. Later these were analyzed on reducing and non-reducing SDS-PAGE to find out the integrity of the molecule, as shown in FIG. 22, where in the proteinA purified samples were analyzed on 12% reducing SDS-PAGE. As expected all the fusion partners are giving the expected pattern on SDS-PAGE. The LC fusion and HC are running closely but the bands are separated. This higher mobility may be due to the 8 N-glycosylation sites (TGBRII 3*2=6+2 on LC)

Figure 23:
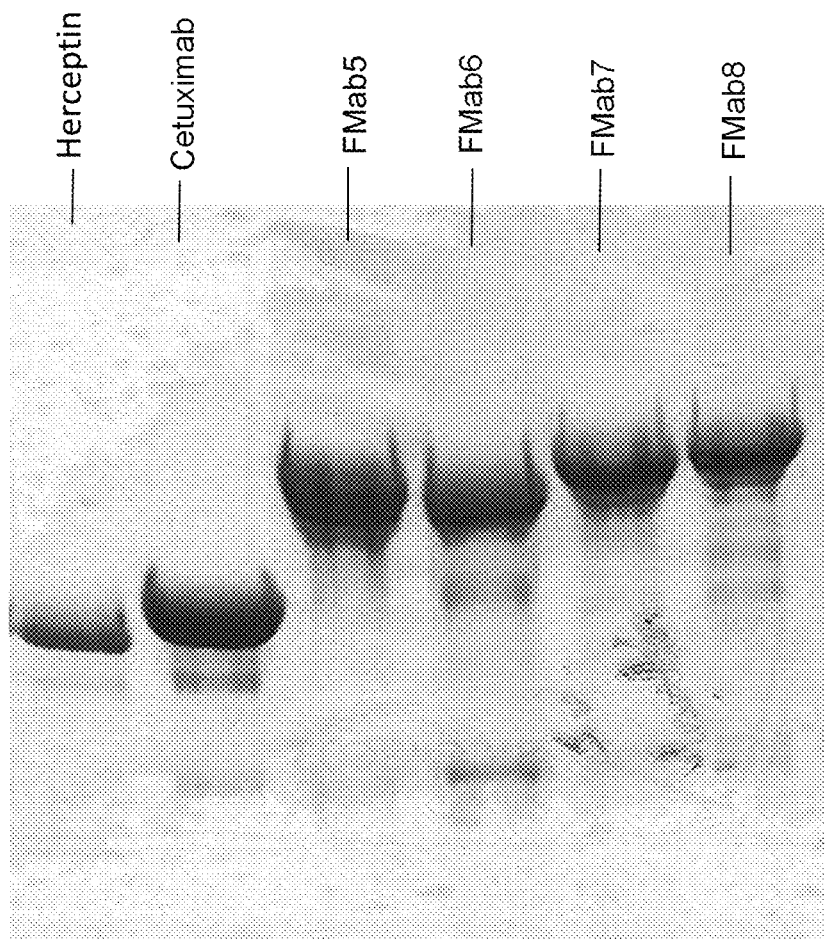
FIG. 23 shows ProteinA purified samples analyzed on 6% non-reducing SDS-PAGE.

FIG. 23 shows the results of the ProteinA purified samples that were analyzed on 6% non-reducing SDS-PAGE and although the amino acid composition is same, there is a difference in mobility. It may be due to the variable levels of glycosylation pattern based on the TGFβRII position and access in the molecule.

3. Anti-CTLA4-PD1 Fusion Protein Constructs for Cancer Targets.

Immunohistochemical analysis of freshly isolated tumor samples from patients with ovarian, lung, and breast cancers, renal cell carcinoma, squamous cell carcinoma of the head and neck, esophageal carcinoma, glioblastoma, thymoma, colon carcinoma, pancreatic and melanoma found that the vast majority express B7-H1 (see Flies 2011; Nomi 2007). Several pre-clinical studies have demonstrated increased tumor rejection by blocking PD1-PDL1 interaction. Recently, anti-PD1 and PD-L1 based therapies have demonstrated considerable activity in melanoma and some other solid tumors confirming their application as one of the most promising anti-cancer therapies.

Although, anti-CTLA4 may allow co-stimulation of T cells, they may still be inhibited by PD-L1-PD-1 interaction. This may be one of the reasons for only a minority of patients having response to anti-CTLA4 antibody. Fusion antibody of both anti-CTLA4 and PD1 are more efficacious than either agent alone since anti-CTLA4 allows T cell co-stimulation whereas PD1 binds to PD-L1 on tumor cells to negate the immunosuppression of T cells in tumor microenvironment. This may even be safer than the anti-CTLA4 because the lone use of anti-CTLA4 has led to immune breakthrough adverse events.

malian expression vectors. The expression of anti-CTLA4-PD1 fusion proteins using the constructs as set forth in FIG. 33.

Figure 33:
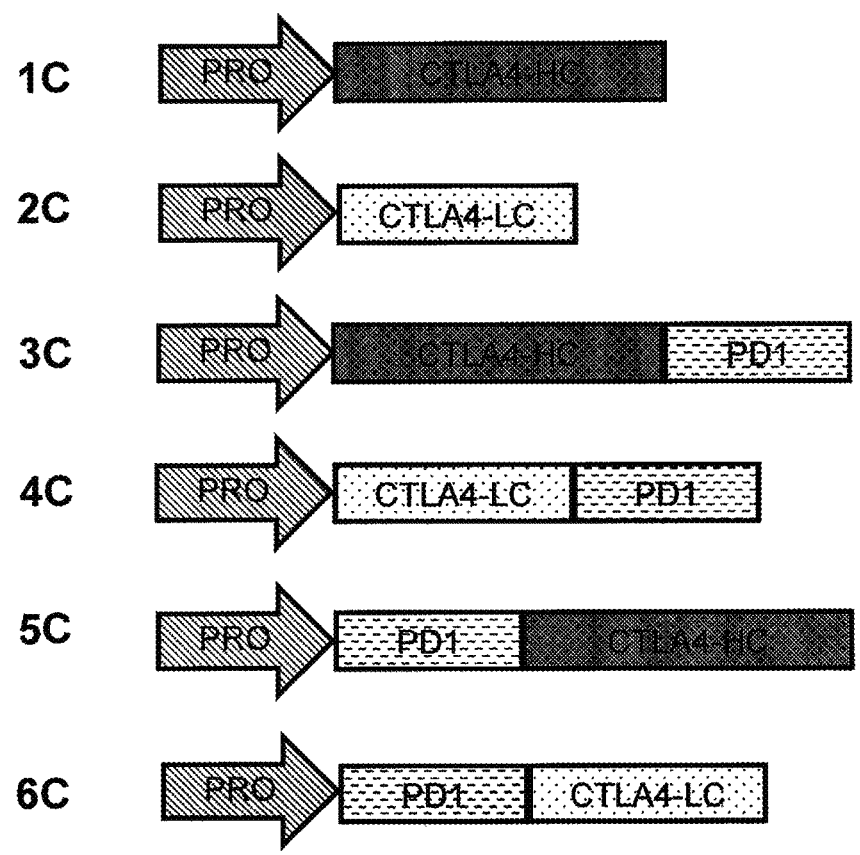
FIG. 33 shows expression constructs developed using the cDNAs as set forth in SEQ ID NOs: 7, 5 and 6.

The expression constructs developed and shown in FIG. 33 were transfected in the following combination into CHO cells (Table 6) to produce the following fusion proteins. The titer obtained for each constructs are mentioned in the last column.

TABLE 6

| Sl. No. | Fusion protein Name | Expression constructs combination transfected | Cell line used | Titer g/L |
| --- | --- | --- | --- | --- |
| FMab 13 | Anti-CTLA4 HC-PD1 + Anti-CTLA4 LC | Expression constructs # 2C and 3 C | CHO | 0.175 |
| FMab 14 | Anti-CTLA4 HC + Anti-CTLA4 LC-PD1 | Expression constructs # 1 C and 4 C | CHO | 0.221 |
| FMab 15 | PD1-Anti-CTLA4 HC + Anti-CTLA4 LC | Expression constructs # 2 C and 5 C | CHO | 0.029 |
| FMab 16 | Anti-CTLA4 HC + PD1-Anti-CTLA4 LC | Expression constructs # 1 C and 6 C | CHO | 0.021 |
| FMab 17 | Anti-CTLA4 HC-PD1 + Anti-CTLA4 LC-PD1 | Expression constructs # 3 C and 4 C | CHO | 0.137 |
| FMab 18 | Anti-CTLA4 HC-PD1 + PD1-Anti-CTLA4 LC | Expression constructs # 3 C and 6 C | CHO | 0.012 |
| FMab 19 | PD1-Anti-CTLA4 HC + Anti-CTLA4 LC-PD1 | Expression constructs # 4 C and 5 C | CHO | 0.029 |
| FMab 20 | PD1-Anti-CTLA4 HC + PD1-Anti-CTLA4 LC | Expression constructs # 5 C and 6 C | CHO | 0.014 |

Figure 24:
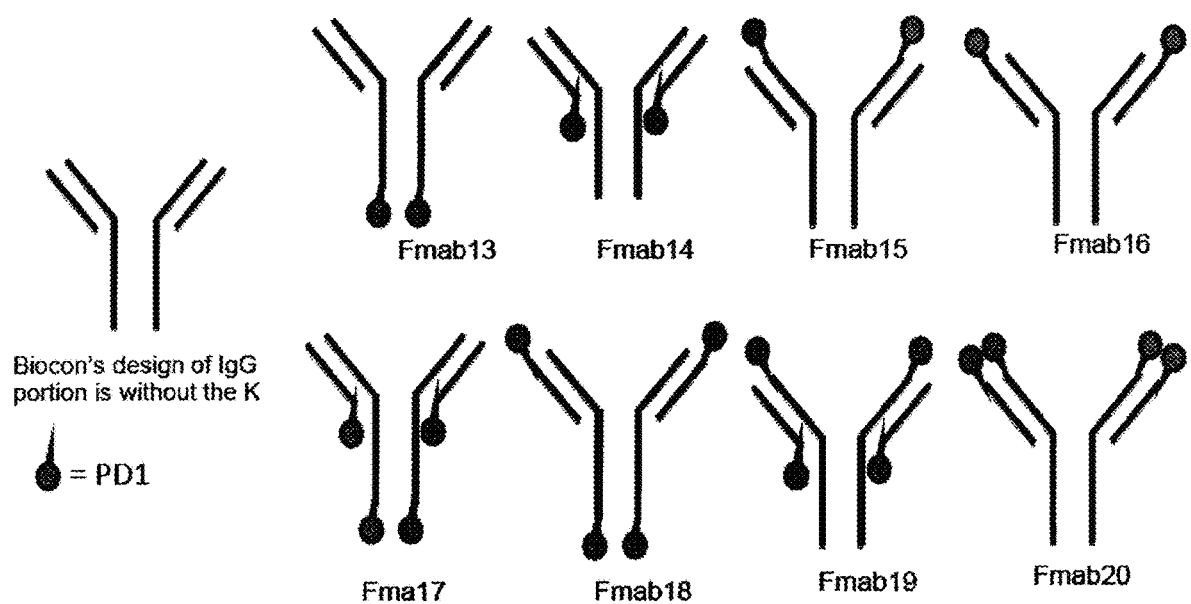
FIG. 24 shows the different possibilities for placement of the PD1 molecule on the anti-CTLA4 antibody.

Design and Selection of the Molecules:

The objective is to design the antibody fusion molecules which have duel therapeutic properties. On one hand the molecule should retain the complete activity of the anti-CTLA4 (Ipilimumab) and in parallel; it should have the PD L1 receptor binding activity in the tumor environment. The complete amino acid sequence of the anti-CTLA4 IgG molecule was used except the removal of the lysine at the C-terminus of the heavy chain. A 15 amino acid linker was positioned between the PD1 and Anti-CTLA4. The following combinations of constructs, as set forth in Table 5, were designed as shown in FIG. 24. The details of the above fusion protein constructs are given below.

TABLE 5

Figure 21:
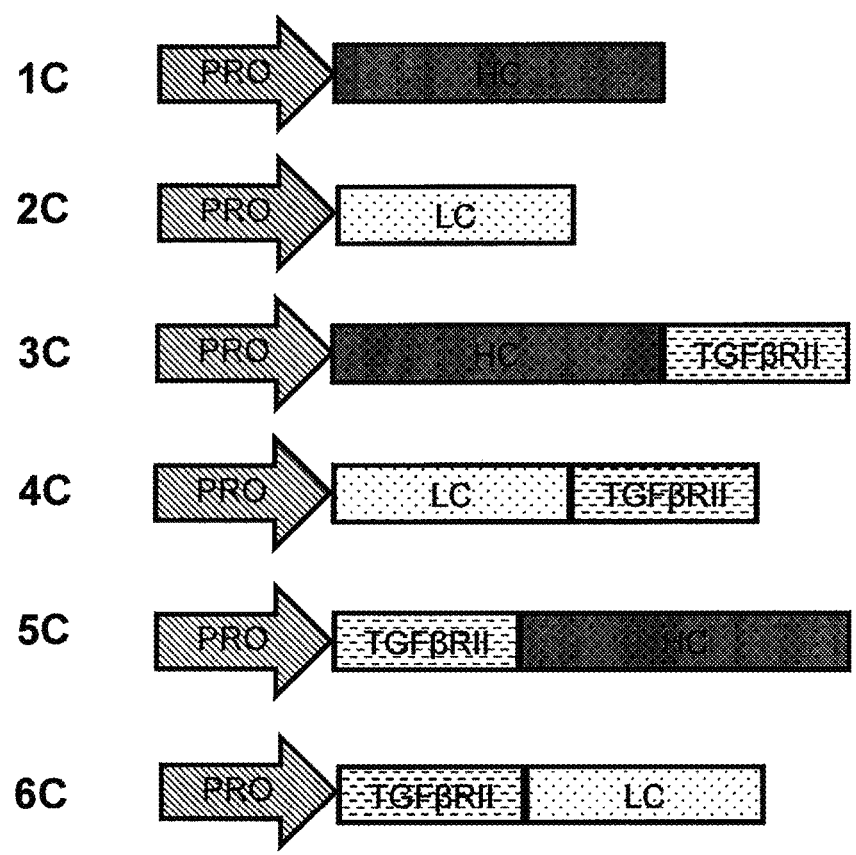
FIG. 21 shows expression constructs developed using the cDNAs as set forth in SEQ ID NOs: 1, 2 and 3.

| Constructs. no. | Fusion Mabs name |
| --- | --- |
| FMab13 | Anti-CTLA4 HC-PD1 + Anti-CTLA4 LC |
| FIG. 21 | (AA sequences in FIG. 25, SEQ ID NO: 32 and 14) |
| FMab14 | Anti-CTLA4 HC + Anti-CTLA4 LC-PD1 |
| FIG. 21 | (AA sequences in FIG. 26, SEQ ID NO: 13 and 33) |
| FMab15 | PD1-Anti-CTLA4 HC + Anti-CTLA4 LC |
| FIG. 21 | (AA sequences in FIG. 27, SEQ ID NO: 34 and 14) |
| FMab16 | Anti-CTLA4 HC + PD1-Anti-CTLA4 LC |
| FIG. 21 | (AA sequences in FIG. 28, SEQ ID NO: 13 and 35) |
| FMab17 | Anti-CTLA4 HC-PD1 + Anti-CTLA4 LC-PD1 |
| FIG. 21 | (AA sequences in FIG. 29, SEQ ID NO: 32 and 33) |
| FMab18 | Anti-CTLA4 HC-PD1 + PD1-Anti-CTLA4 LC |
| FIG. 21 | (AA sequences in FIG. 30, SEQ ID NO: 32 and 35) |
| FMab19 | PD1-Anti-CTLA4 HC + Anti-CTLA4 LC-PD1 |
| FIG. 21 | (AA sequences in FIG. 31, SEQ ID NO: 34 and 33) |
| FMab20 | PD1-Anti-CTLA4 HC + PD1-Anti-CTLA4 LC |
| FIG. 21 | (AA sequences in FIG. 32, SEQ ID NO: 34 and 35) |

Expression of the Above Fusion Constructs in CHO Cells:

The complete nucleotide sequence of the Anti-CTLA4-PD1 individual domains were codon optimized for expression in CHO cells (SEQ ID NOs: 7, 4, 5 and 6). The cDNAs were synthesized. The constructs were assembled in mam- Purification of and Characterization of Fusion Proteins:

The procedure describes the use of small scale purification process of IgG using C10/10 or XK26 column and using Mab Select Xtra affinity resin. The samples generated by this protocol can be used for various analysis.

Process Flow:

The culture supernatant secreted from recombinant cell line producing monoclonal antibodies or fusion monoclonal antibodies under sterile conditions were tested for titer and endotoxins;

The affinity chromatography using Mab Select Xtra ProteinA resin was washed and equilibrated with binding buffer;

The pH of the supernatant was adjusted using 0.5M phosphate to the same PH has the column;

The supernatant was allowed to bind to the column/pass through the column at the flow rate of 0.5 ml/minute to achieve the maximum binding;

All the fusion Mabs binds through the Fc region and rest of the impurities passed through as flow through;

The column was washed with equilibration buffer;

The bound fusion Mabs were eluted using 0.1 M glycine pH 3.0;

The eluted proteins were adjusted back to neutral pH or the stable formulation pH; and The purified proteins are stored at −20° C. or at 2-8° C. depending on the stability.

4. Anti-EGFR1 HC-TGFβRII+Anti-EGFR1 LC (Fmab 1) Binding ELISAs-Procedure:

The fusion Mab was tested for its ability to bind to its targets in three different ELISAs: 1) EGFR1 target-binding ELISA, 2) TGFβ-target binding ELISA and 3) Bifunctional ELISA.

For the target binding ELISAs, the targets (rhEGFR-Fc chimera or TGFβ) were coated onto NUNC maxisorb plates overnight at 4° C. The plates were washed and then blocked with superblock at room temperature for 2 hr. Different dilutions of the fusion Mab or the negative control antibody was added to the plate. The plate was incubated at room temperature for 1 hr. Binding of the fusion Mab was detected by the addition of a biotinylated anti-human IgG F(ab)$_2$ secondary antibody, followed by a 1 hr incubation with peroxidase-conjugated streptavidin at room temperature. TMB substrate solution was added and the reaction stopped with 1N H$_2$SO$_4$. The absorbance was measured at 450 nm on a BioTek Synergy H4 Hybrid reader.

For the bifunctional ELISA, rhEGFR-Fc chimera was coated onto NUNC maxisorb plates overnight at 4° C. The plates were washed and then blocked with superblock at room temperature for 2 hr. Different dilutions of the fusion Mab or the negative control antibody was added to the plate. The plate was incubated at room temperature for 1 hr. After washing, TGFβ was added and the plate was incubated at room temperature for 1 hr. The plate was washed and anti-TGFβ-biotin was added and the plate incubated at room temperature for 1 hr. The plate was washed and streptavidin-HRP was added and the plate incubated at room temperature for 1 hr. After washing, TMB substrate solution was added and the reaction stopped with 1N H$_2$SO$_4$. The absorbance was measured at 450 nm on a BioTek Synergy H4 Hybrid reader.

Figure 34:
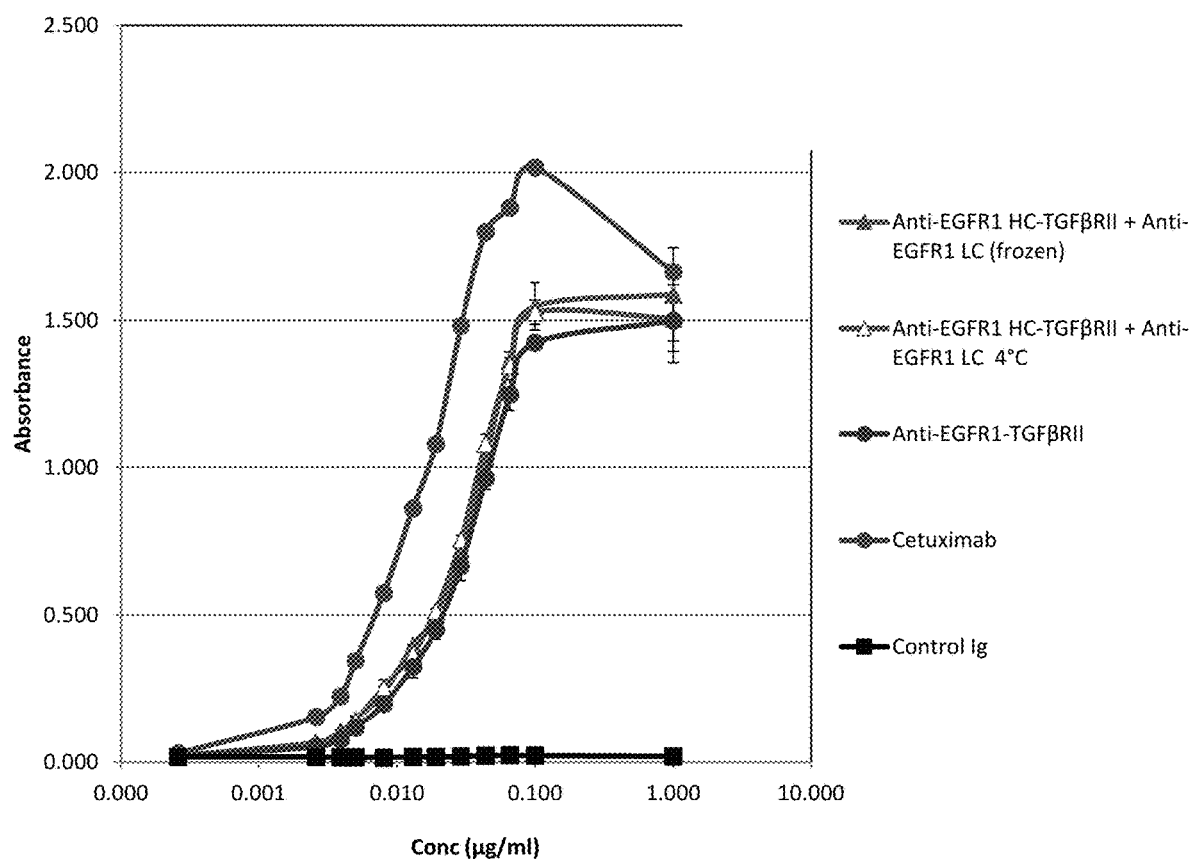
FIG. 34 shows EGFR1 target binding ELISA. The Anti-EGFR1 HC-TGFβRII+Anti-EGFR1 LC fusion Mab binds to its immobilized target EGFR1.
Figure 35:
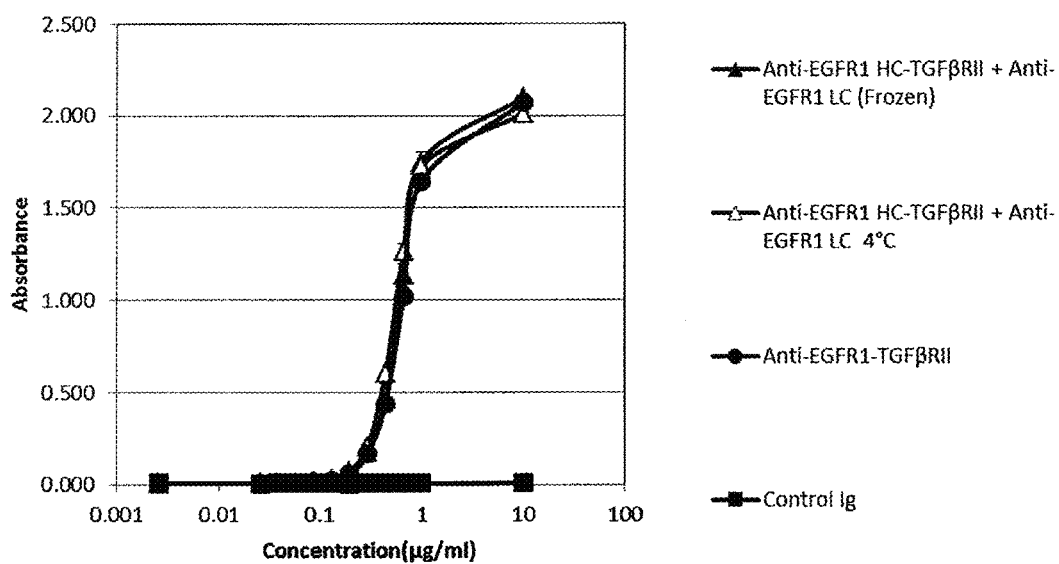
FIG. 35 shows TGFβ target binding ELISA. The Anti-EGFR1 HC-TGFβRII+Anti-EGFR1 LC fusion Mab binds to its target TGFβ.
Figure 36:
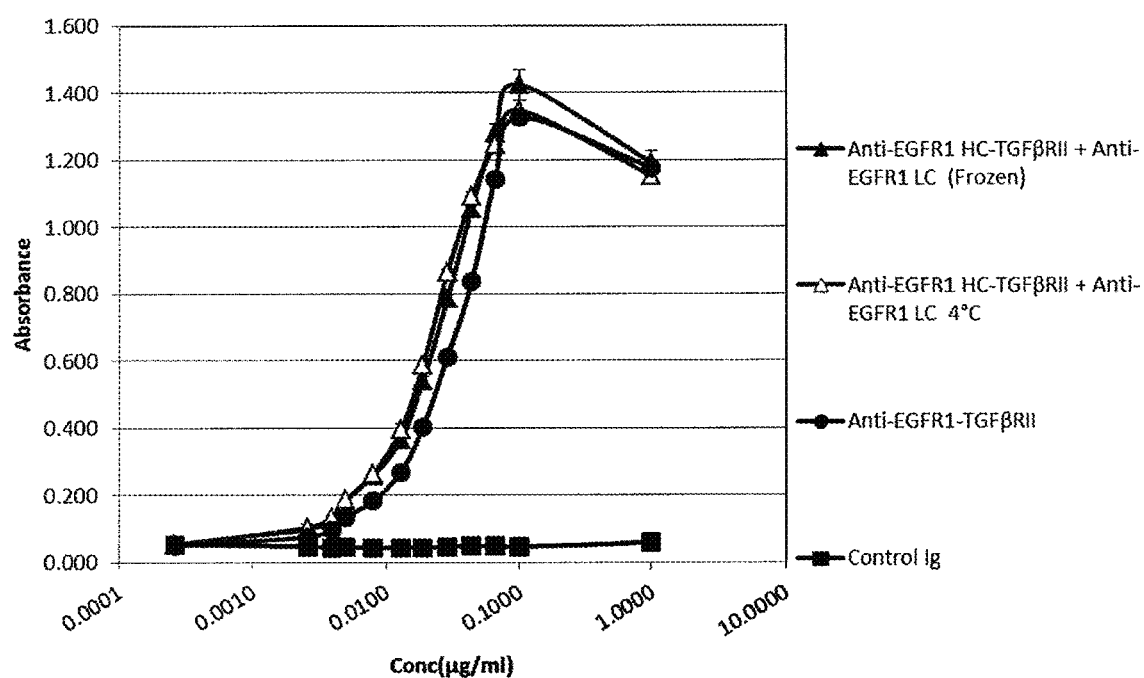
FIG. 36 shows Bifunctional ELISA. The anti-EGFR1 HC-TGFβRII+Anti-EGFR1 LC fusion Mab binds to both its target EGFR1 and TGFβ at the same time.

Results:

The binding of the anti-EGFR1 HC-TGFβRII+Anti-EGFR1 LC fusion Mab to both the targets EGFR1 (FIG. 34) and TGFβ (FIG. 35) was comparable with anti-EGFR1-TGFβRII. The anti-EGFR1 HC-TGFβRII+Anti-EGFR1 LC fusion Mab was also tested in a bifunctional ELISA to determine whether the anti-EGFR1 and TGFβRII domains of the Mab can bind to their respective targets without interfering with each other. As seen in FIG. 36, the anti-EGFR1 HC-TGFβRII+Anti-EGFR1 LC fusion Mab binds to both its targets, suggesting that there is no interference in binding to either target dues to the construction of the fusion Mab.

Binding to Cells Expressing EGFR1:

Procedure:

A-431 cells were grown in flasks until they reached 70-80% confluency. The cells were trypsinized and harvested. The cells were stained with different dilutions of the anti-EGFR1 HC-TGFβRII+Anti-EGFR1 LC fusion Mab or control Ig at 2-8° C. for 30 minutes. The cells were washed and incubated with anti-Human IgG-FITC conjugate at 2-8° C. for 30 minutes. After washing, the cells were analyzed on a flow cytometer. Live cells were gated based on their FSC vs SSC profiles. The total MFI for the gated population were recorded.

Figure 37:
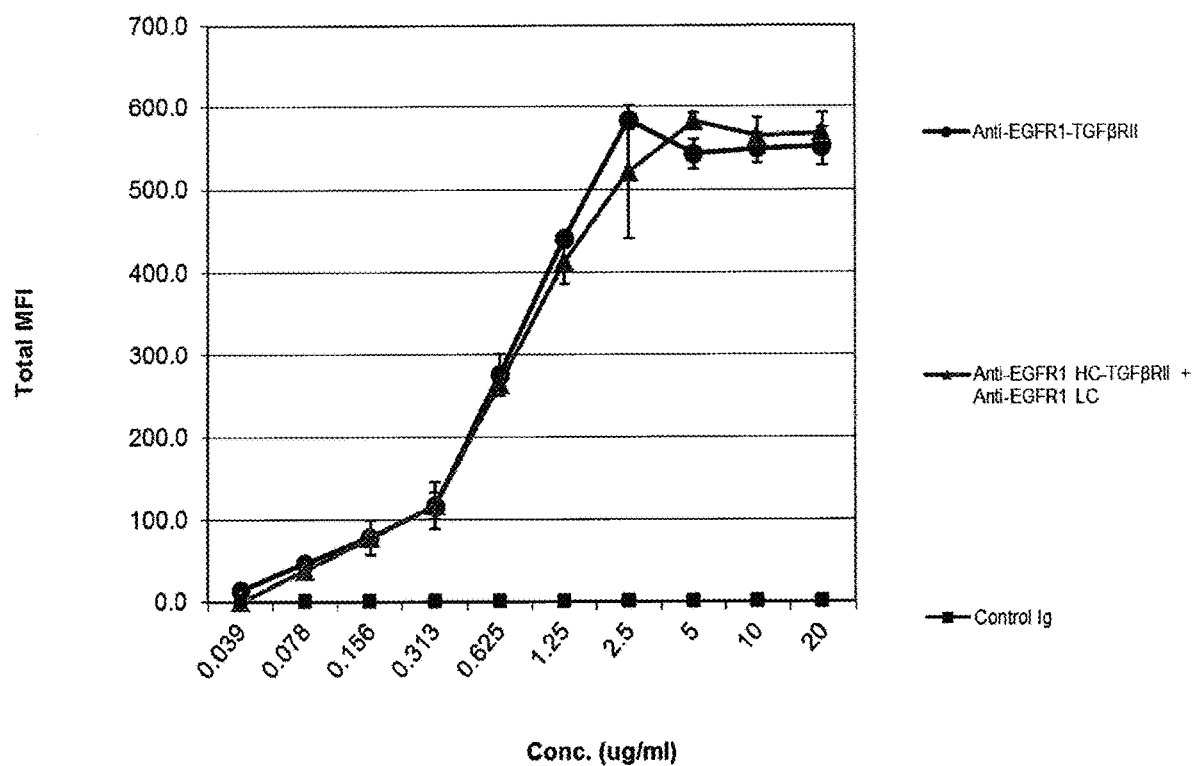
FIG. 37 shows flow cytometric analysis of the binding of the anti-EGFR1 HC-TGFβRII+Anti-EGFR1 LC fusion Mab to EGFR1-expressing A431 cells.

Results:

The anti-EGFR1 HC-TGFβRII+Anti-EGFR1 LC fusion binds to EGFR-expressing A-431 cells in a dose dependent manner (FIG. 37). The binding of anti-EGFR1 HC-TGFβRII+Anti-EGFR1 LC is comparable to the binding of anti-EGFR1-TGFβRII.

Antibody-Dependent Cytotoxicity Activity

Procedure:

A-431 cells were grown in flasks until they reached 70-80% confluency. The cells were trypsinized, harvested and plated into 96-well plates. The cells were labeled with different dilutions of the anti-EGFR1 HC-TGFβRII+Anti-EGFR1 LC fusion Mab or control Ig at 2-8° C. for 30 minutes. The labeled cells were co-incubated with freshly isolated human PBMC at 37° C., 5% CO$_2$ for 24 hours. Cytotoxicity was measured using the Cyto-Tox-Glo cytotoxicity assay kits.

Figure 38:
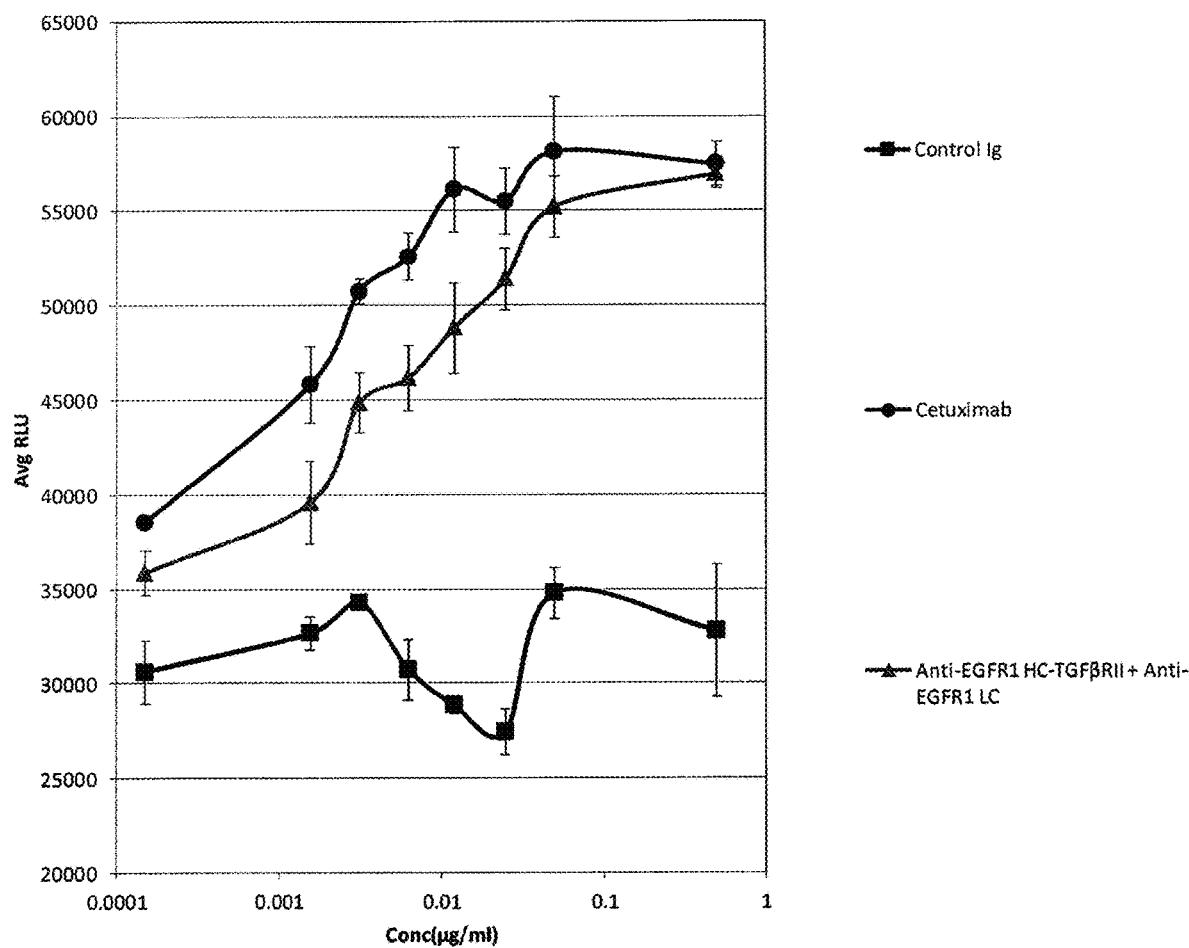
FIG. 38 shows ADCC against EGFR1-expressing A-431 cells. Anti-EGFR1 HC-TGFβRII+Anti-EGFR1 LC fusion Mab mediates ADCC against EGFR1-expressing A-431 cells and the effect is dose dependent.

Results:

The anti-EGFR1 HC-TGFβRII+Anti-EGFR1 LC fusion mediates ADCC of EGFR-expressing A-431 cells by human PBMC effector cells. The ADCC is dose dependent (FIG. 38). These results suggest that the Fc portion of the fusion Mab is intact and functional.

Inhibition of Proliferation

Procedure:

A-431 cells were grown in flasks until they reached 70-80% confluency. The cells were trypsinized, harvested and plated into 96-well plates. Different dilutions of the anti-EGFR1 HC-TGFβRII+Anti-EGFR1 LC fusion Mab or control Ig were added to the cells. The plates were incubated at 37° C., 5% CO$_2$ for three days. On the third day, cell proliferation was measured by the AlamarBlue method.

Figure 39:
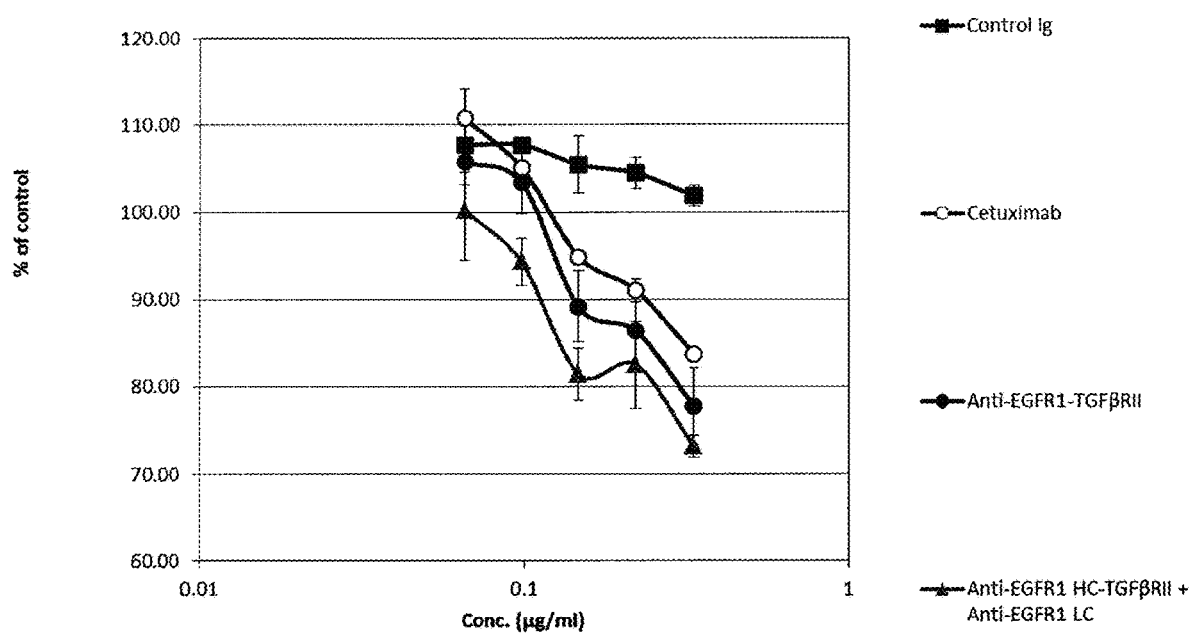
FIG. 39 shows Inhibition of proliferation assay. Anti-EGFR1 HC-TGFβRII+Anti-EGFR1 LC fusion Mab inhibits the proliferation of EGFR1-expressing A-431 cells.

Results:

Anti-EGFR antibodies such as Cetuximab are known to inhibit the proliferation of EGFR1-expressing cells. As seen in FIG. 39, the anti-EGFR portion of the anti-EGFR1 HC-TGFβRII+Anti-EGFR1 LC fusion Mab is intact and has anti-proliferative activity.

5. Anti-EGFR1 HC+Anti-EGFR1 LC-TGFβRII (Fmab2)

Binding ELISAs: Procedure:

The anti-EGFR1 HC+Anti-EGFR1 LC-TGFβRII fusion Mab was tested for its ability to bind to its targets in three different ELISAs: 1) EGFR1 target-binding ELISA, 2) TGFβ-target binding ELISA and 3) Bifunctional ELISA.

For the target binding ELISAs, the targets (rhEGFR-Fc chimera or TGFβ) were coated onto NUNC maxisorb plates overnight at 4° C. The plates were washed and then blocked with superblock at room temperature for 2 hr. Different dilutions of the fusion Mab or the negative control antibody was added to the plate. The plate was incubated at room temperature for 1 hr. Binding of the fusion Mab was detected by the addition of a biotinylated anti-human IgG F(ab)$_2$ secondary antibody, followed by a 1 hr incubation with peroxidase-conjugated streptavidin at room temperature. TMB substrate solution was added and the reaction stopped with 1N H$_2$SO$_4$. The absorbance was measured at 450 nm on a BioTek Synergy H4 Hybrid reader.

For the bifunctional ELISA, rhEGFR-Fc chimera was coated onto NUNC maxisorb plates overnight at 4° C. The plates were washed and then blocked with superblock at room temperature for 2 hr. Different dilutions of the fusion Mab or the negative control antibody was added to the plate. The plate was incubated at room temperature for 1 hr. After washing, TGFβ was added and the plate is incubated at room temperature for 1 hr. The plate was washed and anti-TGFβ-biotin was added and the plate incubated at room temperature for 1 hr. The plate was washed and streptavidin-HRP was added and the plate incubated at room temperature for 1 hr. After washing, TMB substrate solution was added and the reaction stopped with 1N H$_2$SO$_4$. The absorbance was measured at 450 nm on a BioTek Synergy H4 Hybrid reader.

Figure 40:
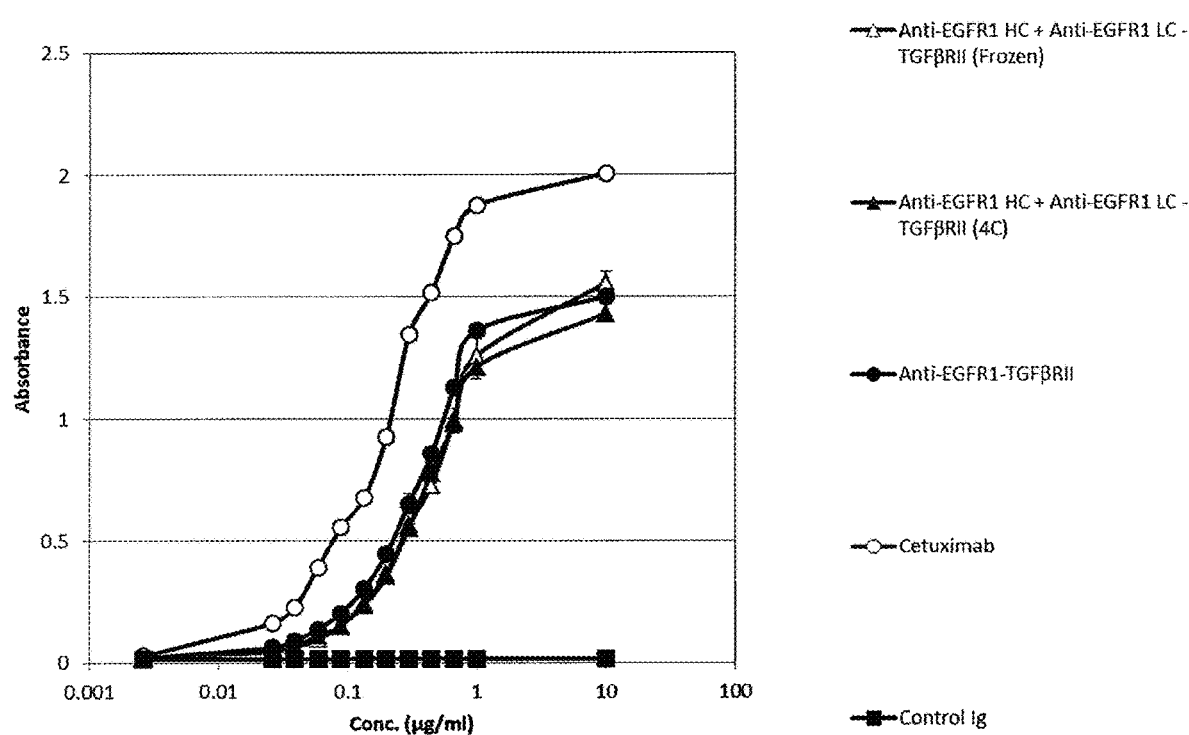
FIG. 40 shows EGFR1 target binding ELISA. The Anti-EGFR1 HC+Anti-EGFR1 LC-TGFβRII fusion Mab binds to its immobilized target EGFR1.
Figure 41:
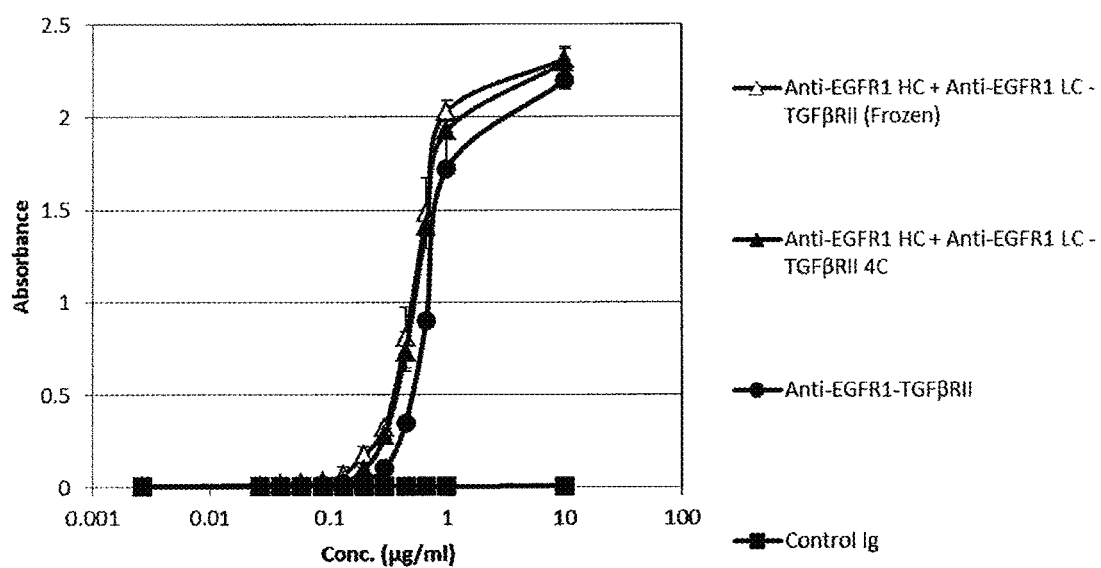
FIG. 41 shows TGFβ target binding ELISA. The anti-EGFR1 HC+Anti-EGFR1 LC-TGFβRII fusion Mab binds to its target TGFβ.
Figure 42:
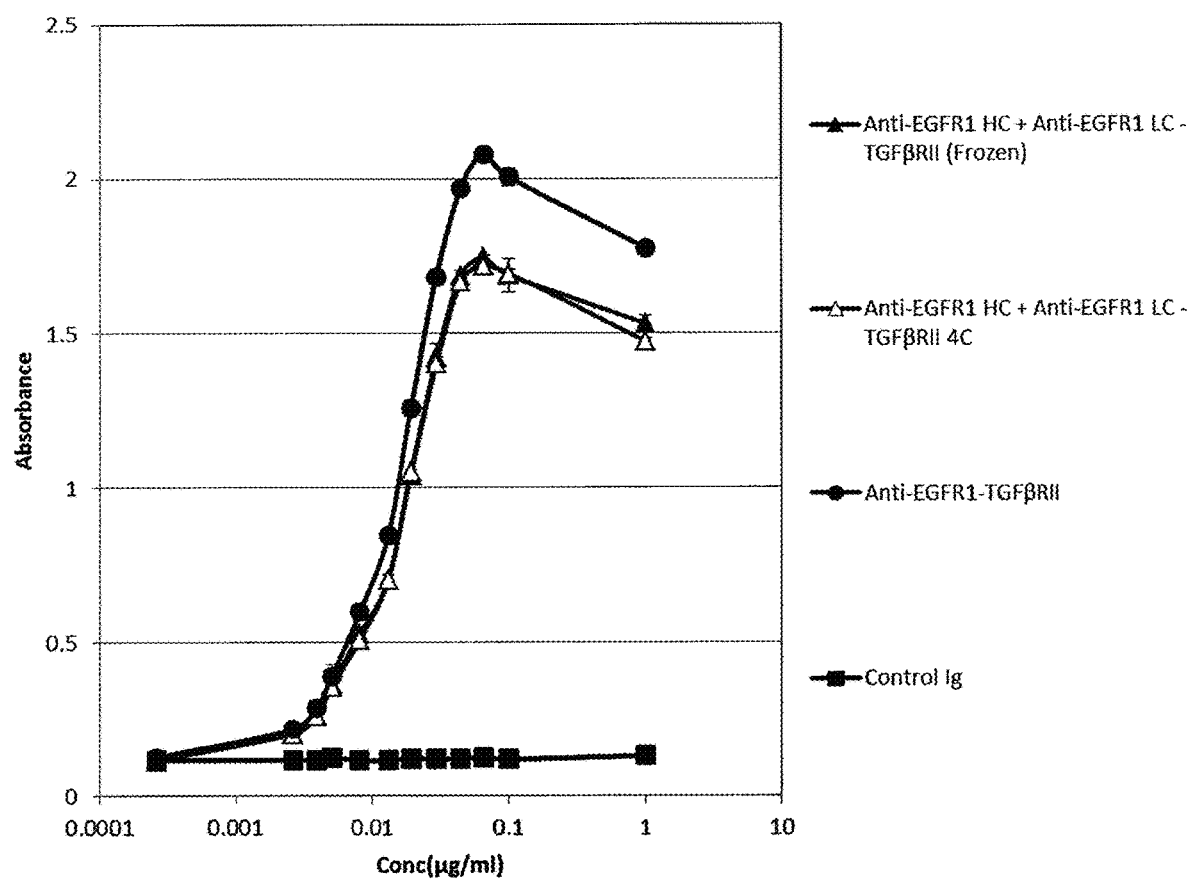
FIG. 42 shows Bifunctional ELISA. The anti-EGFR1 HC+Anti-EGFR1 LC-TGFβRII fusion Mab binds to both its target EGFR1 and TGFβ at the same time.

Results:

The binding of anti-EGFR1 HC+Anti-EGFR1 LC-TGFβRII fusion Mab to both the targets EGFR1 (FIG. 40) and TGFβ (FIG. 41) was comparable to anti-EGFR1-TGFβRII. The anti-EGFR1 HC+Anti-EGFR1 LC-TGFβRII fusion Mab was also tested in a bifunctional ELISA to determine whether the anti-EGFR1 and TGFβRII domains of the Mab can bind to their respective targets without interfering with each other. As seen in FIG. 42, the anti-EGFR1 HC+Anti-EGFR1 LC-TGFβRII fusion Mab binds to both its targets, suggesting that there is no interference in binding to either target dues to the construction of the fusion Mab.

Figure 43:
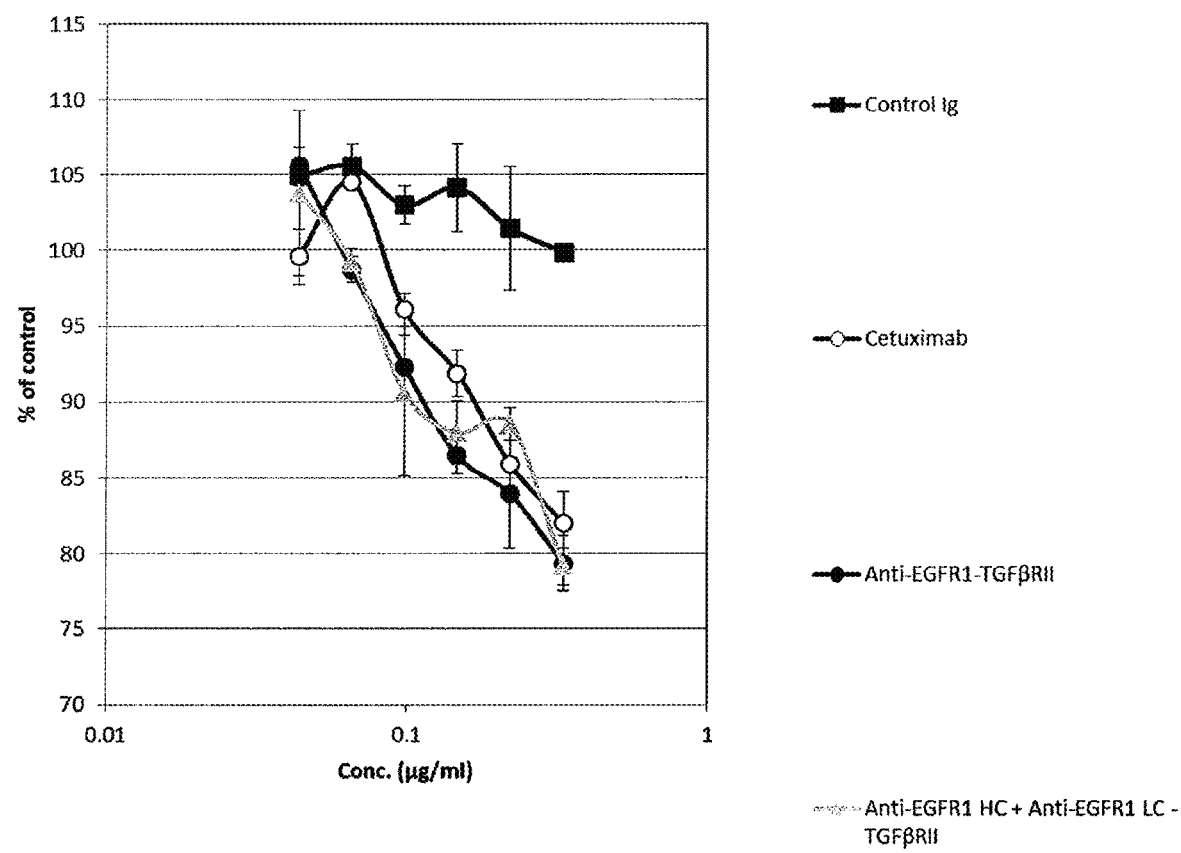
FIG. 43 shows Inhibition of proliferation assay. Anti-EGFR1 HC+Anti-EGFR1 LC-TGFβRII fusion Mab inhibits the proliferation of EGFR1-expressing A-431 cells.

Inhibition of Proliferation
Procedure:
A-431 cells were grown in flasks until they reached 70-80% confluency. The cells were trypsinized, harvested and plated into 96-well plates. Different dilutions of the anti-EGFR1 HC+Anti-EGFR1 LC-TGFβRII fusion Mab or control Ig were added to the cells. The plates were incubated at 37° C., 5% $CO_2$ for three days. On the third day, cell proliferation was measured by the AlamarBlue method.
Results:
Anti-EGFR antibodies such as Cetuximab are known to inhibit the proliferation of EGFR1-expressing cells. As seen in FIG. 43, the anti-EGFR portion of the anti-EGFR1 HC+Anti-EGFR1 LC-TGFβRII fusion Mab is intact and has anti-proliferative activity.

6. TGFβRII-Anti-EGFR1 HC+Anti-EGFR1 LC (Fmab 3)
Binding ELISAs: Procedure:
The fusion Mab was tested for its ability to bind to its targets in three different ELISAs: 1) EGFR1 target-binding ELISA, 2) TGFβ-target binding ELISA and 3) Bifunctional ELISA.

For the target binding ELISAs, the targets (rhEGFR-Fc chimera or TGFβ) were coated onto NUNC maxisorb plates overnight at 4° C. The plates were washed and then blocked with superblock at room temperature for 2 hr. Different dilutions of the fusion Mab or the negative control antibody was added to the plate. The plate was incubated at room temperature for 1 hr. Binding of the fusion Mab was detected by the addition of a biotinylated anti-human IgG F(ab)$_2$ secondary antibody, followed by a 1 hr incubation with peroxidase-conjugated streptavidin at room temperature. TMB substrate solution was added and the reaction stopped with 1N $H_2SO_4$. The absorbance was measured at 450 nm on a BioTek Synergy H4 Hybrid reader.

Figure 44:
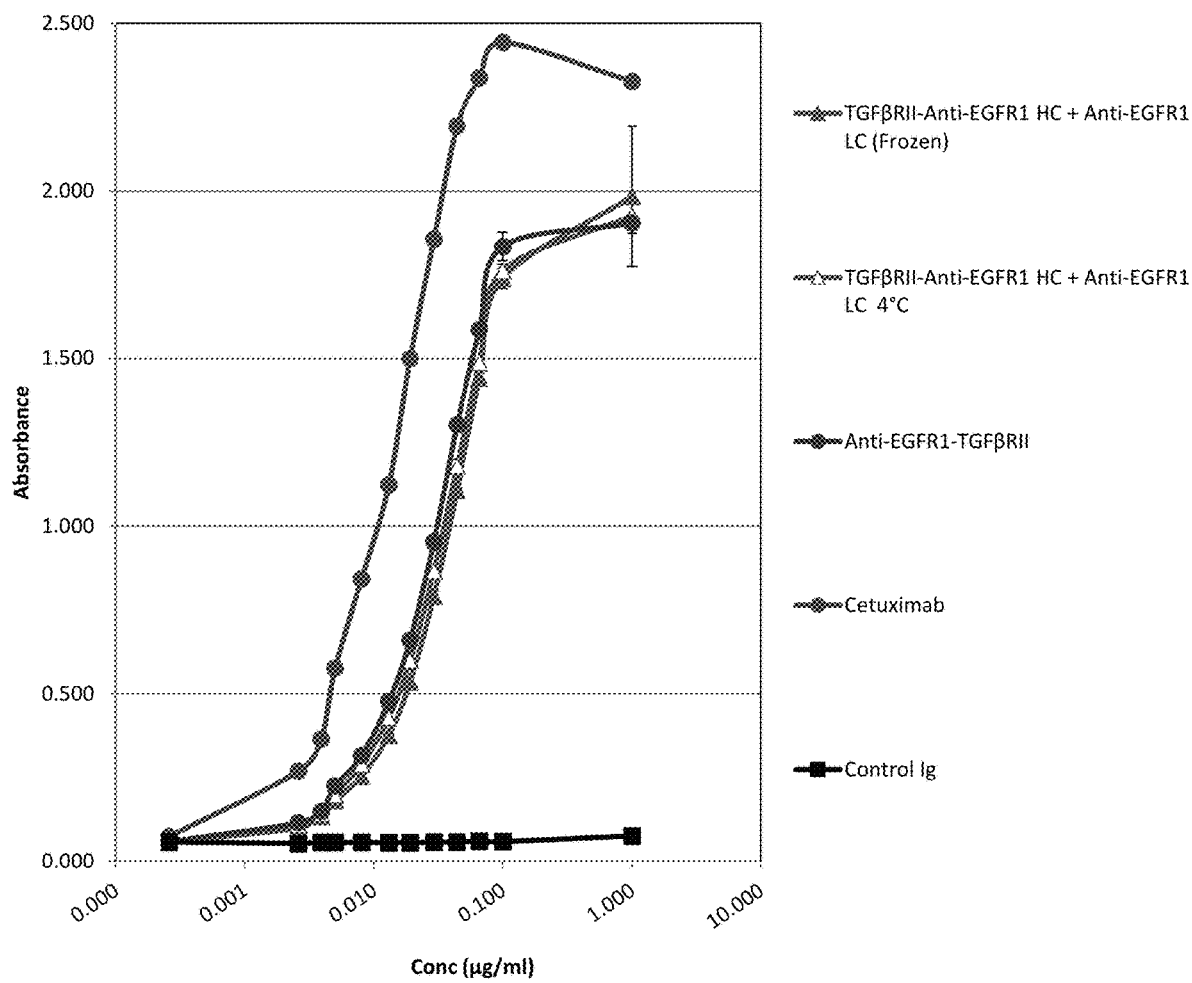
FIG. 44 shows EGFR1 target binding ELISA. The TGFβRII-Anti-EGFR1 HC+Anti-EGFR1 LC fusion Mab binds to its immobilized target EGFR1.
Figure 45:
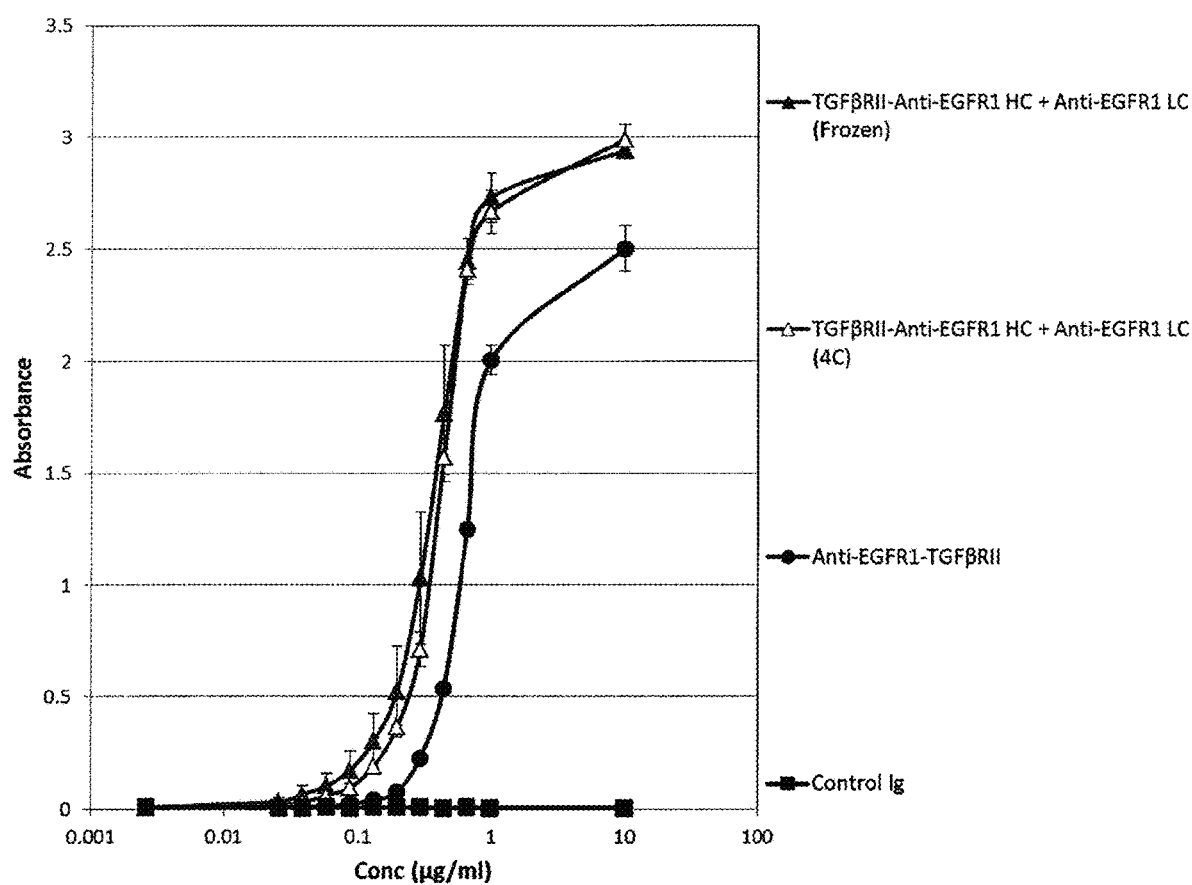
FIG. 45 shows TGFβ target binding ELISA. The TGFβRII-anti-EGFR1 HC+anti-EGFR1 LC fusion Mab binds to its target TGFβ.
Figure 46:
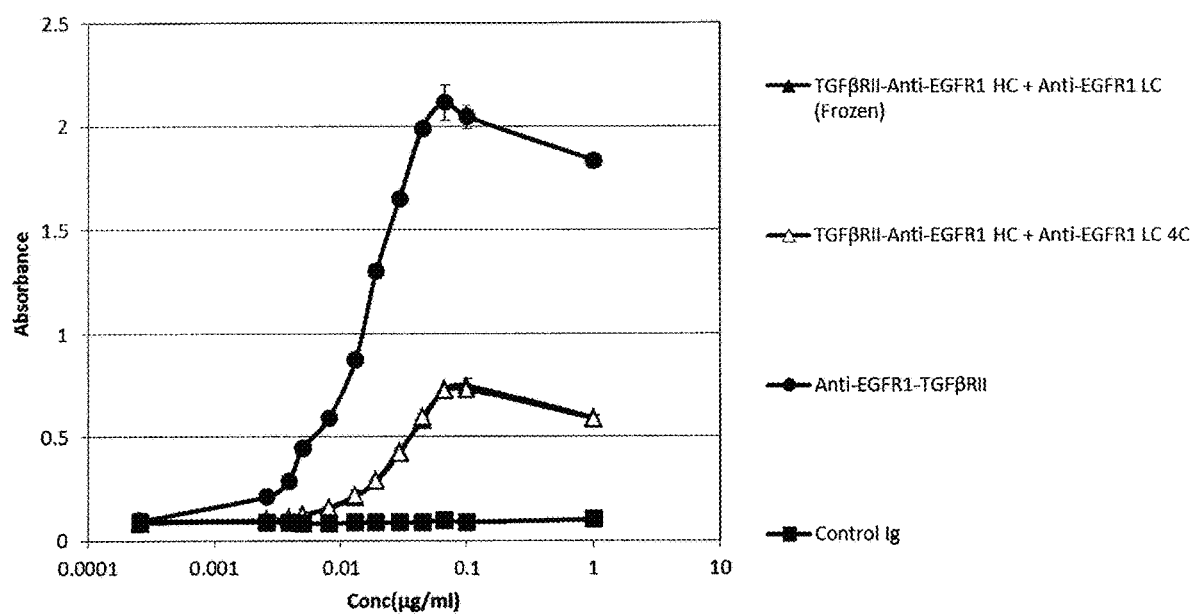
FIG. 46 shows Bifunctional ELISA. The TGFβRII-Anti-EGFR1 HC+Anti-EGFR1 LC fusion Mab binds to both its target EGFR1 and TGFβ at the same time.

For the bifunctional ELISA, rhEGFR-Fc chimera was coated onto NUNC maxisorb plates overnight at 4° C. The plates were washed and then blocked with superblock at room temperature for 2 hr. Different dilutions of the fusion Mab or the negative control antibody was added to the plate. The plate was incubated at room temperature for 1 hr. After washing, TGFβ was added and the plate was incubated at room temperature for 1 hr. The plate was washed and anti-TGFβ-biotin was added and the plate incubated at room temperature for 1 hr. The plate was washed and streptavidin-HRP was added and the plate incubated at room temperature for 1 hr. After washing, TMB substrate solution was added and the reaction stopped with 1N H2504. The absorbance was measured at 450 nm on a BioTek Synergy H4 hybrid reader.
Results:
The binding of the TGFβRII-Anti-EGFR1 HC+Anti-EGFR1 LC fusion Mab to both the targets EGFR1 (FIG. 44) and TGFβ (FIG. 45) was comparable to anti-EGFR1-TGFβRII. The TGFβRII-Anti-EGFR1 HC+Anti-EGFR1 LC fusion Mab was also tested in a bifunctional ELISA to determine whether the anti-EGFR1 and TGFβRII domains of the Mab can bind to their respective targets without interfering with each other. As seen in FIG. 46, the binding of TGFβRII-Anti-EGFR1 HC+Anti-EGFR1 LC fusion Mab is reduced as compared to anti-EGFR1-TGFβRII, suggesting that there is some interference in binding to either target due to the construction of the fusion Mab.

Binding to Cells Expressing EGFR1:
Procedure:
A-431 cells were grown in flasks until they reached 70-80% confluency. The cells were trypsinized and harvested. The cells were stained with different dilutions of the TGFβRII-Anti-EGFR1 HC+Anti-EGFR1 LC fusion Mab or control Ig at 2-8° C. for 30 minutes. The cells were washed and incubated with anti-Human IgG-FITC conjugate at 2-8° C. for 30 minutes. After washing, the cells were analyzed on a flow cytometer. Live cells were gated based on their FSC vs SSC profiles. The total MFI for the gated population were recorded.
Results:
The TGFβRII-Anti-EGFR1 HC+Anti-EGFR1 LC fusion binds to EGFR-expressing A-431 cells in a dose dependent manner. The binding of TGFβRII-Anti-EGFR1 HC+Anti-EGFR1 LC is comparable to the binding of anti-EGFR1-TGFβRII.

Figure 47:
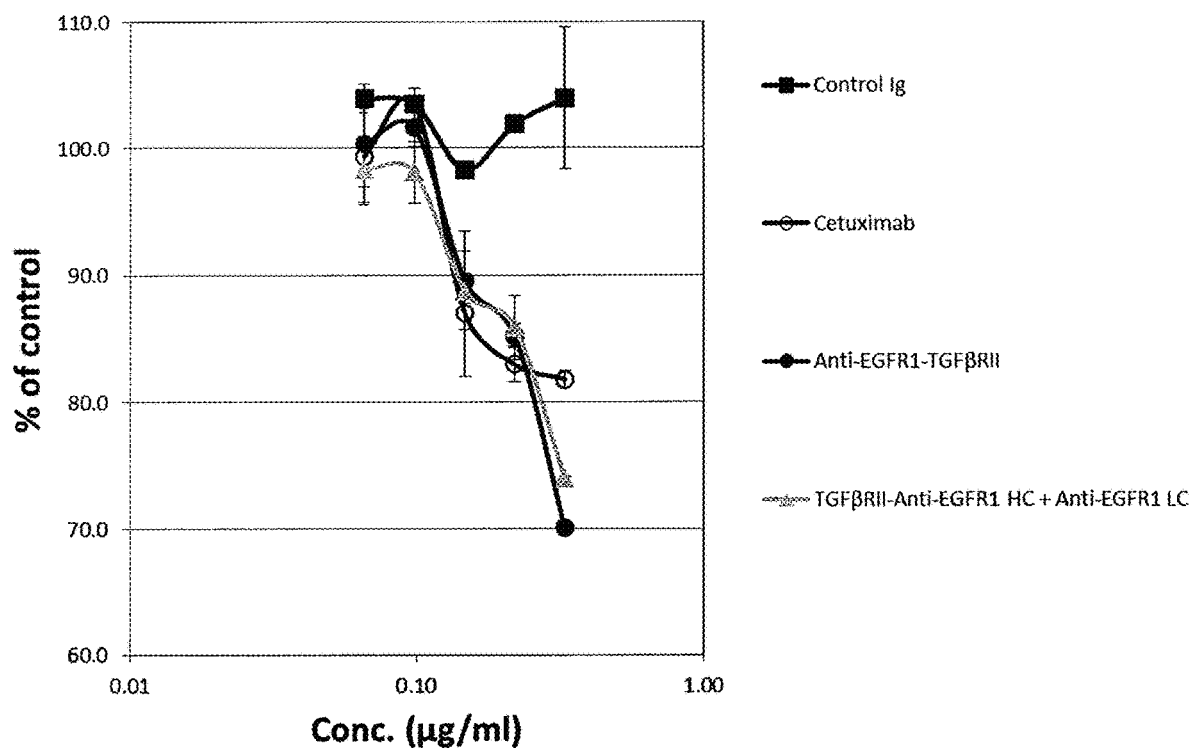
FIG. 47 shows Inhibition of proliferation assay. TGFβRII-Anti-EGFR1 HC+Anti-EGFR1 LC fusion Mab inhibits the proliferation of EGFR1-expressing A-431 cells.

Inhibition of Proliferation
Procedure:
A-431 cells were grown in flasks until they reached 70-80% confluency. The cells were trypsinized, harvested and plated into 96-well plates. Different dilutions of the TGFβRII-Anti-EGFR1 HC+Anti-EGFR1 LC fusion Mab or control Ig were added to the cells. The plates were incubated at 37° C., 5% $CO_2$ for three days. On the third day, cell proliferation was measured by the AlamarBlue method.
Results:
Anti-EGFR antibodies such as Cetuximab are known to inhibit the proliferation of EGFR1-expressing cells. As seen in FIG. 47, the anti-EGFR portion of the TGFβRII-Anti-EGFR1 HC+Anti-EGFR1 LC fusion Mab is intact and has anti-proliferative activity.

7. Anti-EGFR1 HC+TGFβRII-Anti-EGFR1 LC (Fmab 4)
Binding ELISAs: Procedure:
The fusion Mab was tested for its ability to bind to its targets in three different ELISAs: 1) EGFR1 target-binding ELISA, 2) TGFβ-target binding ELISA and 3) Bifunctional ELISA.

For the target binding ELISAs, the targets (rhEGFR-Fc chimera or TGFβ) were coated onto NUNC maxisorb plates overnight at 4° C. The plates were washed and then blocked with superblock at room temperature for 2 hr. Different dilutions of the fusion Mab or the negative control antibody was added to the plate. The plate was incubated at room temperature for 1 hr. Binding of the fusion Mab was detected by the addition of a biotinylated anti-human IgG F(ab)$_2$ secondary antibody, followed by a 1 hr incubation with peroxidase-conjugated streptavidin at room temperature. TMB substrate solution was added and the reaction stopped with 1N $H_2SO_4$. The absorbance was measured at 450 nm on a BioTek Synergy H4 Hybrid reader.

Figure 48:
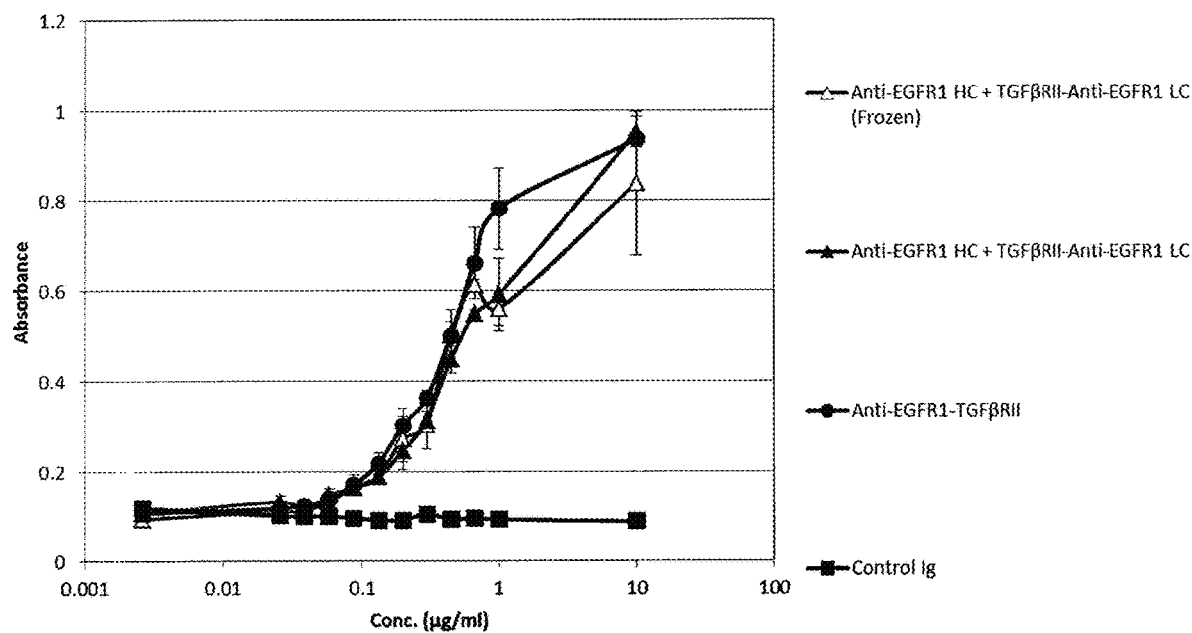
FIG. 48 shows EGFR1 target binding ELISA. The Anti-EGFR1 HC+TGFβRII-Anti-EGFR1 LC fusion Mab binds to its immobilized target EGFR1.
Figure 49:
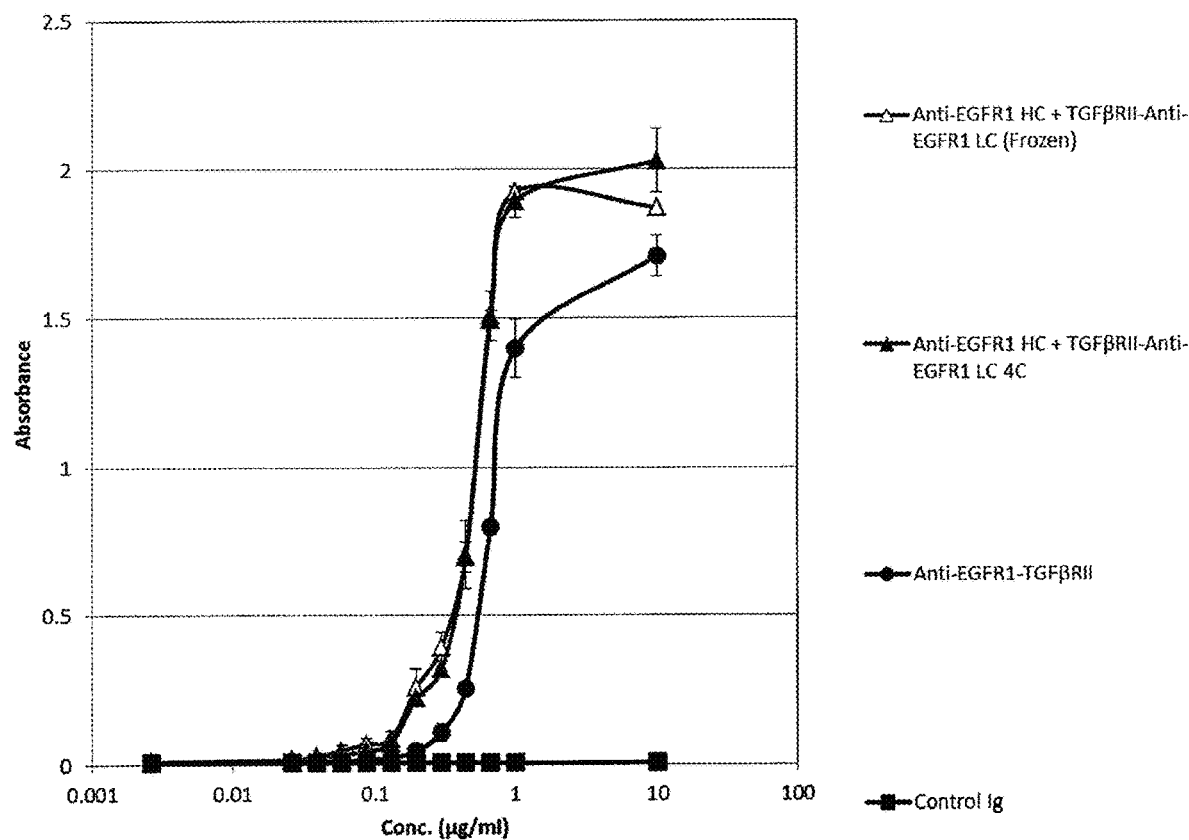
FIG. 49 shows TGFβ target binding ELISA. The Anti-EGFR1 HC+TGFβRII-Anti-EGFR1 LC fusion Mab binds to its target TGFβ.
Figure 50:
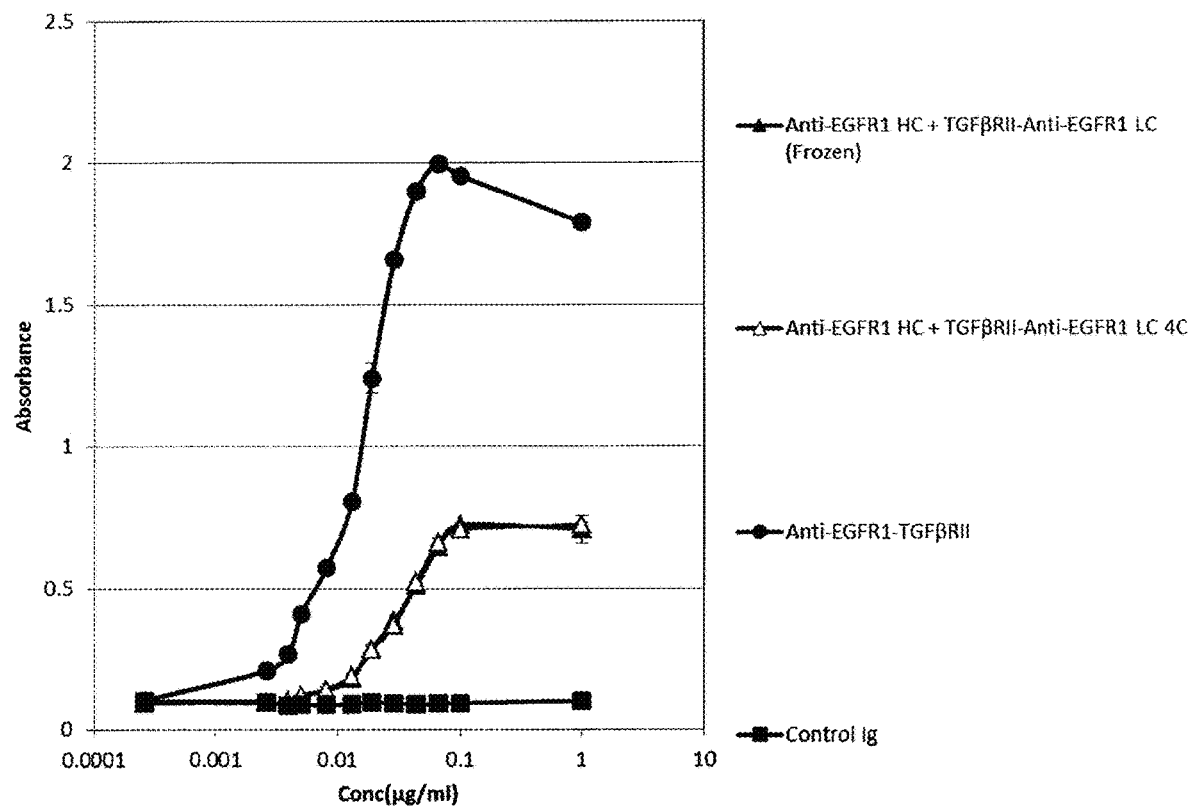
FIG. 50 shows Bifunctional ELISA. The Anti-EGFR1 HC+TGFβRII-Anti-EGFR1 LC fusion Mab binds to both its target EGFR1 and TGFβ at the same time.

For the bifunctional ELISA, rhEGFR-Fc chimera was coated onto NUNC maxisorb plates overnight at 4° C. The plates were washed and then blocked with superblock at room temperature for 2 hr. Different dilutions of the fusion Mab or the negative control antibody was added to the plate. The plate was incubated at room temperature for 1 hr. After washing, TGFβ was added and the plate was incubated at room temperature for 1 hr. The plate was washed and anti-TGFβ-biotin was added and the plate incubated at room temperature for 1 hr. The plate was washed and streptavidin-HRP was added and the plate incubated at room temperature for 1 hr. After washing, TMB substrate solution was added and the reaction stopped with 1N $H_2SO_4$. The absorbance was measured at 450 nm on a BioTek Synergy H4 hybrid reader.
Results:
The binding of the Anti-EGFR1 HC+TGFβRII-Anti-EGFR1 LC fusion Mab to both the targets EGFR1 (FIG. 48) and TGFβ (FIG. 49) was comparable with anti-EGFR1-TGFβRII. The Anti-EGFR1 HC+TGFβRII-Anti-EGFR1 LC fusion Mab was also tested in a bifunctional ELISA to determine whether the anti-EGFR1 and TGFβRII domains of the Mab can bind to their respective targets without interfering with each other. As seen in FIG. 50, the binding of Anti-EGFR1 HC+TGFβRII-Anti-EGFR1 LC fusion Mab is reduced as compared to anti-EGFR1-TGFβRII, suggesting that there is some interference in binding to either target due to the construction of the fusion Mab.

Binding to Cells Expressing EGFR1:

Procedure:

A-431 cells were grown in flasks until they reached 70-80% confluency. The cells were trypsinized and harvested. The cells were stained with different dilutions of Anti-EGFR1 HC+TGFβRII-Anti-EGFR1 LC fusion Mab or control Ig at 2-8° C. for 30 minutes. The cells were washed and incubated with anti-Human IgG-FITC conjugate at 2-8° C. for 30 minutes. After washing, the cells were analyzed on a flow cytometer. Live cells were gated based on their FSC vs SSC profiles. The total MFI for the gated population were recorded.

Figure 51:
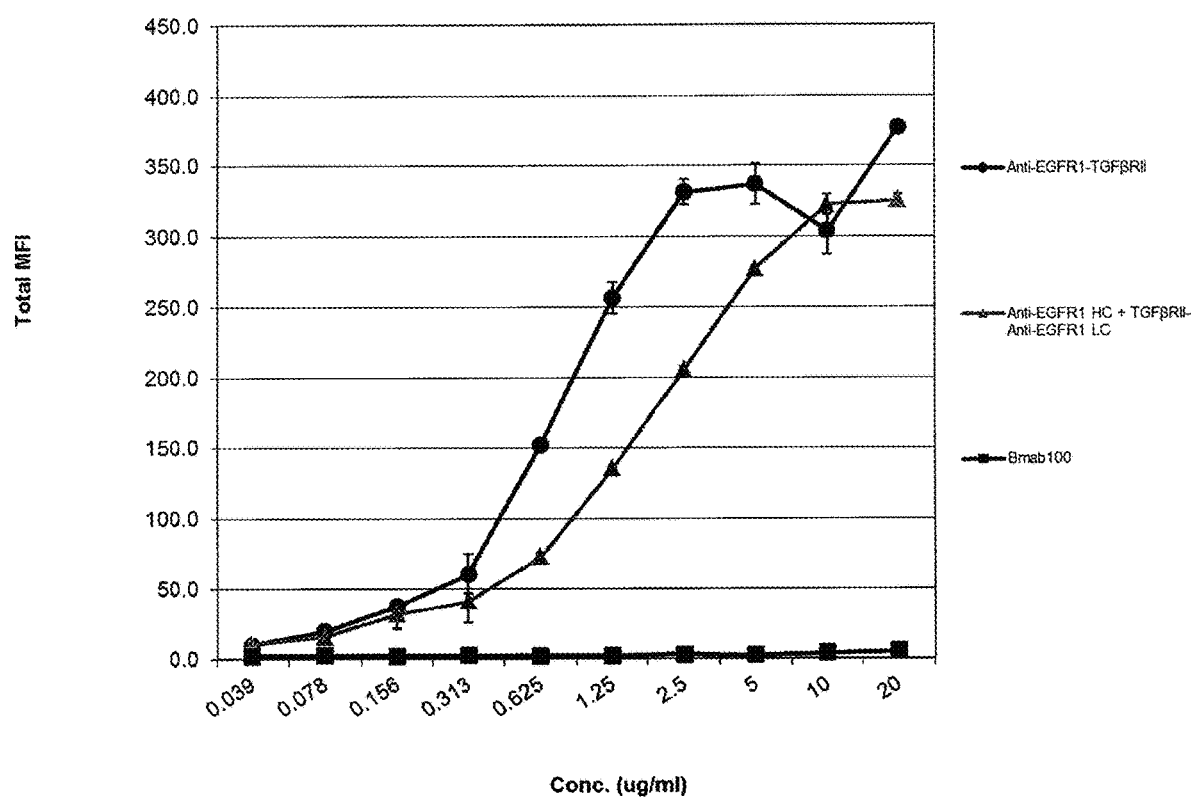
FIG. 51 shows flow cytometric analysis of the binding of the Anti-EGFR1 HC+TGFβRII-Anti-EGFR1 LC fusion Mab to EGFR1-expressing A431 cells.

Results:

The Anti-EGFR1 HC+TGFβRII-Anti-EGFR1 LC fusion binds to EGFR-expressing A-431 cells in a dose dependent manner (FIG. 51). The binding of Anti-EGFR1 HC+TGFβRII-Anti-EGFR1 LC is reduced compared to the binding of anti-EGFR1-TGFβRII.

8. Anti-EGFR1 HC-TGFβRII+TGFβRII-Anti-EGFR1 LC (Fmab 10)

Binding ELISAs: Procedure:

The fusion Mab was tested for its ability to bind to its targets in three different ELISAs: 1) EGFR1 target-binding ELISA, 2) TGFβ-target binding ELISA and 3) Bifunctional ELISA.

For the target binding ELISAs, the targets (rhEGFR-Fc chimera or TGFβ) were coated onto NUNC maxisorb plates overnight at 4° C. The plates were washed and then blocked with superblock at room temperature for 2 hr. Different dilutions of the fusion Mab or the negative control antibody was added to the plate. The plate was incubated at room temperature for 1 hr. Binding of the fusion Mab was detected by the addition of a biotinylated anti-human IgG F(ab)$_2$ secondary antibody, followed by a 1 hr incubation with peroxidase-conjugated streptavidin at room temperature. TMB substrate solution was added and the reaction stopped with 1N H$_2$SO$_4$. The absorbance was measured at 450 nm on a BioTek Synergy H4 Hybrid reader.

For the bifunctional ELISA, rhEGFR-Fc chimera was coated onto NUNC maxisorb plates overnight at 4° C. The plates were washed and then blocked with superblock at room temperature for 2 hr. Different dilutions of the fusion Mab or the negative control antibody was added to the plate. The plate was incubated at room temperature for 1 hr. After washing, TGFβ was added and the plate was incubated at room temperature for 1 hr. The plate was washed and anti-TGFβ-biotin was added and the plate incubated at room temperature for 1 hr.

The plate was washed and streptavidin-HRP was added and the plate incubated at room temperature for 1 hr. After washing, TMB substrate solution was added and the reaction stopped with 1N H$_2$SO$_4$. The absorbance was measured at 450 nm on a BioTek Synergy H4 hybrid reader.

Figure 52:
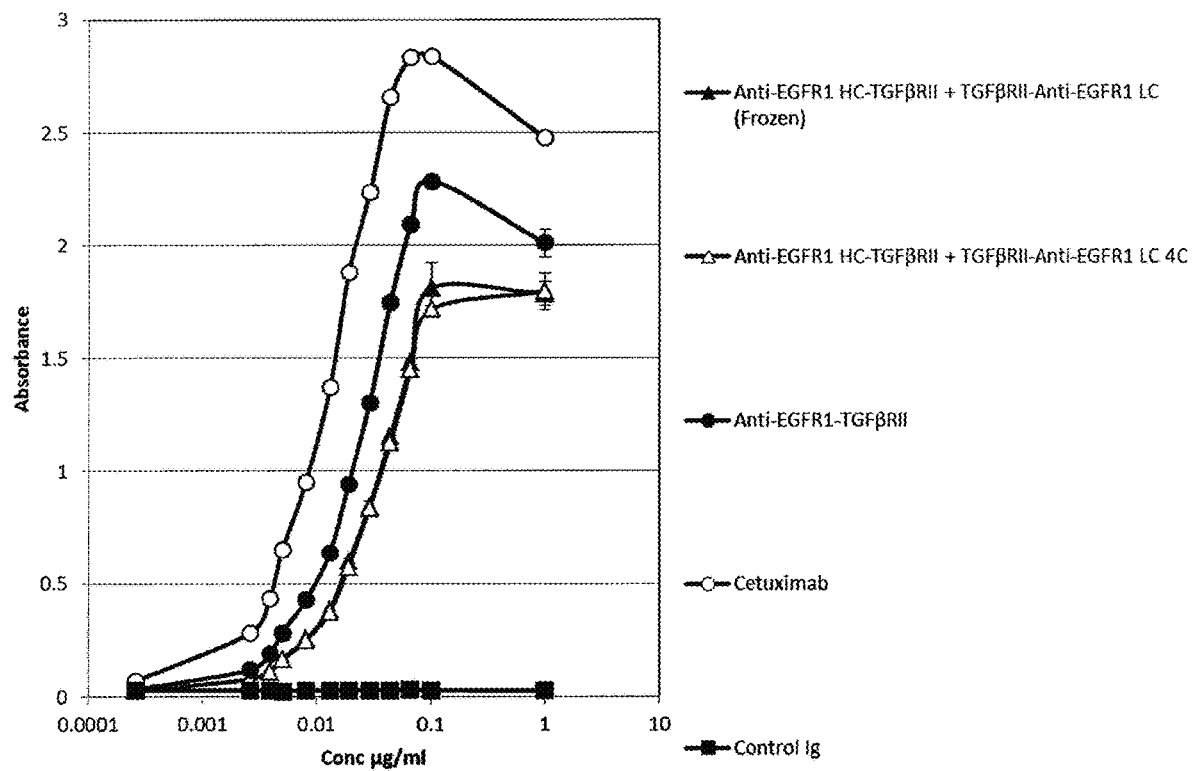
FIG. 52 shows EGFR1 target binding ELISA. The Anti-EGFR1 HC-TGFβRII+TGFβRII-Anti-EGFR1 LC fusion Mab binds to its immobilized target EGFR1.
Figure 53:
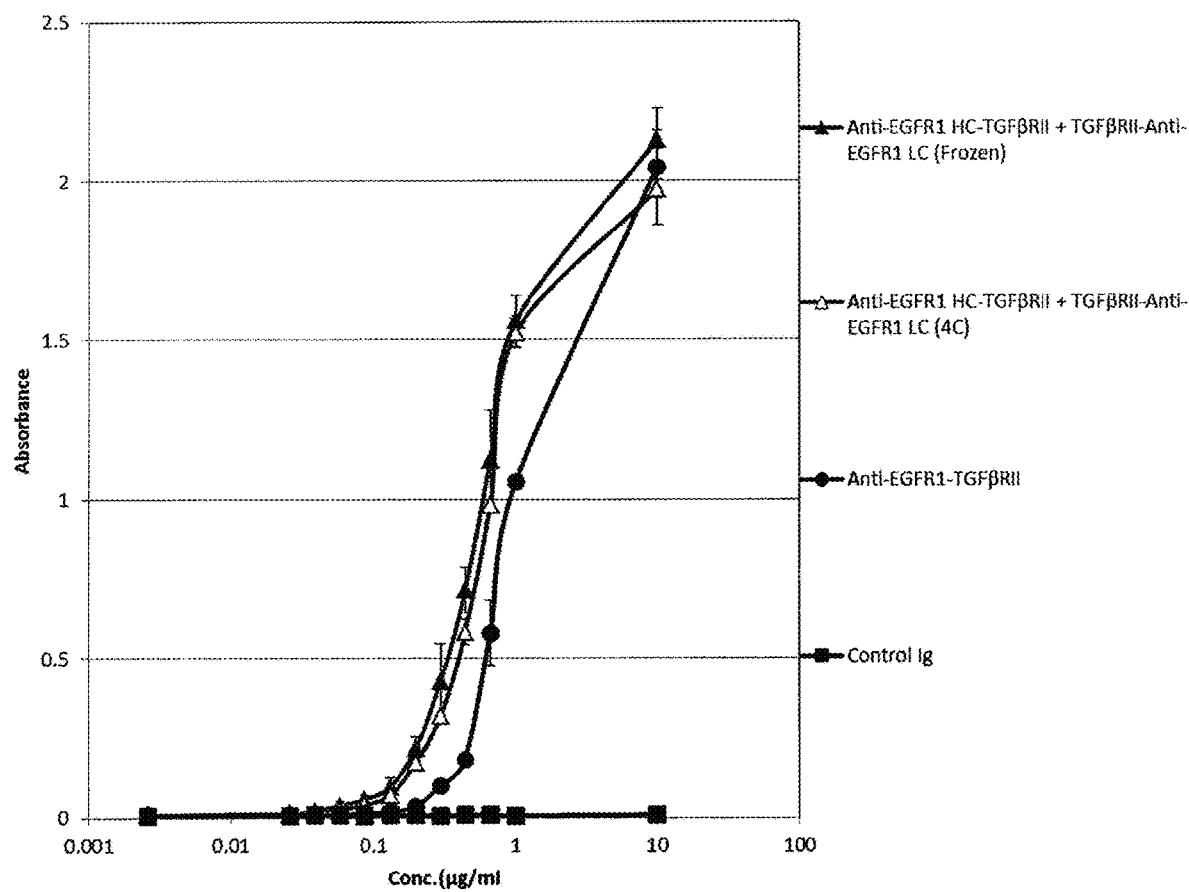
FIG. 53 shows TGFβ target binding ELISA. The Anti-EGFR1 HC-TGFβRII+TGFβRII-Anti-EGFR1 LC fusion Mab binds to its target TGFβ.
Figure 54:
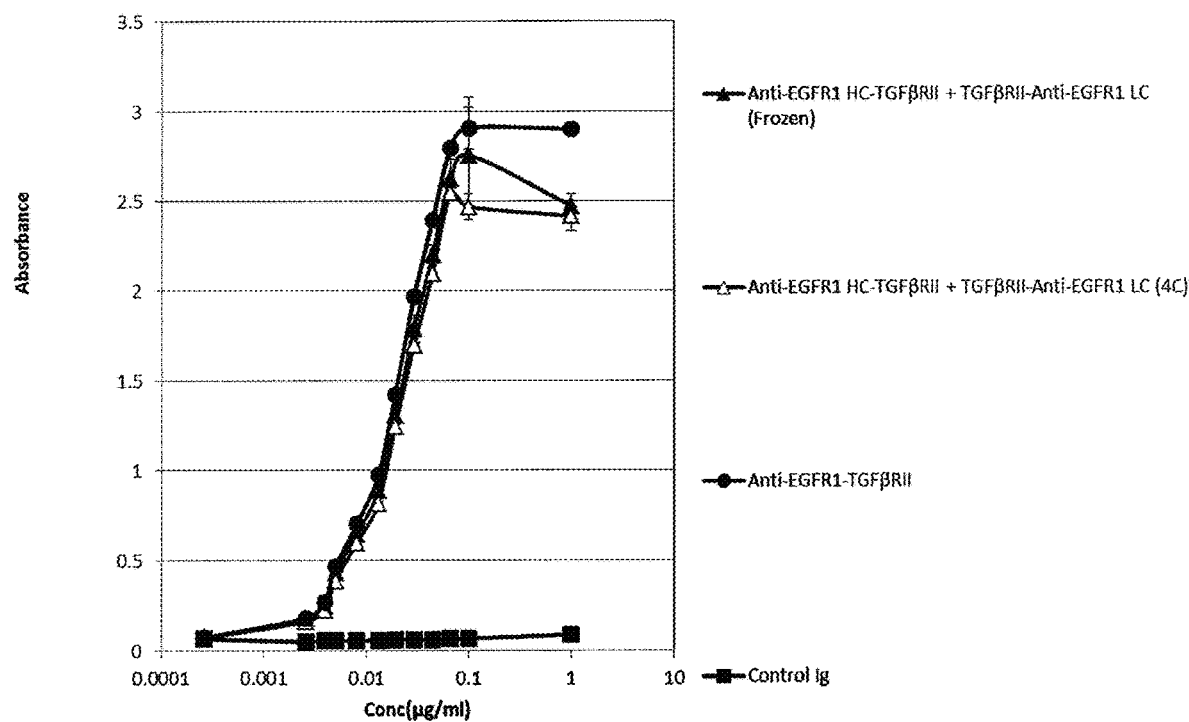
FIG. 54 shows Bifunctional ELISA. The Anti-EGFR1 HC-TGFβRII+TGFβRII-Anti-EGFR1 LC fusion Mab binds to both its target EGFR1 and TGFβ at the same time.
Figure 55:
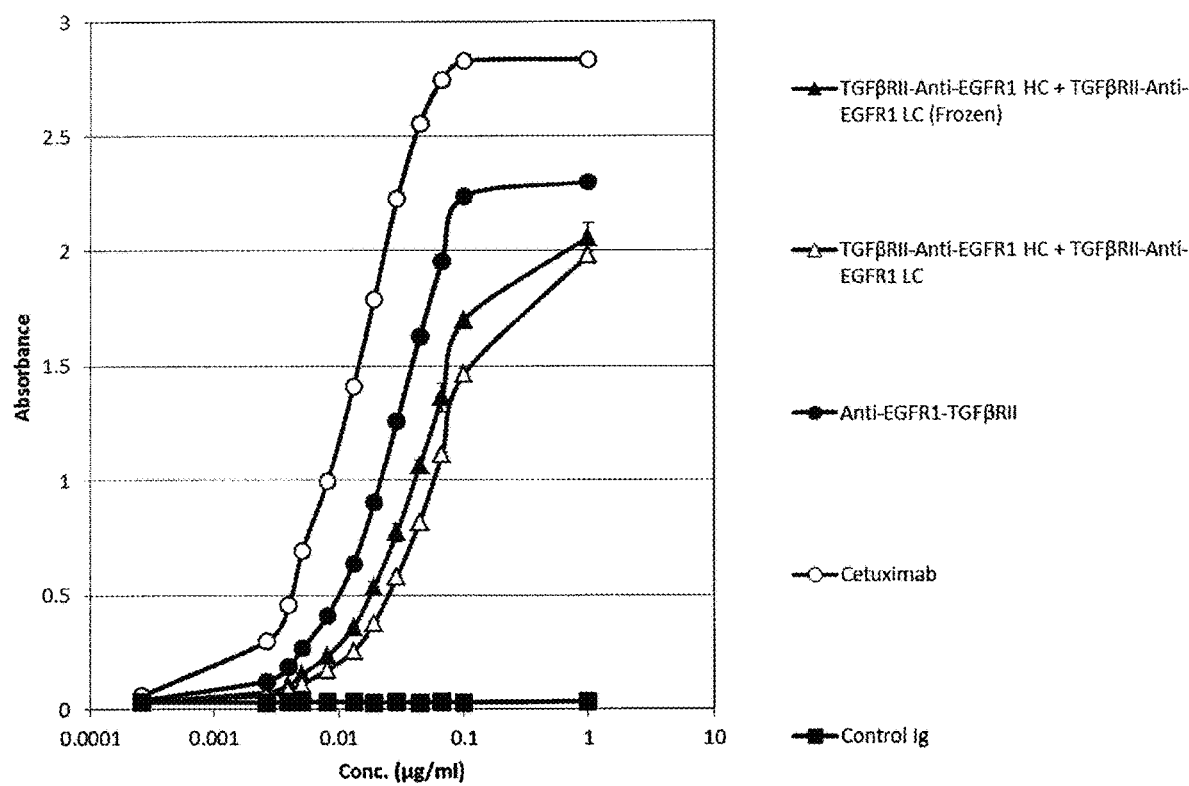
FIG. 55 shows EGFR1 target binding ELISA. The TGFβRII-Anti-EGFR1 HC+TGFβRII-Anti-EGFR1 LC fusion Mab binds to its immobilized target EGFR1.

Results:

The binding of Anti-EGFR1 HC-TGFβRII+TGFβRII-Anti-EGFR1 LC fusion EGab to the target EGFR1 was slightly reduced (FIG. 52) but was higher for TGFβ (FIG. 53) when compared to the binding of anti-EGFR1-TGFβRII. The Anti-EGFR1-TGFβRII+TGFβRII-Anti-EGFR1 LC fusion Mab was also tested in a bifunctional ELISA to determine whether the anti-EGFR1 and TGFβRII domains of the Mab can bind to their respective targets without interfering with each other. As seen in FIG. 54, the binding of Anti-EGFR1 HC-TGFβRII+TGFβRII-Anti-EGFR1 LC fusion Mab is comparable to anti-EGFR1-TGFβRII, suggesting that there is no interference in binding to either target due to the construction of the fusion Mab.

9. TGFβRII-Anti-EGFR1 HC+TGFβRII-Anti-EGFR1 LC (Fmab 12)

Binding ELISAs: Procedure:

The fusion Mab was tested for its ability to bind to its targets in three different ELISAs: 1) EGFR1 target-binding ELISA, 2) TGFβ-target binding ELISA and 3) Bifunctional ELISA.

For the target binding ELISAs, the targets (rhEGFR-Fc chimera or TGFβ) were coated onto NUNC maxisorb plates overnight at 4° C. The plates were washed and then blocked with superblock at room temperature for 2 hr. Different dilutions of the fusion Mab or the negative control antibody was added to the plate. The plate was incubated at room temperature for 1 hr. Binding of the fusion Mab was detected by the addition of a biotinylated anti-human IgG F(ab)$_2$ secondary antibody, followed by a 1 hr incubation with peroxidase-conjugated streptavidin at room temperature. TMB substrate solution was added and the reaction stopped with 1N H$_2$SO$_4$. The absorbance was measured at 450 nm on a BioTek Synergy H4 Hybrid reader.

For the bifunctional ELISA, rhEGFR-Fc chimera was coated onto NUNC maxisorb plates overnight at 4° C. The plates were washed and then blocked with superblock at room temperature for 2 hr. Different dilutions of the fusion Mab or the negative control antibody was added to the plate. The plate was incubated at room temperature for 1 hr. After washing, TGFβ was added and the plate was incubated at room temperature for 1 hr. The plate was washed and anti-TGFβ-biotin was added and the plate incubated at room temperature for 1 hr. The plate was washed and streptavidin-HRP was added and the plate incubated at room temperature for 1 hr. After washing, TMB substrate solution was added and the reaction stopped with 1N H2504. The absorbance was measured at 450 nm on a BioTek Synergy H4 hybrid reader.

Figure 56:
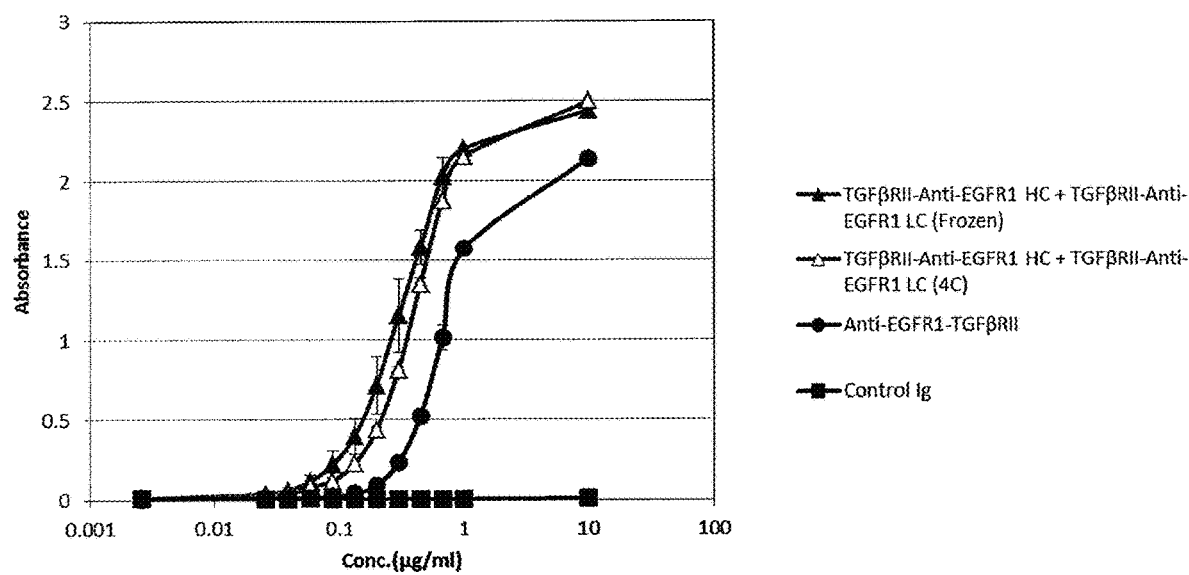
FIG. 56 shows TGFβ target binding ELISA. TGFβRII-Anti-EGFR1 HC+TGFβRII-Anti-EGFR1 LC fusion Mab binds to its target TGFβ.
Figure 57:
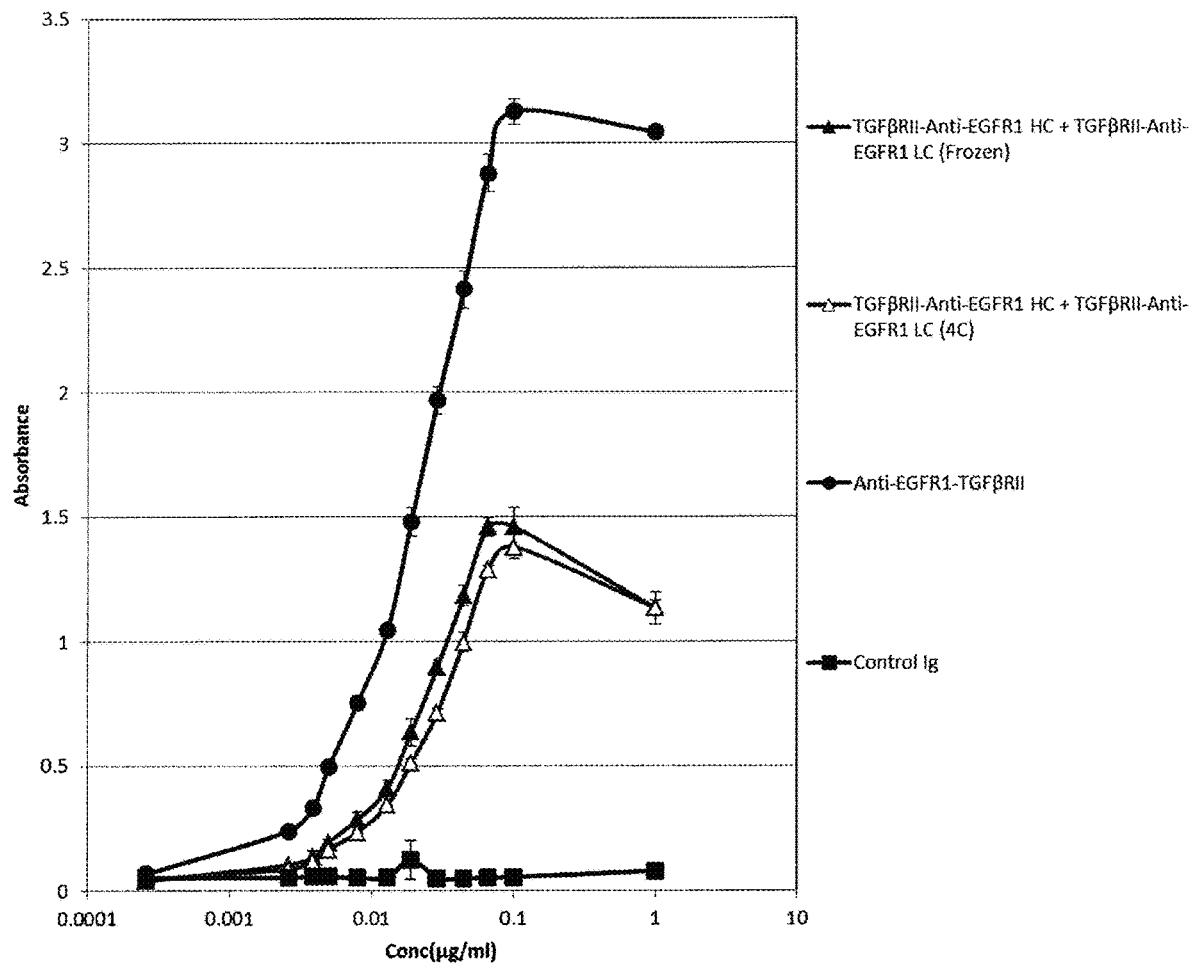
FIG. 57 shows Bifunctional ELISA. The TGFβRII-Anti-EGFR1 HC+TGFβRII-Anti-EGFR1 LC fusion Mab binds to both its target EGFR1 and TGFβ at the same time.
Figure 58:
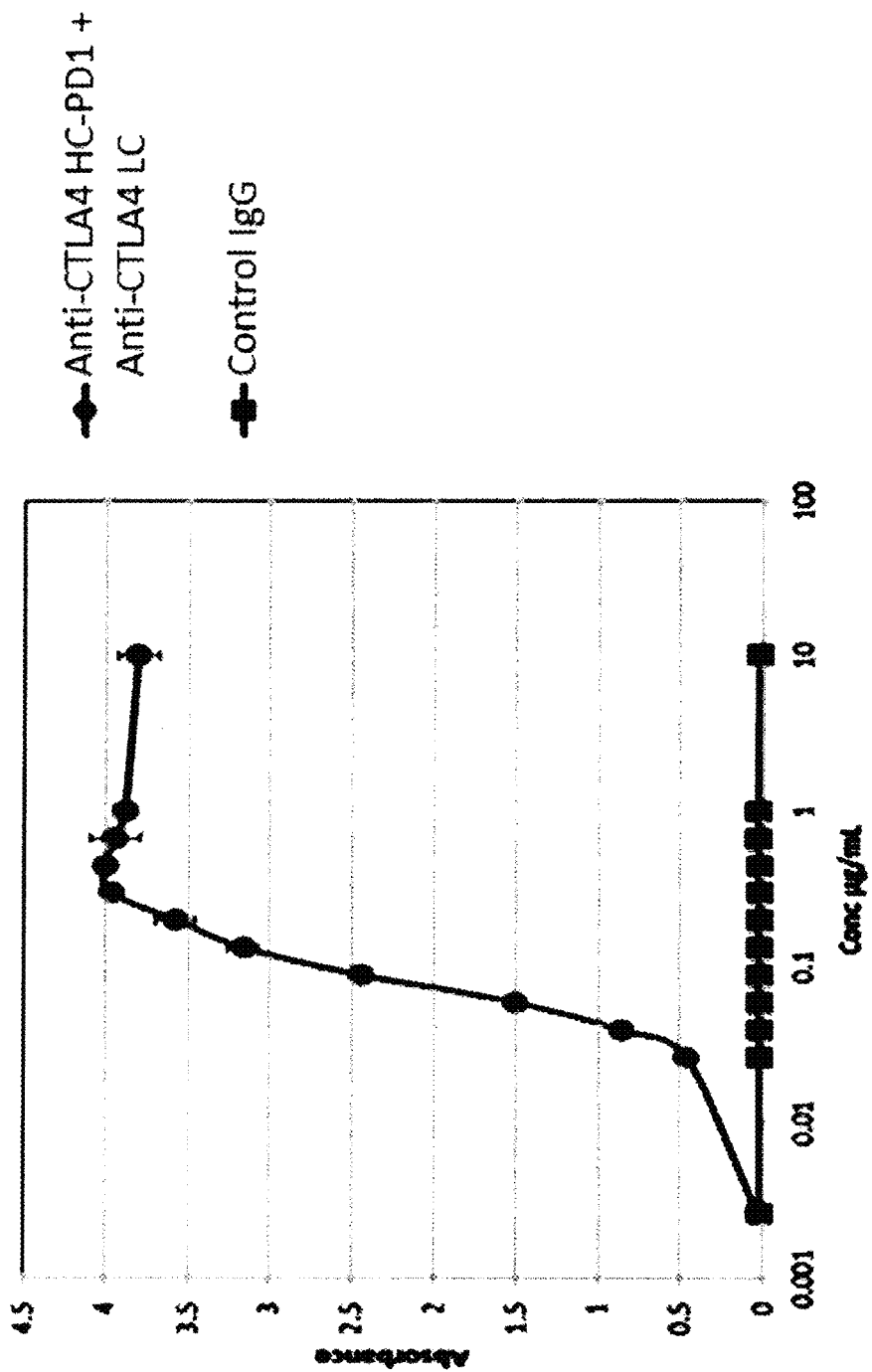
FIG. 58 shows Bifunctional ELISA. The Anti-CTLA4 HC-PD1+Anti-CTLA4 LC fusion Mab binds to both its target CTLA4 and PDL1 at the same time.
Figure 59:
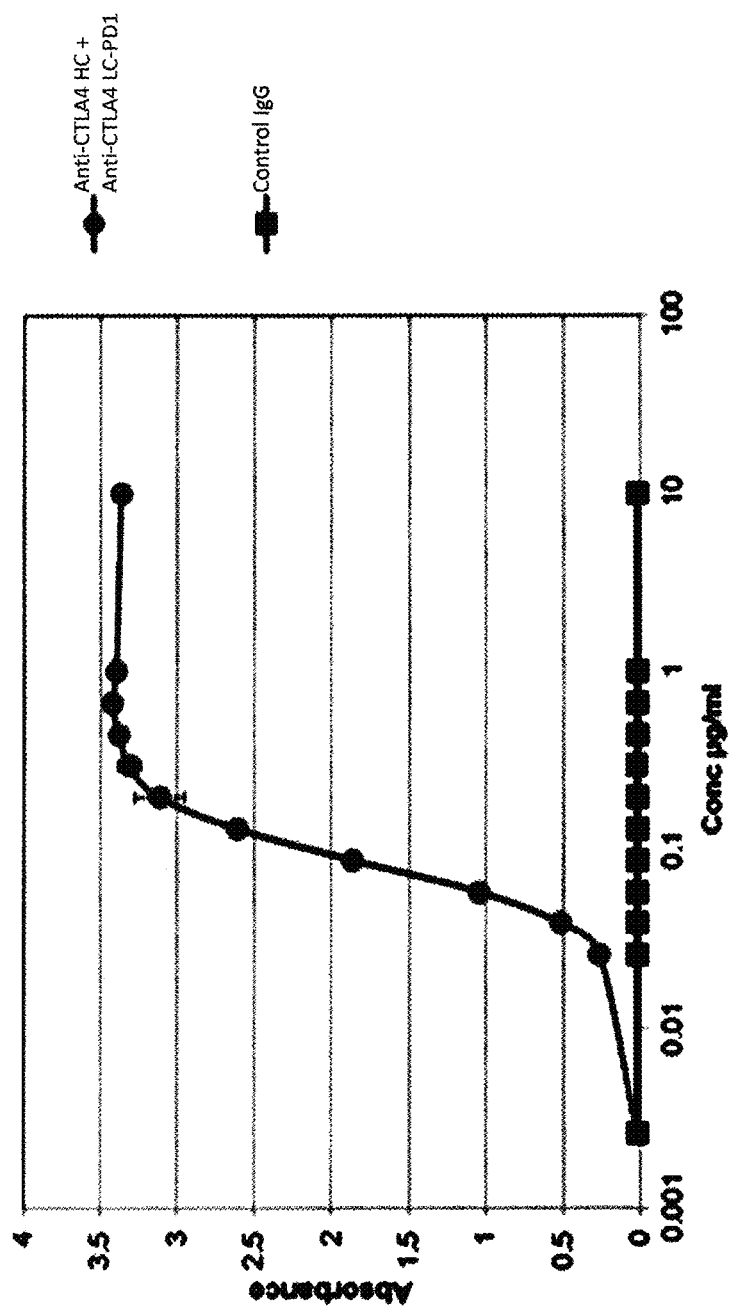
FIG. 59 shows Bifunctional ELISA. The Anti-CTLA4 HC+Anti-CTLA4 LC-PD1 fusion Mab binds to both its target CTLA4 and PDL1 at the same time.
Figure 60:
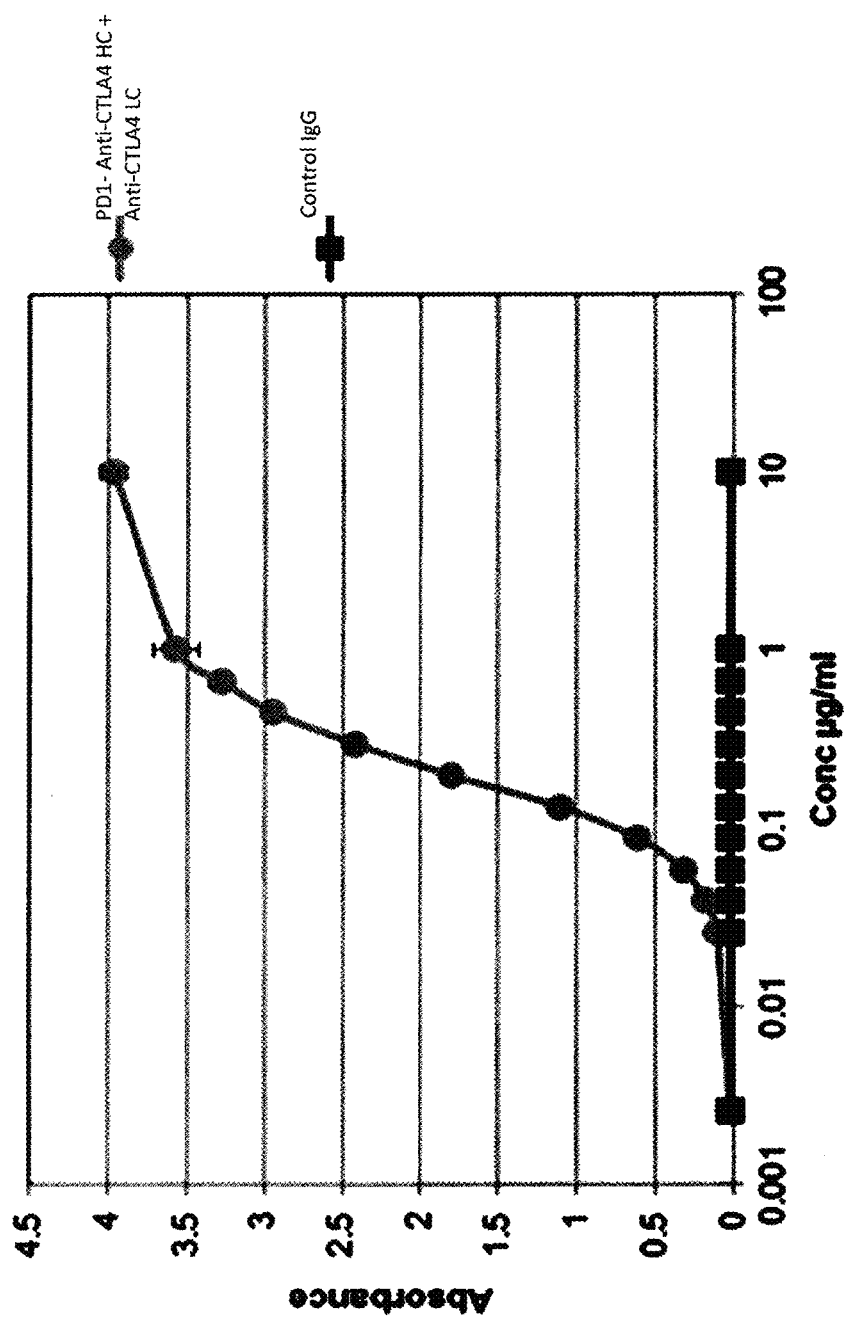
FIG. 60 shows Bifunctional ELISA. The PD1-Anti-CTLA4 HC+Anti-CTLA4 LC fusion Mab binds to both its target CTLA4 and PDL1 at the same time.
Figure 61:
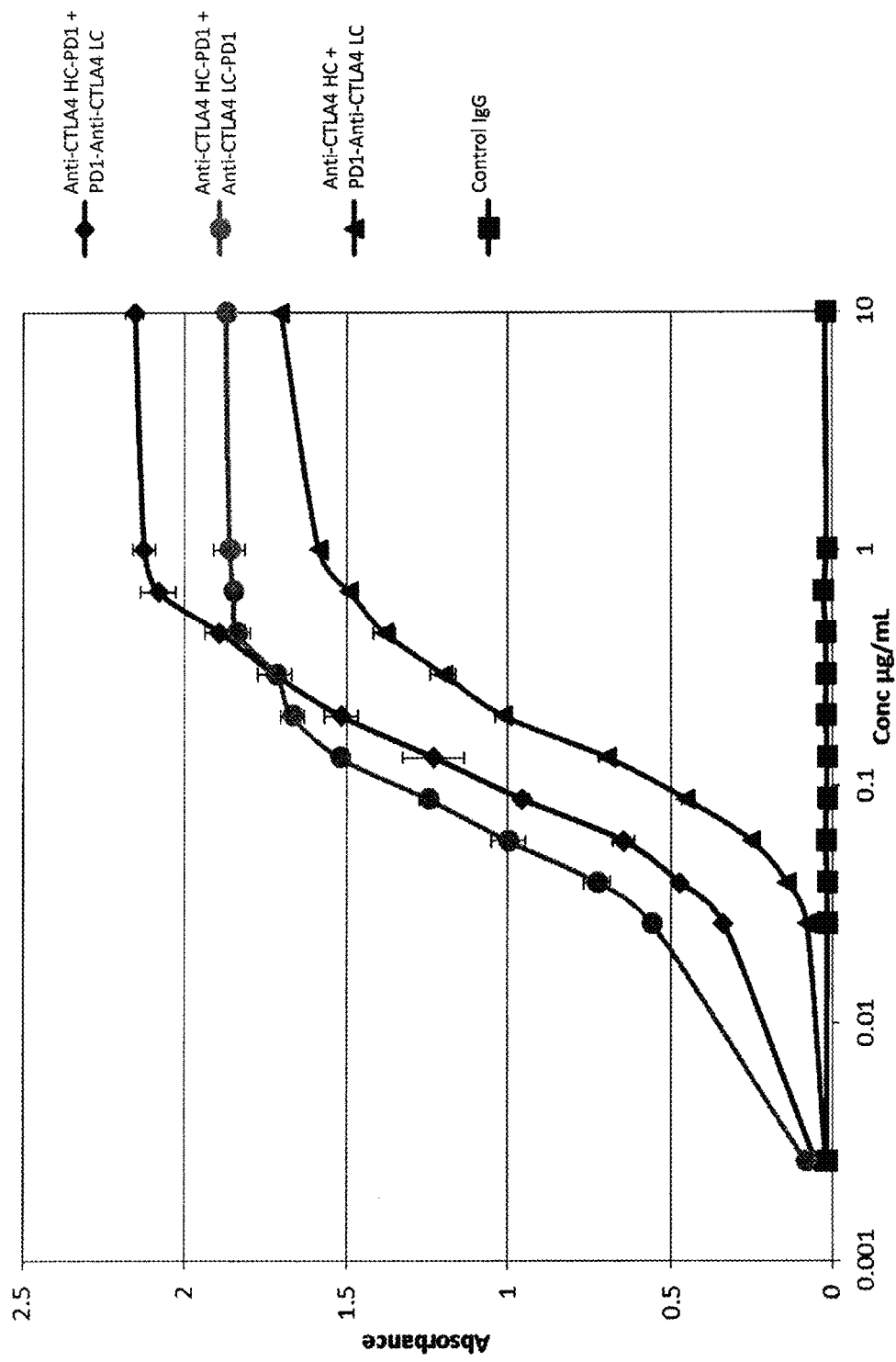
FIG. 61 shows Bifunctional ELISA. The Anti-CTLA4 HC-PD1+PD1-Anti-CTLA4 LC-PD1, Anti-CTLA4 HC-PD1+Anti-CTLA4 LC-PD1 and Anti-CTLA4 HC-PD1+PD1-Anti-CTLA4 LC fusion Mabs binds to both their target CTLA4 and PDL1 at the same time.
Figure 62:
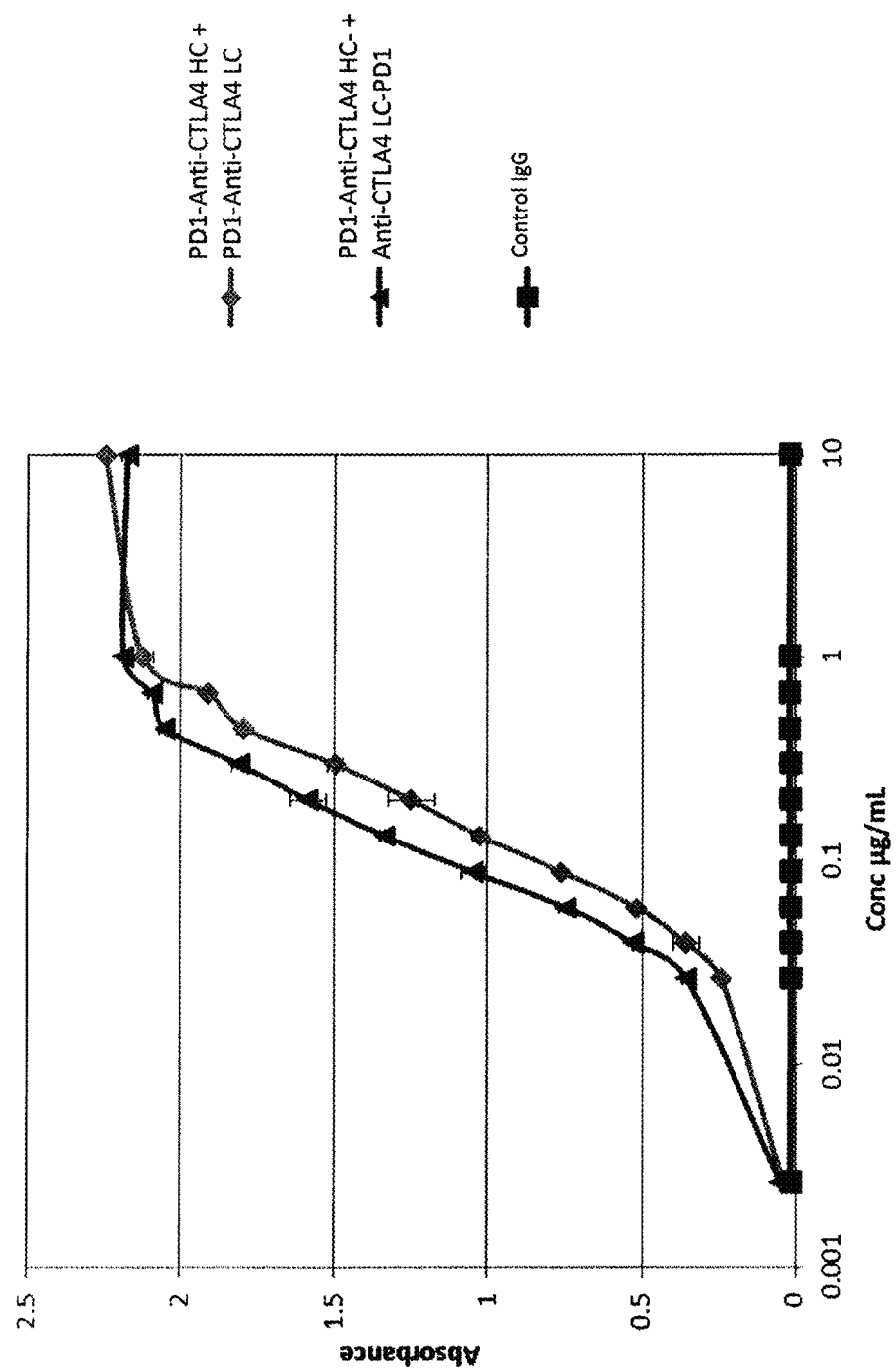
FIG. 62 shows Bifunctional ELISA. The PD1-Anti-CTLA4 HC+Anti-CTLA4 LC-PD1 and PD1-Anti-CTLA4 HC+PD1-Anti-CTLA4 LC fusion Mabs binds to both their target CTLA4 and PDL1 at the same time.
Figure 63:
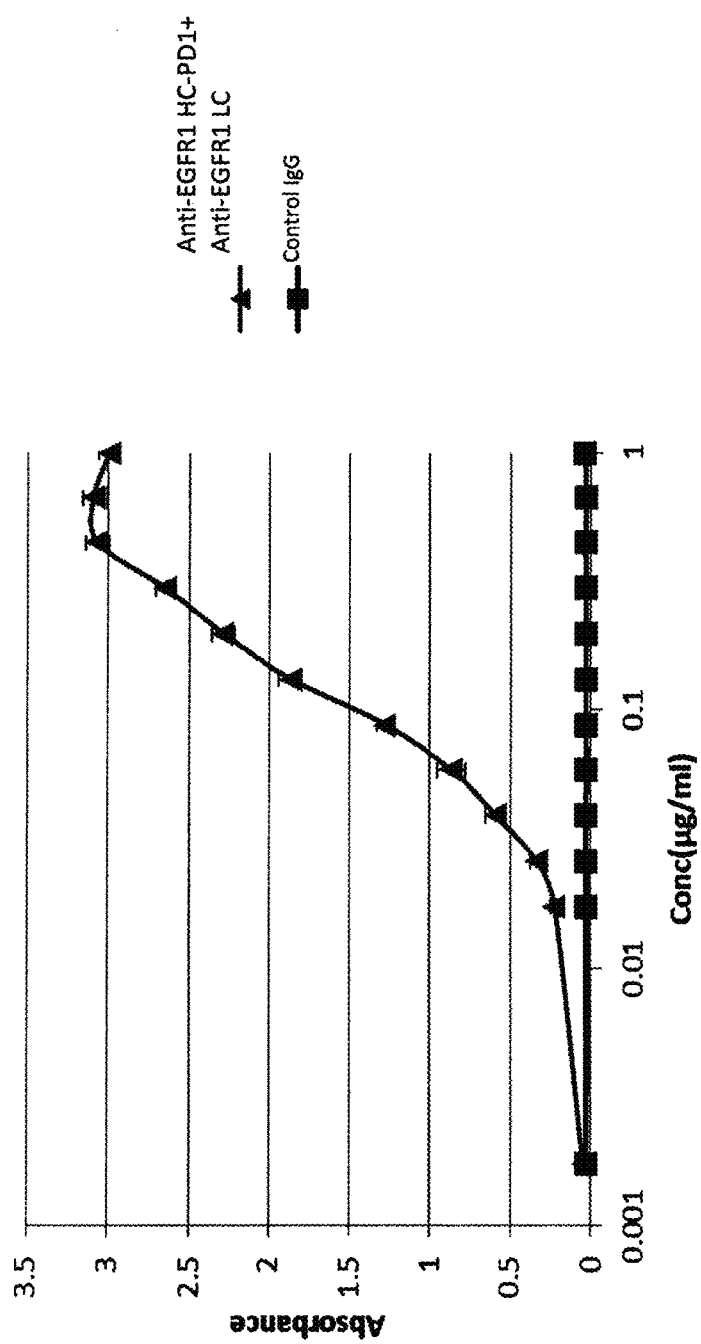
FIG. 63 shows Bifunctional ELISA. The Anti-EGFR1 HC-PD1+Anti-EGFR1 LC fusion Mab binds to both its target EGFR and PDL1 at the same time.
Figure 64:
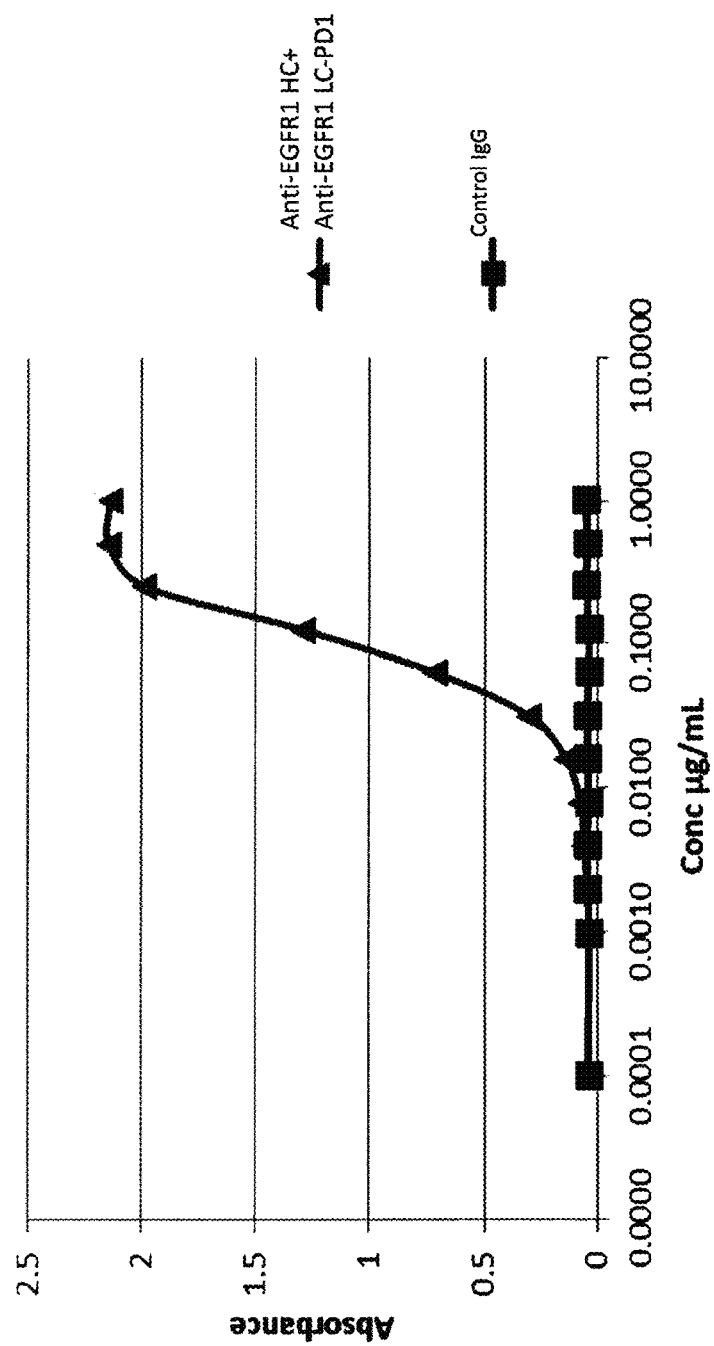
FIG. 64 shows Bifunctional ELISA. The Anti-EGFR1 HC+Anti-EGFR1 LC-PD1 fusion Mab binds to both its target EGFR and PDL1 at the same time.

Results:

The binding of TGFβRII-Anti-EGFR1 HC+TGFβRII-Anti-EGFR1 LC fusion Mab to the target EGFR1 was slightly reduced (FIG. 53) but was higher for TGFβ (FIG. 56) when compared to the binding of anti-EGFR1-TGFβRII. The TGFβRII-Anti-EGFR1 HC+TGFβRII-Anti-EGFR1 LC fusion Mab was also tested in a bifunctional ELISA to determine whether the anti-EGFR1 and TGFβRII domains of the Mab can bind to their respective targets without interfering with each other. As seen in FIG. 57, the binding of TGFβRII-Anti-EGFR1 HC+TGFβRII-Anti-EGFR1 LC fusion Mab is reduced compared to anti-EGFR1-TGFβRII, suggesting that there is interference in binding to either target due to the construction of the fusion Mab.

REFERENCES

The contents of all references cited herein are incorporated by reference herein for all purposes.

Altschul, et al., 1990, Basic local alignment search tool, *J Mol. Biol.* 15:403-10.

Ausubel, et al., (ed), 1998, Current Protocols in Molecular Biology, Vol. 2, Ch. 13, Greene Publish. Assoc. & Wiley Interscience.

Bitter, et al., 1987, Expression and Secretion Vectors for Yeast; *Methods in Enzymology,* 153:5 16-544.

Bitter, 1987, Heterologous Gene Expression in Yeast, *Methods in Enzymology,* Vol. 152, pp. 673-684.

Dong M., et al., 2006, Role of transforming growth factor-β in hematologic malignancies. *Blood.* 107:4589-4596.

Deutscher, M., et al., Guide to Protein Purification: Methods in Enzymology, Vol. 182, Academic Press (1990).

Flies, et al., 2011, Blockade of the B7-H1/PD-1 Pathway for Cancer Immunotherapy, *J Biol Med.,* 84(4): 409-421.

Glover, 1986, DNA Cloning, Vol. II, Ch. 3, IRL Press, Wash., D.C.

Gluzman (ed.), 1982, Eukaryotic Viral Vectors, Cold Spring Harbor, N.Y.: Cold Spring Harbor Laboratory.

Grant, et al., 1987, Expression and Secretion Vectors for Yeast, *Methods in Enzymology,* Vol. 153, 516-544.

Lee, et al., 1994, Delivery of liposomes into cultured KB cells via folate receptor-mediated endocytosis. *J Biol. Chem.,* 269:3 198.

Lee, et al., 1995, Folate-mediated tumor cell targeting of liposome-entrapped doxorubicin in vitro. *Biochem. Biophys. Actu,* 1233: 134-144.

Mackett, et al., 1982, Vaccinia virus: a selectable eukaryotic cloning and expression vector, *Proc. Natl. Acad. Sci. USA,* 79:7415-7419.

Mackett, et al., 1984, General method for production and selection of infectious vaccinia virus, *J Virol.,* 49:857-864.

Nomi, et al., 2007, Clinical significance and therapeutic potential of the programmed death-1 ligand/programmed death-1 pathway in human pancreatic cancer. *Clin Cancer Res.,* 13:2151-7.

Okazaki, et al., 2007, PD-1 and PD-1 ligands: from discovery to clinical Application. *International Immunology,* Vol. 19, No. 7, pp. 813-824.

Panicali, et al., 1982, Construction of poxviruses as cloning vectors: insertion of the thymidine, *Proc. Natl. Acad. Sci. USA,* 79:4927-4931.

Pardoll, D M., 2012, The blockage of immune checkpoints in cancer immunotherapy. *Nat. Rev. Cancer,* 12(4): 252-64.

Strathem, et al., 1982, The Molecular Biology of the Yeast *Saccharomyces,* Cold Spring Harbor Press, Vols. I and II.

Thompson R H, et al., 2004, Costimulatory B7-H1 in renal cell carcinoma patients: Indicator of tumor aggressiveness and potential therapeutic target. *Proc Natl Acad Sci USA,* 101(49):17174-9.

Teicher B A., 2001, Malignant cells, directors of the malignant process: role of transforming growth factor beta. *Cancer Metastasis Rev;* 20:133-143.

Wrzesinski, et al., 2007, Transforming Growth Factor-β and the Immune Response: Implications for Anticancer Therapy, *Clin Cancer Res,* 13; 5262.

---

That which is claimed:

1. A fusion protein comprising a targeting moiety and an immunomodulating moiety exhibiting bi-specificity, wherein the targeting moiety and the immunomodulating moiety are linked by an amino acid spacer encoded by nucleotide sequence SEQ ID NO: 4, wherein the immunomodulating moiety is encoded by nucleotide sequence SEQ ID NO: 3 or SEQ ID NO: 7, wherein the targeting moiety is an anti-EGFR1 antibody comprising a heavy chain and a light chain encoded by nucleotide sequences consisting of SEQ ID NO: 1 and SEQ ID NO: 2, respectively, and wherein the immunomodulating moiety is attached via the amino acid spacer to the C-terminus of the heavy chain or the light chain.

2. A fusion protein comprising a targeting moiety and an immunomodulating moiety exhibiting bi-specificity, wherein the targeting moiety and the immunomodulating moiety are linked by an amino acid spacer encoded by nucleotide sequence SEQ ID NO: 4, wherein the immunomodulating moiety is encoded by nucleotide sequence SEQ ID NO: 3 or SEQ ID NO: 7, wherein the targeting moiety is an anti-CTLA-4 antibody comprising a heavy chain and a light chain encoded by nucleotide sequences consisting of SEQ ID NO: 5 and SEQ ID NO: 6, respectively, and wherein the immunomodulating moiety is attached via the amino acid spacer to the C-terminus of the heavy chain or the light chain.

* * * * *